US012742184B2

(12) United States Patent
Yu et al.

(10) Patent No.: US 12,742,184 B2
(45) Date of Patent: Sep. 22, 2026

(54) METHODS FOR MANUFACTURING GENETICALLY ENGINEERED CAR-T CELLS

(71) Applicant: CRISPR THERAPEUTICS AG, Zug (CH)

(72) Inventors: Hui Yu, Cambridge, MA (US); Mary-Lee Dequeant, Cambridge, MA (US); Demetrios Kalaitzidis, Cambridge, MA (US); Mohammed Ghonime, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 1006 days.

(21) Appl. No.: 17/814,930

(22) Filed: Jul. 26, 2022

(65) Prior Publication Data

US 2023/0046228 A1 Feb. 16, 2023

Related U.S. Application Data

(60) Provisional application No. 63/246,975, filed on Sep. 22, 2021, provisional application No. 63/241,801, (Continued)

(51) Int. Cl.
*C12N 15/90* (2006.01)
*A61K 40/11* (2025.01)
(Continued)

(52) U.S. Cl.
CPC ............ *C12N 15/907* (2013.01); *A61K 40/11* (2025.01); *A61K 40/31* (2025.01);
(Continued)

(58) Field of Classification Search
CPC ...... C12N 15/907; C12N 5/0636; C12N 9/22; C12N 15/11; C12N 15/625; A61K 40/11;
(Continued)

(56) References Cited

U.S. PATENT DOCUMENTS

| | | | |
|---|---|---|---|
| 10,166,255 | B2 | 1/2019 | Moriarity et al. |
| 10,729,725 | B2 | 8/2020 | Terrett et al. |

(Continued)

FOREIGN PATENT DOCUMENTS

| | | | |
|---|---|---|---|
| EA | 048895 B1 * | 1/2025 | |
| EP | 3854877 A1 | 7/2021 | |

(Continued)

OTHER PUBLICATIONS

Webber (Webber, Beau R., et al. "Highly efficient multiplex human T cell engineering without double-strand breaks using Cas9 base editors." Nature communications 10.1 (2019): 5222). (Year: 2019).*

(Continued)

*Primary Examiner* — Tracy Vivlemore
*Assistant Examiner* — Thomas R. Amick
(74) *Attorney, Agent, or Firm* — Casimir Jones, S.C.; J. Mitchell Jones

(57) ABSTRACT

Methods for manufacturing genetically engineered T cells expressing a chimeric antigen receptor (CAR), such as a CAR that binds human CD19, BCMA, or CD70, and having multiple additional gene edits, for example, a disrupted Regnase-1 gene, a disrupted TGFBRII gene, a disrupted TRAC gene, a disrupted β2M gene, or a combination thereof, using CRISPR/Cas gene editing systems.

34 Claims, 23 Drawing Sheets

Specification includes a Sequence Listing.

TRAC

Related U.S. Application Data filed on Sep. 8, 2021, provisional application No. 63/225,762, filed on Jul. 26, 2021.

(51) Int. Cl.

| | |
|---|---|
| ***A61K 40/31*** | (2025.01) |
| ***A61K 40/42*** | (2025.01) |
| ***A61K 40/50*** | (2025.01) |
| ***C07K 14/705*** | (2006.01) |
| ***C07K 14/725*** | (2006.01) |
| ***C07K 16/28*** | (2006.01) |
| ***C12N 5/0783*** | (2010.01) |
| ***C12N 9/22*** | (2006.01) |
| ***C12N 15/11*** | (2006.01) |
| ***C12N 15/62*** | (2006.01) |

(52) U.S. Cl.

CPC ...... *A61K 40/4211* (2025.01); *A61K 40/4232* (2025.01); *C07K 14/7051* (2013.01); *C07K 14/70517* (2013.01); *C07K 14/70521* (2013.01); *C07K 16/2803* (2013.01); *C12N 5/0636* (2013.01); *C12N 9/22* (2013.01); *C12N 15/11* (2013.01); *C12N 15/625* (2013.01); *A61K 40/50* (2025.01); *A61K 2239/31* (2023.05); *A61K 2239/38* (2023.05); *A61K 2239/48* (2023.05); *C07K 2317/622* (2013.01); *C07K 2319/02* (2013.01); *C07K 2319/03* (2013.01); *C12N 2310/20* (2017.05); *C12N 2800/80* (2013.01)

(58) Field of Classification Search

CPC ............... A61K 40/31; A61K 40/4211; A61K 40/4232; A61K 40/50; A61K 2239/31; A61K 2239/38; A61K 2239/48; C07K 14/7051; C07K 14/70517; C07K 14/70521; C07K 16/2803; C07K 2317/622; C07K 2319/02; C07K 2319/03

See application file for complete search history.

(56) References Cited

U.S. PATENT DOCUMENTS

| | | | | |
|---|---|---|---|---|
| 10,736,919 | B2 | 8/2020 | Terrett et al. | |
| 10,857,184 | B2 | 12/2020 | Terrett et al. | |
| 10,881,689 | B2 | 1/2021 | Terrett et al. | |
| 11,071,755 | B1 | 7/2021 | Terrett et al. | |
| 11,135,247 | B2 | 10/2021 | Terrett et al. | |
| 11,166,985 | B2 | 11/2021 | Terrett et al. | |
| 11,191,783 | B2 | 12/2021 | Terrett et al. | |
| 2017/0211075 | A1 | 7/2017 | Lee et al. | |
| 2018/0112198 | A1 | 4/2018 | Liu et al. | |
| 2018/0325955 | A1* | 11/2018 | Terrett | A61P 35/00 |
| 2019/0284553 | A1* | 9/2019 | Benson | A61P 35/04 |
| 2020/0181610 | A1 | 6/2020 | Benson et al. | |
| 2021/0139850 | A1 | 5/2021 | Yu et al. | |
| 2023/0381315 | A1* | 11/2023 | Sadelain | A61K 40/11 |

FOREIGN PATENT DOCUMENTS

| | | | | |
|---|---|---|---|---|
| JP | WO 2017/002928 | A1 | 4/2018 | |
| WO | WO 2010/098429 | A1 | 9/2010 | |
| WO | WO-2014153114 | A1 * | 9/2014 | A61K 47/6849 |
| WO | WO-2015187528 | A1 * | 12/2015 | A61P 35/02 |
| WO | WO 2016/069282 | A1 | 5/2016 | |
| WO | WO 2018/115887 | A1 | 6/2018 | |
| WO | WO 2019/089884 | A2 | 5/2019 | |
| WO | WO 2019/097305 | A1 | 5/2019 | |
| WO | WO 2019/152742 | A1 | 8/2019 | |
| WO | WO 2019/178421 | A1 | 9/2019 | |
| WO | WO 2019/215500 | A1 | 11/2019 | |
| WO | WO 2019/235581 | A1 | 12/2019 | |
| WO | WO 2020/032160 | A1 | 2/2020 | |
| WO | WO 2020/095107 | A1 | 5/2020 | |
| WO | WO 2020/206248 | A1 | 10/2020 | |
| WO | WO-2020223535 | A1 * | 11/2020 | A61K 40/42 |
| WO | WO 2021/095012 | A1 | 5/2021 | |
| WO | WO 2021/095013 | A1 | 5/2021 | |
| WO | WO 2022/064428 | A1 | 3/2022 | |
| WO | WO 2022/137181 | A1 | 6/2022 | |

OTHER PUBLICATIONS

Wei (Wei, Jun, et al. "Targeting REGNASE-1 programs long-lived effector T cells for cancer therapy." Nature 576.7787 (2019): 471-476 (Year: 2019).*

Eyquem (Eyquem, Justin, et al. "Targeting a CAR to the TRAC locus with CRISPR/Cas9 enhances tumour rejection." Nature 543. 7643 (2017): 113-117.) (Year: 2017).*

Rogers ( Geoffrey L. Rogers, Chun Huang, Robert Clark, Eduardo Seclen, Hsu-Yu Chen, Paula M. Cannon "Optimization of AAV6 transduction enhances site-specific genome editing of primary human lymphocytes" bioRxiv 2021.05.03.440656; (May 3, 2021). (Year: 2021).*

Basila (Basila, Megan et al. "Minimal 2'-O-methyl phosphorothioate linkage modification pattern of synthetic guide RNAs for increased stability and efficient CRISPR-Cas9 gene editing avoiding cellular toxicity." PloS one vol. 12, 11 e0188593. Nov. 27, 2017) (Year: 2017).*

Sauer (Sauer, Tim et al. "CD70-specific Car T cells have potent activity against acute myeloid leukemia without HSC toxicity." Blood vol. 138,4 (2021): 318-330) (Year: 2021).*

[No Author Listed], addgene Sequence Analyzer: lentiGuide-Puro Sequencing Result. 2019. 1 page. Accessible at addgene.org/browse/sequence/331247.

[No Author Listed], *Homo sapiens* zinc finger CCCH-type containing 12A (ZC3H12A), transcript variant 1, mRNA. NCBI Reference Sequence: NM_025079.3. May 23, 2023. 5 pages.

[No Author Listed], Human Regl sgRNA designer. 2019. 1 page. Accessible through portals.broadinstitute.org/gpp/public/analysis-tools/sgrna-design.

[No Author Listed], Mouse Regl sgRNA sequence information. 2019. 1 page. Accessible through portals.broadinstitute.org/gpp/public/analysis-tools/sgrna-design.

[No Author Listed], NCBI ZC3H12A—zinc finger CCCH-type containing 12A : NCBI Orthologs. 2023. 4 pages. Accessible athttps://www.ncbi.nlm.nih.gov/gene/80149/ortholog/?scope=7776.

Basila et al., Minimal 2'-O-methyl phosphorothioate linkage modification pattern of synthetic guide RNAs for increased stability and efficient CRISPR-Cas9 gene editing avoiding cellular toxicity. PLoS One. Nov. 27, 2017;12(11):e0188593(20 pages).

Jinek et al., A programmable dual-RNA-guided DNA endonuclease in adaptive bacterial immunity. Science. Aug. 17, 2012;337(6096):816-21. Epub Jun. 28, 2012.

Safari et al., CRISPR Cpf1 proteins: structure, function and implications for genome editing. Cell Biosci. May 9, 2019;9:36(21 pages).

U.S. Appl. No. 17/098,212, filed Nov. 13, 2020, Yu et al.

U.S. Appl. No. 17/098,219, filed Nov. 13, 2020, Carson et al.

U.S. Appl. No. 17/483,100, filed Sep. 23, 2021, Dequeant et al.

U.S. Appl. No. 18/054,421, filed Nov. 10, 2022, Dequeant et al.

Dempsey, Regnase-1 in the TME. Nat Immunol. Feb. 2020;21(2):103.

Eyquem et al., Targeting a CAR to the TRAC locus with CRISPR/Cas9 enhances tumour rejection. Nature. Mar. 2, 2017;543(7643):113-117. Epub Feb. 22, 2017.

Heaton et al., Frontiers in antiviral therapy and immunotherapy. Clin Transl Immunology. Feb. 19, 2020;9(2):e1115.

Liu et al., CRISPR screen in mechanism and target discovery for cancer immunotherapy. Biochim Biophys Acta Rev Cancer. Aug. 2020;1874(1):188378(1-15). Epub May 13, 2020.

Liu et al., CRISPR-Cas9-mediated multiplex gene editing in CAR-T cells. Cell Res. Jan. 2017;27(1):154-157. Epub Dec. 2, 2016. Supplemental Information included. 10 pages total.

(56) References Cited

OTHER PUBLICATIONS

Oh et al., Monocyte chemotactic protein-induced protein-1 enhances DR5 degradation and negatively regulates DR5 activation-induced apoptosis through its deubiquitinase function. Oncogene. Jun. 2018;37(25):3415-3425. Epub Mar. 19, 2018.
Reina-Campos et al., Antitumour T cells stand the test of time. Nature. Dec. 11, 2019;576:392-3.
Ren et al., Multiplex Genome Editing to Generate Universal Car T Cells Resistant to PD1 Inhibition. Clin Cancer Res. May 1, 2017;23(9):2255-2266. Epub Nov. 4, 2016.
Roth, Editing of Endogenous Genes in Cellular Immunotherapies. Curr Hematol Malig Rep. Aug. 2020;15(4):235-240.
Tang et al., TGF-β inhibition via CRISPR promotes the long-term efficacy of CAR T cells against solid tumors. JCI Insight. Feb. 27, 2020;5(4):e133977(1-17).
Wei et al., Targeting REGNASE-1 programs long-lived effector T cells for cancer therapy. Nature. Dec. 11, 2019;576(7787):471-476. Supplemental Information included. 29 pages total.
Yoshinaga et al., Post-transcriptional control of immune responses and its potential application. Clin Transl Immunology. Jun. 17, 2019;8(6):e1063(1-13).
U.S. Appl. No. 17/493,253, filed Oct. 4, 2021, Dequeant et al.
U.S. Appl. No. 17/493,271, filed Oct. 4, 2021, Dequeant et al.

* cited by examiner

B2M
Indel%
100
80
60
40
20
0
Untreated
A0
A1
A2
A3
A4

TRAC
Indel%
100
80
60
40
20
0
Untreated
A0
A1
A2
A3
A4

Regnase-1
% Indels
100
80
60
40
20
0
Untreated
A0
A1
A2
A3
A4

TGFBRII
Indel %
100
80
60
40
20
0
UT
A0
A1
A2
A3
A4

FIG. 4

| Days | Materials | Process Step | Controls |
| --- | --- | --- | --- |
| day -x | Leukopheresis unit<br>Anti-CD4 Microbeads<br>Anti-CD8 Microbeads<br>PBS/EDTA Buffer with HSA | T Cell Enrichment | Cell count<br>Cell viability<br>T cell purity<br>Sterility |
| | Cryostor CS5 | T Cell Cryopreservation | Cell count<br>Cell viability |
| day 0 | Supplemented X-Vivo15<br>TransAct | T Cell Thawing, and Activation | Cell count<br>Cell viability |
| **day 2** | **Cas9 Nuclease**<br>**ZC3H12A-10 sgRNA**<br>**TGFBR2-5 sgRNA**<br>**Electroporation Buffer**<br>**Supplemented X-Vivo15** | **First Electroporation and Cell Recovery** | **Cell count**<br>**Cell viability** |
| day 4 | Cas9 Nuclease<br>TA-1 sgRNA<br>B2M-1 sgRNA<br>Electroporation Buffer<br>rAAV-138 Vector<br>Supplemented X-Vivo15 | Second Electroporation and Transduction | Cell count<br>Cell viability |
| **day 4-10/13** | Supplemented X-Vivo15 | Cell Expansion | Cell count<br>Cell viability<br>T Cell Purity |
| day 10/13 | Biotinylated TCRαβ Antibody<br>Anti-biotin Microbeads<br>PBS/EDTA buffer with HSA<br>Supplemented X-Vivo15 | TCRαβ Depletion and Cell Recovery | Cell count<br>Cell viability<br>%CAR Cells |
| day 11/14 | | Cell Culture Harvest<br>**(Drug Substance)** | Release testing |

TRAC
TRAC-%/CD45
100
90
80
60
40
20
0
UT
1X TA-1 1X Cas9
0.75X TA-1, 1X Cas9
0.5X TA-1, 1X Cas9
0.25X TA-1, 1X Cas9

CD70
TRAC-%/CD45
100
80
60
40
20
0
UT
1X TA-1 1X Cas9
0.75X TA-1, 1X Cas9
0.5X TA-1, 1X Cas9
0.25X TA-1, 1X Cas9

CAR+%
TRAC-%/CD45
100
80
60
40
20
0
UT
1X TA-1 1X Cas9
0.75X TA-1, 1X Cas9
0.5X TA-1, 1X Cas9
0.25X TA-1, 1X Cas9

B2M
B2M-%/CD45+
100
80
60
40
20
0
UT
1Reg1C
0.75Reg1C
0.5Reg1C
0.25Reg1C
0.125Reg1C
1Reg0.75C
1Reg0.5C
1Reg0.25C
1Reg0.125C

Regnase-1
Indel%
100
90
80
70
50
40
30
20
10
0
UT
1R1C
0.75R1C
0.5R1C
0.25R1C
0.125R1C
1R0.75C
1R0.5C
1R0.25C
1R0.125C

FIG. 8

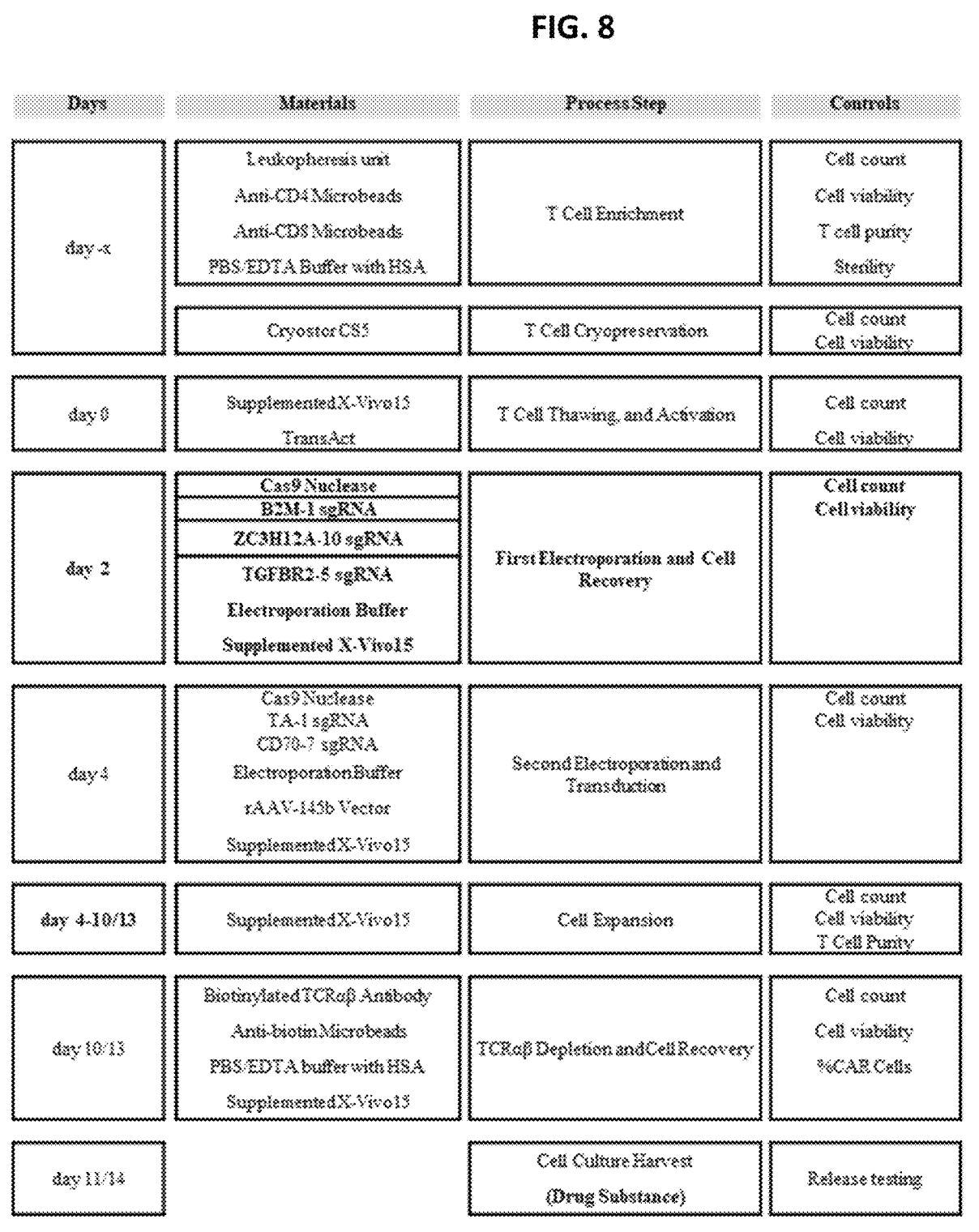

| Days | Materials | Process Step | Controls |
|---|---|---|---|
| day -x | Leukopheresis unit<br>Anti-CD4 Microbeads<br>Anti-CD8 Microbeads<br>PBS/EDTA Buffer with HSA | T Cell Enrichment | Cell count<br>Cell viability<br>T cell purity<br>Sterility |
| | Cryostor CS5 | T Cell Cryopreservation | Cell count<br>Cell viability |
| day 0 | Supplemented X-Vivo15<br>TransAct | T Cell Thawing, and Activation | Cell count<br>Cell viability |
| day 2 | Cas9 Nuclease<br>B2M-1 sgRNA<br>ZC3H12A-10 sgRNA<br>TGFBR2-5 sgRNA<br>Electroporation Buffer<br>Supplemented X-Vivo15 | First Electroporation and Cell Recovery | Cell count<br>Cell viability |
| day 4 | Cas9 Nuclease<br>TA-1 sgRNA<br>CD70-7 sgRNA<br>Electroporation Buffer<br>rAAV-145b Vector<br>Supplemented X-Vivo15 | Second Electroporation and Transduction | Cell count<br>Cell viability |
| day 4-10/13 | Supplemented X-Vivo15 | Cell Expansion | Cell count<br>Cell viability<br>T Cell Purity |
| day 10/13 | Biotinylated TCRαβ Antibody<br>Anti-biotin Microbeads<br>PBS/EDTA buffer with HSA<br>Supplemented X-Vivo15 | TCRαβ Depletion and Cell Recovery | Cell count<br>Cell viability<br>%CAR Cells |
| day 11/14 | | Cell Culture Harvest<br>(Drug Substance) | Release testing |

NALM6
(E:T 1:1)
% Lysis of target cells
0
10
20
30
40
50
60
70
80
90
100
EP Control
Control
Reference
Lot 4
Lot 5
Lot 6
Lot 7
Lot 8

NALM6
(E:T 0.5:1)
% Lysis of target cells
0
10
20
30
40
50
60
70
80
90
100
EP Control
Control
Reference
Lot 4
Lot 5
Lot 6
Lot 7
Lot 8

SEQUENCE LISTING

```
Sequence total quantity: 93
SEQ ID NO: 1            moltype = AA  length = 1368
FEATURE                 Location/Qualifiers
source                  1..1368
                        mol_type = protein
                        organism = synthetic construct
SEQUENCE: 1
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
```

```
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 2           moltype = RNA  length = 100
FEATURE                Location/Qualifiers
source                 1..100
                       mol_type = other RNA
                       organism = synthetic construct
misc_feature           1..4
                       note = modified with 2'-O-methylphosphorothioate
misc_feature           97..100
                       note = modified with 2'-O-methylphosphorothioate
SEQUENCE: 2
acgacgcgtg ggtggcaagc gttttagagc tagaaatagc aagttaaaat aaggctagtc  60
cgttatcaac ttgaaaaagt ggcaccgagt cggtgctttt                        100

SEQ ID NO: 3           moltype = RNA  length = 100
FEATURE                Location/Qualifiers
source                 1..100
                       mol_type = other RNA
                       organism = synthetic construct
SEQUENCE: 3
acgacgcgtg ggtggcaagc gttttagagc tagaaatagc aagttaaaat aaggctagtc  60
cgttatcaac ttgaaaaagt ggcaccgagt cggtgctttt                        100

SEQ ID NO: 4           moltype = RNA  length = 20
FEATURE                Location/Qualifiers
source                 1..20
                       mol_type = other RNA
                       organism = synthetic construct
misc_feature           1..4
                       note = modified with 2'-O-methylphosphorothioate
SEQUENCE: 4
acgacgcgtg ggtggcaagc                                              20

SEQ ID NO: 5           moltype = RNA  length = 20
FEATURE                Location/Qualifiers
source                 1..20
                       mol_type = other RNA
                       organism = synthetic construct
SEQUENCE: 5
acgacgcgtg ggtggcaagc                                              20

SEQ ID NO: 6           moltype = RNA  length = 103
FEATURE                Location/Qualifiers
source                 1..103
                       mol_type = other RNA
                       organism = synthetic construct
misc_feature           1..4
                       note = modified with 2'-O-methylphosphorothioate
misc_feature           99..103
                       note = modified with 2'-O-methylphosphorothioate
SEQUENCE: 6
cccctaccat gactttattc tgggttttag agctagaaat agcaagttaa aataaggcta  60
gtccgttatc aacttgaaaa agtggcaccg agtcggtgct ttt                    103

SEQ ID NO: 7           moltype = RNA  length = 103
FEATURE                Location/Qualifiers
source                 1..103
                       mol_type = other RNA
                       organism = synthetic construct
SEQUENCE: 7
cccctaccat gactttattc tgggttttag agctagaaat agcaagttaa aataaggcta  60
gtccgttatc aacttgaaaa agtggcaccg agtcggtgct ttt                    103

SEQ ID NO: 8           moltype = RNA  length = 23
FEATURE                Location/Qualifiers
source                 1..23
```

```
                         mol_type = other RNA
                         organism = synthetic construct
misc_feature             1..4
                         note = modified with 2'-O-methylphosphorothioate
SEQUENCE: 8
cccctaccat gactttattc tgg                                             23

SEQ ID NO: 9             moltype = RNA  length = 23
FEATURE                  Location/Qualifiers
source                   1..23
                         mol_type = other RNA
                         organism = synthetic construct
SEQUENCE: 9
cccctaccat gactttattc tgg                                             23

SEQ ID NO: 10            moltype = RNA  length = 100
FEATURE                  Location/Qualifiers
source                   1..100
                         mol_type = other RNA
                         organism = synthetic construct
misc_feature             1..4
                         note = modified with 2'-O-methylphosphorothioate
misc_feature             97..100
                         note = modified with 2'-O-methylphosphorothioate
SEQUENCE: 10
agagcaacag tgctgtggcc gttttagagc tagaaatagc aagttaaaat aaggctagtc  60
cgttatcaac ttgaaaaagt ggcaccgagt cggtgctttt                          100

SEQ ID NO: 11            moltype = RNA  length = 100
FEATURE                  Location/Qualifiers
source                   1..100
                         mol_type = other RNA
                         organism = synthetic construct
SEQUENCE: 11
agagcaacag tgctgtggcc gttttagagc tagaaatagc aagttaaaat aaggctagtc  60
cgttatcaac ttgaaaaagt ggcaccgagt cggtgctttt                          100

SEQ ID NO: 12            moltype = RNA  length = 20
FEATURE                  Location/Qualifiers
source                   1..20
                         mol_type = other RNA
                         organism = synthetic construct
misc_feature             1..4
                         note = modified with 2'-O-methylphosphorothioate
SEQUENCE: 12
agagcaacag tgctgtggcc                                                 20

SEQ ID NO: 13            moltype = RNA  length = 20
FEATURE                  Location/Qualifiers
source                   1..20
                         mol_type = other RNA
                         organism = synthetic construct
SEQUENCE: 13
agagcaacag tgctgtggcc                                                 20

SEQ ID NO: 14            moltype = RNA  length = 100
FEATURE                  Location/Qualifiers
source                   1..100
                         mol_type = other RNA
                         organism = synthetic construct
misc_feature             1..4
                         note = modified with 2'-O-methylphosphorothioate
misc_feature             97..100
                         note = modified with 2'-O-methylphosphorothioate
SEQUENCE: 14
gctactctct ctttctggcc gttttagagc tagaaatagc aagttaaaat aaggctagtc  60
cgttatcaac ttgaaaaagt ggcaccgagt cggtgctttt                          100

SEQ ID NO: 15            moltype = RNA  length = 100
FEATURE                  Location/Qualifiers
source                   1..100
                         mol_type = other RNA
                         organism = synthetic construct
SEQUENCE: 15
gctactctct ctttctggcc gttttagagc tagaaatagc aagttaaaat aaggctagtc  60
cgttatcaac ttgaaaaagt ggcaccgagt cggtgctttt                          100

SEQ ID NO: 16            moltype = RNA  length = 20
FEATURE                  Location/Qualifiers
```

```
source                  1..20
                        mol_type = other RNA
                        organism = synthetic construct
misc_feature            1..4
                        note = modified with 2'-O-methylphosphorothioate
SEQUENCE: 16
gctactctct ctttctggcc                                            20

SEQ ID NO: 17           moltype = RNA  length = 20
FEATURE                 Location/Qualifiers
source                  1..20
                        mol_type = other RNA
                        organism = synthetic construct
SEQUENCE: 17
gctactctct ctttctggcc                                            20

SEQ ID NO: 18           moltype = RNA  length = 100
FEATURE                 Location/Qualifiers
source                  1..100
                        mol_type = other RNA
                        organism = synthetic construct
misc_feature            1..4
                        note = modified with 2'-O-methylphosphorothioate
misc_feature            97..100
                        note = modified with 2'-O-methylphosphorothioate
SEQUENCE: 18
gctttggtcc cattggtcgc gttttagagc tagaaatagc aagttaaaat aaggctagtc  60
cgttatcaac ttgaaaaagt ggcaccgagt cggtgctttt                        100

SEQ ID NO: 19           moltype = RNA  length = 100
FEATURE                 Location/Qualifiers
source                  1..100
                        mol_type = other RNA
                        organism = synthetic construct
SEQUENCE: 19
gctttggtcc cattggtcgc gttttagagc tagaaatagc aagttaaaat aaggctagtc  60
cgttatcaac ttgaaaaagt ggcaccgagt cggtgctttt                        100

SEQ ID NO: 20           moltype = RNA  length = 20
FEATURE                 Location/Qualifiers
source                  1..20
                        mol_type = other RNA
                        organism = synthetic construct
misc_feature            1..4
                        note = modified with 2'-O-methylphosphorothioate
SEQUENCE: 20
gctttggtcc cattggtcgc                                            20

SEQ ID NO: 21           moltype = RNA  length = 20
FEATURE                 Location/Qualifiers
source                  1..20
                        mol_type = other RNA
                        organism = synthetic construct
SEQUENCE: 21
gctttggtcc cattggtcgc                                            20

SEQ ID NO: 22           moltype = DNA  length = 23
FEATURE                 Location/Qualifiers
source                  1..23
                        mol_type = other DNA
                        organism = synthetic construct
SEQUENCE: 22
acgacgcgtg ggtggcaagc ggg                                        23

SEQ ID NO: 23           moltype = DNA  length = 20
FEATURE                 Location/Qualifiers
source                  1..20
                        mol_type = other DNA
                        organism = synthetic construct
SEQUENCE: 23
acgacgcgtg ggtggcaagc                                            20

SEQ ID NO: 24           moltype = DNA  length = 26
FEATURE                 Location/Qualifiers
source                  1..26
                        mol_type = other DNA
                        organism = synthetic construct
SEQUENCE: 24
cccctaccat gactttattc tggtgg                                     26
```

```
SEQ ID NO: 25           moltype = DNA  length = 23
FEATURE                 Location/Qualifiers
source                  1..23
                        mol_type = other DNA
                        organism = synthetic construct
SEQUENCE: 25
cccctaccat gactttattc tgg                                         23

SEQ ID NO: 26           moltype = DNA  length = 23
FEATURE                 Location/Qualifiers
source                  1..23
                        mol_type = other DNA
                        organism = synthetic construct
SEQUENCE: 26
agagcaacag tgctgtggcc tgg                                         23

SEQ ID NO: 27           moltype = DNA  length = 20
FEATURE                 Location/Qualifiers
source                  1..20
                        mol_type = other DNA
                        organism = synthetic construct
SEQUENCE: 27
agagcaacag tgctgtggcc                                             20

SEQ ID NO: 28           moltype = DNA  length = 23
FEATURE                 Location/Qualifiers
source                  1..23
                        mol_type = other DNA
                        organism = synthetic construct
SEQUENCE: 28
gctactctct ctttctggcc tgg                                         23

SEQ ID NO: 29           moltype = DNA  length = 20
FEATURE                 Location/Qualifiers
source                  1..20
                        mol_type = other DNA
                        organism = synthetic construct
SEQUENCE: 29
gctactctct ctttctggcc                                             20

SEQ ID NO: 30           moltype = DNA  length = 23
FEATURE                 Location/Qualifiers
source                  1..23
                        mol_type = other DNA
                        organism = synthetic construct
SEQUENCE: 30
gctttggtcc cattggtcgc ggg                                         23

SEQ ID NO: 31           moltype = DNA  length = 20
FEATURE                 Location/Qualifiers
source                  1..20
                        mol_type = other DNA
                        organism = synthetic construct
SEQUENCE: 31
gctttggtcc cattggtcgc                                             20

SEQ ID NO: 32           moltype = RNA  length = 100
FEATURE                 Location/Qualifiers
source                  1..100
                        mol_type = other RNA
                        organism = synthetic construct
SEQUENCE: 32
nnnnnnnnnn nnnnnnnnnn gttttagagc tagaaatagc aagttaaaat aaggctagtc  60
cgttatcaac ttgaaaaagt ggcaccgagt cggtgctttt                        100

SEQ ID NO: 33           moltype = RNA  length = 96
FEATURE                 Location/Qualifiers
source                  1..96
                        mol_type = other RNA
                        organism = synthetic construct
SEQUENCE: 33
nnnnnnnnnn nnnnnnnnnn gttttagagc tagaaatagc aagttaaaat aaggctagtc  60
cgttatcaac ttgaaaaagt ggcaccgagt cggtgc                            96

SEQ ID NO: 34           moltype = RNA  length = 114
FEATURE                 Location/Qualifiers
source                  1..114
                        mol_type = other RNA
```

```
                         organism = synthetic construct
misc_feature             17..30
                         note = may be absent
misc_feature             108..114
                         note = uracil or absent
SEQUENCE: 34
nnnnnnnnnn nnnnnnnnnn nnnnnnnnnn gttttagagc tagaaatagc aagttaaaat  60
aaggctagtc cgttatcaac ttgaaaaagt ggcaccgagt cggtgctttt tttt        114

SEQ ID NO: 35            moltype = DNA  length = 19
FEATURE                  Location/Qualifiers
source                   1..19
                         mol_type = other DNA
                         organism = synthetic construct
SEQUENCE: 35
aagagcaaca aatctgact                                               19

SEQ ID NO: 36            moltype = DNA  length = 39
FEATURE                  Location/Qualifiers
source                   1..39
                         mol_type = other DNA
                         organism = synthetic construct
SEQUENCE: 36
aagagcaaca gtgctgtgcc tggagcaaca aatctgact                         39

SEQ ID NO: 37            moltype = DNA  length = 33
FEATURE                  Location/Qualifiers
source                   1..33
                         mol_type = other DNA
                         organism = synthetic construct
SEQUENCE: 37
aagagcaaca gtgctggagc aacaaatctg act                               33

SEQ ID NO: 38            moltype = DNA  length = 34
FEATURE                  Location/Qualifiers
source                   1..34
                         mol_type = other DNA
                         organism = synthetic construct
SEQUENCE: 38
aagagcaaca gtgcctggag caacaaatct gact                              34

SEQ ID NO: 39            moltype = DNA  length = 19
FEATURE                  Location/Qualifiers
source                   1..19
                         mol_type = other DNA
                         organism = synthetic construct
SEQUENCE: 39
aagagcaaca gtgctgact                                               19

SEQ ID NO: 40            moltype = DNA  length = 41
FEATURE                  Location/Qualifiers
source                   1..41
                         mol_type = other DNA
                         organism = synthetic construct
SEQUENCE: 40
aagagcaaca gtgctgtggg cctggagcaa caaatctgac t                      41

SEQ ID NO: 41            moltype = DNA  length = 38
FEATURE                  Location/Qualifiers
source                   1..38
                         mol_type = other DNA
                         organism = synthetic construct
SEQUENCE: 41
aagagcaaca gtgctggcct ggagcaacaa atctgact                          38

SEQ ID NO: 42            moltype = DNA  length = 41
FEATURE                  Location/Qualifiers
source                   1..41
                         mol_type = other DNA
                         organism = synthetic construct
SEQUENCE: 42
aagagcaaca gtgctgtgtg cctggagcaa caaatctgac t                      41

SEQ ID NO: 43            moltype = DNA  length = 79
FEATURE                  Location/Qualifiers
source                   1..79
                         mol_type = other DNA
                         organism = synthetic construct
SEQUENCE: 43
```

```
cgtggcctta gctgtgctcg cgctactctc tctttctgcc tggaggctat ccagcgtgag  60
tctctcctac cctcccgct                                               79

SEQ ID NO: 44          moltype = DNA  length = 78
FEATURE                Location/Qualifiers
source                 1..78
                       mol_type = other DNA
                       organism = synthetic construct
SEQUENCE: 44
cgtggcctta gctgtgctcg cgctactctc tctttcgcct ggaggctatc cagcgtgagt  60
ctctcctacc ctcccgct                                                78

SEQ ID NO: 45          moltype = DNA  length = 75
FEATURE                Location/Qualifiers
source                 1..75
                       mol_type = other DNA
                       organism = synthetic construct
SEQUENCE: 45
cgtggcctta gctgtgctcg cgctactctc tctttctgga ggctatccag cgtgagtctc  60
tcctaccctc ccgct                                                   75

SEQ ID NO: 46          moltype = DNA  length = 84
FEATURE                Location/Qualifiers
source                 1..84
                       mol_type = other DNA
                       organism = synthetic construct
SEQUENCE: 46
cgtggcctta gctgtgctcg cgctactctc tctttctgga tagcctggag gctatccagc  60
gtgagtctct cctaccctcc cgct                                         84

SEQ ID NO: 47          moltype = DNA  length = 55
FEATURE                Location/Qualifiers
source                 1..55
                       mol_type = other DNA
                       organism = synthetic construct
SEQUENCE: 47
cgtggcctta gctgtgctcg cgctatccag cgtgagtctc tcctaccctc ccgct       55

SEQ ID NO: 48          moltype = DNA  length = 82
FEATURE                Location/Qualifiers
source                 1..82
                       mol_type = other DNA
                       organism = synthetic construct
SEQUENCE: 48
cgtggcctta gctgtgctcg cgctactctc tctttctgtg gcctggaggc tatccagcgt  60
gagtctctcc taccctcccg ct                                           82

SEQ ID NO: 49          moltype = DNA  length = 58
FEATURE                Location/Qualifiers
source                 1..58
                       mol_type = other DNA
                       organism = synthetic construct
SEQUENCE: 49
cacaccacga ggcagatcac caagcccgcg caatgggacc aaagcagccc gcaggacg    58

SEQ ID NO: 50          moltype = DNA  length = 61
FEATURE                Location/Qualifiers
source                 1..61
                       mol_type = other DNA
                       organism = synthetic construct
SEQUENCE: 50
cacaccacga ggcagatcac caagcccgcg aaccaatggg accaaagcag cccgcaggac  60
g                                                                  61

SEQ ID NO: 51          moltype = DNA  length = 48
FEATURE                Location/Qualifiers
source                 1..48
                       mol_type = other DNA
                       organism = synthetic construct
SEQUENCE: 51
cacaccacga ggcagatcac caatgggacc aaagcagccc gcaggacg               48

SEQ ID NO: 52          moltype = DNA  length = 59
FEATURE                Location/Qualifiers
source                 1..59
                       mol_type = other DNA
                       organism = synthetic construct
SEQUENCE: 52
cacaccacga ggcagatcac caagcccgcg ccaatgggac caaagcagcc cgcaggacg   59
```

```
SEQ ID NO: 53           moltype = DNA  length = 59
FEATURE                 Location/Qualifiers
source                  1..59
                        mol_type = other DNA
                        organism = synthetic construct
SEQUENCE: 53
cacaccacga ggcagatcac caagcccgca ccaatgggac caaagcagcc cgcaggacg   59

SEQ ID NO: 54           moltype = DNA  length = 35
FEATURE                 Location/Qualifiers
source                  1..35
                        mol_type = other DNA
                        organism = synthetic construct
SEQUENCE: 54
cacaccacga ggcagatcac caagcccgca ggacg                             35

SEQ ID NO: 55           moltype = DNA  length = 20
FEATURE                 Location/Qualifiers
source                  1..20
                        mol_type = other DNA
                        organism = synthetic construct
SEQUENCE: 55
gtgggtggca agcgggtggt                                              20

SEQ ID NO: 56           moltype = DNA  length = 21
FEATURE                 Location/Qualifiers
source                  1..21
                        mol_type = other DNA
                        organism = synthetic construct
SEQUENCE: 56
gtgggtggca aagcgggtgg t                                            21

SEQ ID NO: 57           moltype = DNA  length = 19
FEATURE                 Location/Qualifiers
source                  1..19
                        mol_type = other DNA
                        organism = synthetic construct
SEQUENCE: 57
gtgggtggca gcgggtggt                                               19

SEQ ID NO: 58           moltype = DNA  length = 21
FEATURE                 Location/Qualifiers
source                  1..21
                        mol_type = other DNA
                        organism = synthetic construct
SEQUENCE: 58
gtgggtggca tagcgggtgg t                                            21

SEQ ID NO: 59           moltype = DNA  length = 18
FEATURE                 Location/Qualifiers
source                  1..18
                        mol_type = other DNA
                        organism = synthetic construct
SEQUENCE: 59
gtgggtggag cgggtggt                                                18

SEQ ID NO: 60           moltype = AA  length = 23
FEATURE                 Location/Qualifiers
source                  1..23
                        mol_type = protein
                        organism = synthetic construct
SEQUENCE: 60
IYIWAPLAGT CGVLLLSLVI TLY                                          23

SEQ ID NO: 61           moltype = DNA  length = 120
FEATURE                 Location/Qualifiers
source                  1..120
                        mol_type = other DNA
                        organism = synthetic construct
SEQUENCE: 61
tcaaagcgga gtaggttgtt gcattccgat tacatgaata tgactcctcg ccggcctggg  60
ccgacaagaa aacattacca accctatgcc cccccacgag acttcgctgc gtacaggtcc  120

SEQ ID NO: 62           moltype = AA  length = 40
FEATURE                 Location/Qualifiers
source                  1..40
                        mol_type = protein
                        organism = synthetic construct
```

```
SEQUENCE: 62
SKRSRLLHSD YMNMTPRRPG PTRKHYQPYA PPRDFAAYRS                      40

SEQ ID NO: 63           moltype = DNA  length = 336
FEATURE                 Location/Qualifiers
source                  1..336
                        mol_type = other DNA
                        organism = synthetic construct
SEQUENCE: 63
cgagtgaagt tttcccgaag cgcagacgct ccggcatatc agcaaggaca gaatcagctg  60
tataacgaac tgaatttggg acgccgcgag gagtatgacg tgcttgataa acgccggggg  120
agagacccgg aaatgggggg taaaccccga agaaagaatc cccaagaagg actctacaat  180
gaactccaga aggataagat ggcggaggcc tactcagaaa taggtatgaa gggcgaacga  240
cgacggggaa aaggtcacga tggcctctac caagggttga gtacggcaac caaagatacg  300
tacgatgcac tgcatatgca ggccctgcct cccaga                          336

SEQ ID NO: 64           moltype = AA  length = 112
FEATURE                 Location/Qualifiers
source                  1..112
                        mol_type = protein
                        organism = synthetic construct
SEQUENCE: 64
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR         112

SEQ ID NO: 65           moltype = AA  length = 120
FEATURE                 Location/Qualifiers
source                  1..120
                        mol_type = protein
                        organism = synthetic construct
SEQUENCE: 65
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 66           moltype = AA  length = 107
FEATURE                 Location/Qualifiers
source                  1..107
                        mol_type = protein
                        organism = synthetic construct
SEQUENCE: 66
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT              107

SEQ ID NO: 67           moltype = AA  length = 18
FEATURE                 Location/Qualifiers
source                  1..18
                        mol_type = protein
                        organism = synthetic construct
SEQUENCE: 67
GSTSGSGKPG SGEGSTKG                                              18

SEQ ID NO: 68           moltype = DNA  length = 735
FEATURE                 Location/Qualifiers
source                  1..735
                        mol_type = other DNA
                        organism = synthetic construct
SEQUENCE: 68
gatattcaga tgactcagac caccagtagc ttgtctgcct cactgggaga ccgagtaaca  60
atctcctgca gggcaagtca agacattagc aaatacctca attggtacca gcagaagccc  120
gacggaacgg taaaactcct catctatcat acgtcaaggt tgcattccgg agtaccgtca  180
cgattttcag gttctgggag cggaactgac tattccttga ctatttcaaa cctcgagcag  240
gaggacattg cgacatattt ttgtcaacaa ggtaataccc tcccttacac tttcggagga  300
ggaaccaaac tcgaaattac cggtcccacc agtggctctg ggaagcctgg cagtggagaa  360
ggttccacta aaggcgaggt gaagctccag gagagcggcc ccggtctcgt tgcccccagt  420
caaagcctct ctgtaacgtg cacagtgagt ggtgtatcat tgcctgatta tggcgtctcc  480
tggataaggc agcccccgcg aaagggtctt gaatggcttg ggtaatatg gggctcagag  540
acaacgtatt ataactccgc tctcaaaagt cgcttgacga taataaaaga taactccaag  600
agtcaagttt tccttaaaat gaacagtttg cagactgacg ataccgctat atattattgt  660
gctaaacatt attactacgg cggtagttac gcgatggatt attgggggca ggggacttct  720
gtcacagtca gtagt                                                 735

SEQ ID NO: 69           moltype = AA  length = 245
FEATURE                 Location/Qualifiers
source                  1..245
                        mol_type = protein
                        organism = synthetic construct
SEQUENCE: 69
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
```

```
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSS                                                              245

SEQ ID NO: 70          moltype = DNA  length = 1518
FEATURE                Location/Qualifiers
source                 1..1518
                       mol_type = other DNA
                       organism = synthetic construct
SEQUENCE: 70
atgcttcttt tggttacgtc tctgttgctt tgcgaacttc ctcatccagc gttcttgctg  60
atccccgata ttcagatgac tcagaccacc agtagcttgt ctgcctcact gggagaccga  120
gtaacaatct cctgcagggc aagtcaagac attagcaaat acctcaattg gtaccagcag  180
aagcccgacg gaacggtaaa actcctcatc tatcatacgt caaggttgca ttccggagta  240
ccgtcacgat tttcaggttc tgggagcgga actgactatt ccttgactat ttcaaacctc  300
gagcaggagg acattgcgac atatttttgt caacaaggta ataccctccc ttacactttc  360
ggaggaggaa ccaaactcga aattaccggg tccaccagtg gctctgggaa gcctggcagt  420
ggagaaggtt ccactaaagg cgaggtgaag ctccaggaga gcggccccgg tctcgttgcc  480
cccagtcaaa gcctctctgt aacgtgcaca gtgagtggtg tatcattgcc tgattatggc  540
gtctcctgga taaggcagcc cccgcgaaag ggtcttgaat ggcttggggt aatatggggc  600
tcagagacaa cgtattataa ctccgctctc aaaagtcgct tgacgataat aaaagataac  660
tccaagagtc aagttttcct taaaatgaac agtttgcaga ctgacgatac cgctatatat  720
tattgtgcta aacattatta ctacggcggt agttacgcga tggattattg gggcaggggg  780
acttctgtca cagtcagtag tgctgctgcc tttgtcccgg tatttctccc agccaaaccg  840
accacgactc ccgccccgcg ccctccgaca cccgctccca ccatcgcctc tcaacctctt  900
agtcttcgcc ccgaggcatg ccgacccgcc gccgggggtg ctgttcatac gaggggcttg  960
gacttcgctt gtgatattta catttgggct ccgttggcgg gtacgtgcgg cgtccttttg  1020
ttgtcactcg ttattacttt gtattgtaat cacaggaatc gctcaaagcg gagtaggttg  1080
ttgcattccg attacatgaa tatgactcct cgccggcctg ggccgacaag aaaacattac  1140
caaccctatg cccccccacg agacttcgct gcgtacaggt cccgagtgaa gttttcccga  1200
agcgcagacg ctccggcata tcagcaagga cagaatcagc tgtataacga actgaatttg  1260
ggacgccgcg aggagtatga cgtgcttgat aaacgccggg ggagagaccc ggaaatgggg  1320
ggtaaacccc gaagaaagaa tccccaagaa ggactctaca atgaactcca gaaggataag  1380
atggcggagg cctactcaga aataggtatg aagggcgaac gacgacgggg aaaaggtcac  1440
gatggcctct accaagggtt gagtacggca accaaagata cgtacgatgc actgcatatg  1500
caggccctgc ctcccaga                                                1518

SEQ ID NO: 71          moltype = AA  length = 506
FEATURE                Location/Qualifiers
source                 1..506
                       mol_type = protein
                       organism = synthetic construct
SEQUENCE: 71
MLLLVTSLLL CELPHPAFLL IPDIQMTQTT SSLSASLGDR VTISCRASQD ISKYLNWYQQ  60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSAAA FVPVFLPAKP TTTPAPRPPT PAPTIASQPL  300
SLRPEACRPA AGGAVHTRGL DFACDIYIWA PLAGTCGVLL LSLVITLYCN HRNRSKRSRL  360
LHSDYMNMTP RRPGPTRKHY QPYAPPRDFA AYRSRVKFSR SADAPAYQQG QNQLYNELNL  420
GRREEYDVLD KRRGRDPEMG GKPRRKNPQE GLYNELQKDK MAEAYSEIGM KGERRRGKGH  480
DGLYQGLSTA TKDTYDALHM QALPPR                                       506

SEQ ID NO: 72          moltype = AA  length = 118
FEATURE                Location/Qualifiers
source                 1..118
                       mol_type = protein
                       organism = synthetic construct
SEQUENCE: 72
QVQLVQSGAE VKKPGASVKV SCKASGYTFT NYGMNWVRQA PGQGLKWMGW INTYTGEPTY  60
ADAFKGRVTM TRDTSISTAY MELSRLRSDD TAVYYCARDY GDYGMDYWGQ GTTVTVSS    118

SEQ ID NO: 73          moltype = AA  length = 111
FEATURE                Location/Qualifiers
source                 1..111
                       mol_type = protein
                       organism = synthetic construct
SEQUENCE: 73
DIVMTQSPDS LAVSLGERAT INCRASKSVS TSGYSFMHWY QQKPGQPPKL LIYLASNLES  60
GVPDRFSGSG SGTDFTLTIS SLQAEDVAVY YCQHSREVPW TFGQGTKVEI K            111

SEQ ID NO: 74          moltype = AA  length = 16
FEATURE                Location/Qualifiers
source                 1..16
                       mol_type = protein
                       organism = synthetic construct
SEQUENCE: 74
GGGGSGGGGS GGGGSG                                                  16
```

-continued

```
SEQ ID NO: 75          moltype = DNA  length = 735
FEATURE                Location/Qualifiers
source                 1..735
                       mol_type = other DNA
                       organism = synthetic construct
SEQUENCE: 75
caggtccagt tggtgcaaag cggggcggag gtgaaaaaac ccggcgcttc cgtgaaggtg  60
tcctgtaagg cgtccggtta tacgttcacg aactacggga tgaattgggt tcgccaagcg  120
ccggggcagg gactgaaatg gatggggtgg ataaatacct acaccggcga acctacatac  180
gccgacgctt ttaaagggcg agtcactatg acgcgcgata ccagcatatc caccgcatac  240
atggagctgt cccgactccg gtcagacgac acggctgtct actattgtgc tcgggactat  300
ggcgattatg gcatggacta ctggggtcag ggtacgactg taacagttag tagtggtgga  360
ggcggcagtg gcgggggggg aagcggagga gggggttctg gtgacatagt tatgacccaa  420
tccccagata gtttggcggt ttctctgggc gagagggcaa cgattaattg tcgcgcatca  480
aagagcgttt caacgagcgg atattctttt atgcattggt accagcaaaa acccggacaa  540
ccgccgaagc tgctgatcta cttggcttca aatcttgagt ctggggtgcc ggaccgattt  600
tctggtagtg gaagcggaac tgactttacg ctcacgatca gttcactgca ggctgaggat  660
gtagcggtct attattgcca gcacagtaga gaagtcccct ggaccttcgg tcaaggcacg  720
aaagtagaaa ttaaa                                                    735

SEQ ID NO: 76          moltype = AA  length = 245
FEATURE                Location/Qualifiers
source                 1..245
                       mol_type = protein
                       organism = synthetic construct
SEQUENCE: 76
QVQLVQSGAE VKKPGASVKV SCKASGYTFT NYGMNWVRQA PGQGLKWMGW INTYTGEPTY  60
ADAFKGRVTM TRDTSISTAY MELSRLRSDD TAVYYCARDY GDYGMDYWGQ GTTVTVSSGG  120
GGSGGGGSGG GGSGDIVMTQ SPDSLAVSLG ERATINCRAS KSVSTSGYSF MHWYQQKPGQ  180
PPKLLIYLAS NLESGVPDRF SGSGSGTDFT LTISSLQAED VAVYYCQHSR EVPWTFGQGT  240
KVEIK                                                               245

SEQ ID NO: 77          moltype = DNA  length = 1527
FEATURE                Location/Qualifiers
source                 1..1527
                       mol_type = other DNA
                       organism = synthetic construct
SEQUENCE: 77
atggcgcttc cggtgacagc actgctcctc cccttggcgc tgttgctcca cgcagcaagg  60
ccgcaggtcc agttggtgca aagcggggcg gaggtgaaaa aacccggcgc ttccgtgaag  120
gtgtcctgta aggcgtccgg ttatacgttc acgaactacg ggatgaattg ggttcgccaa  180
gcgccggggc agggactgaa atggatgggg tggataaata cctacaccgg cgaacctaca  240
tacgccgacg cttttaaagg gcgagtcact atgacgcgcg ataccagcat atccaccgca  300
tacatggagc tgtcccgact ccggtcagac gacacggctg tctactattg tgctcgggac  360
tatggcgatt atggcatgga ctactggggt cagggtacga ctgtaacagt tagtagtggt  420
ggaggcggca gtggcggggg gggaagcgga ggagggggtt ctggtgacat agttatgacc  480
caatccccag atagtttggc ggtttctctg ggcgagaggg caacgattaa ttgtcgcgca  540
tcaaagagcg tttcaacgag cggatattct tttatgcatt ggtaccagca aaaacccgga  600
caaccgccga agctgctgat ctacttggct tcaaatcttg agtctggggt gccggaccga  660
ttttctggta gtggaagcgg aactgacttt acgctcacga tcagttcact gcaggctgag  720
gatgtagcgg tctattattg ccagcacagt agagaagtcc cctggacctt cggtcaaggc  780
acgaaagtag aaattaaaag tgctgctgcc tttgtcccgg tatttctccc agccaaaccg  840
accacgactc ccgccccgcg ccctccgaca cccgctccca ccatcgcctc tcaacctctt  900
agtcttcgcc ccgaggcatg ccgacccgcc gccgggggtg ctgttcatac gaggggcttg  960
gacttcgctt gtgatattta catttgggct ccgttggcgg gtacgtgcgg cgtccttttg  1020
ttgtcactcg ttattacttt gtattgtaat cacaggaatc gcaaacgggg cagaaagaaa  1080
ctcctgtata tattcaaaca accatttatg agaccagtac aaactactca agaggaagat  1140
ggctgtagct gccgatttcc agaagaagaa gaaggaggat gtgaactgcg agtgaagttt  1200
tcccgaagcg cagacgctcc ggcatatcag caaggacaga atcagctgta taacgaactg  1260
aatttgggac gccgcgagga gtatgacgtg cttgataaac gccgggggag agacccggaa  1320
atgggggggta aaccccgaag aaagaatccc caagaaggac tctacaatga actccagaag  1380
gataagatgg cggaggccta ctcagaaata ggtatgaagg gcgaacgacg acggggaaaa  1440
ggtcacgatg gcctctacca agggttgagt acggcaacca aagatacgta cgatgcactg  1500
catatgcagg ccctgcctcc cagataa                                       1527

SEQ ID NO: 78          moltype = AA  length = 508
FEATURE                Location/Qualifiers
source                 1..508
                       mol_type = protein
                       organism = synthetic construct
SEQUENCE: 78
MALPVTALLL PLALLLHAAR PQVQLVQSGA EVKKPGASVK VSCKASGYTF TNYGMNWVRQ  60
APGQGLKWMG WINTYTGEPT YADAFKGRVT MTRDTSISTA YMELSRLRSD DTAVYYCARD  120
YGDYGMDYWG QGTTVTVSSG GGGSGGGGSG GGGSGDIVMT QSPDSLAVSL GERATINCRA  180
SKSVSTSGYS FMHWYQQKPG QPPKLLIYLA SNLESGVPDR FSGSGSGTDF TLTISSLQAE  240
DVAVYYCQHS REVPWTFGQG TKVEIKSAAA FVPVFLPAKP TTTPAPRPPT PAPTIASQPL  300
SLRPEACRPA AGGAVHTRGL DFACDIYIWA PLAGTCGVLL LSLVITLYCN HRNRKRGRKK  360
LLYIFKQPFM RPVQTTQEED GCSCRFPEEE EGGCELRVKF SRSADAPAYQ QGQNQLYNEL  420
NLGRREEYDV LDKRRGRDPE MGGKPRRKNP QEGLYNELQK DKMAEAYSEI GMKGERRRGK  480
```

```
GHDGLYQGLS TATKDTYDAL HMQALPPR                                  508

SEQ ID NO: 79          moltype = DNA  length = 66
FEATURE                Location/Qualifiers
source                 1..66
                       mol_type = other DNA
                       organism = synthetic construct
SEQUENCE: 79
atgcttcttt tggttacgtc tctgttgctt tgcgaacttc ctcatccagc gttcttgctg  60
atcccc                                                             66

SEQ ID NO: 80          moltype = AA  length = 22
FEATURE                Location/Qualifiers
source                 1..22
                       mol_type = protein
                       organism = synthetic construct
SEQUENCE: 80
MLLLVTSLLL CELPHPAFLL IP                                           22

SEQ ID NO: 81          moltype = DNA  length = 261
FEATURE                Location/Qualifiers
source                 1..261
                       mol_type = other DNA
                       organism = synthetic construct
SEQUENCE: 81
gctgctgcct ttgtcccggt atttctccca gccaaaccga ccacgactcc cgccccgcgc  60
cctccgacac ccgctcccac catcgcctct caacctctta gtcttcgccc cgaggcatgc  120
cgacccgccg ccgggggtgc tgttcatacg aggggcttgg acttcgcttg tgatatttac  180
atttgggctc cgttggcggg tacgtgcggc gtccttttgt tgtcactcgt tattactttg  240
tattgtaatc acaggaatcg c                                            261

SEQ ID NO: 82          moltype = DNA  length = 252
FEATURE                Location/Qualifiers
source                 1..252
                       mol_type = other DNA
                       organism = synthetic construct
SEQUENCE: 82
tttgtcccgg tatttctccc agccaaaccg accacgactc ccgccccgcg ccctccgaca  60
cccgctccca ccatcgcctc tcaacctctt agtcttcgcc ccgaggcatg ccgacccgcc  120
gccgggggtg ctgttcatac gaggggcttg gacttcgctt gtgatattta catttgggct  180
ccgttggcgg gtacgtgcgg cgtccttttg ttgtcactcg ttattacttt gtattgtaat  240
cacaggaatc gc                                                      252

SEQ ID NO: 83          moltype = AA  length = 84
FEATURE                Location/Qualifiers
source                 1..84
                       mol_type = protein
                       organism = synthetic construct
SEQUENCE: 83
FVPVFLPAKP TTTPAPRPPT PAPTIASQPL SLRPEACRPA AGGAVHTRGL DFACDIYIWA  60
PLAGTCGVLL LSLVITLYCN HRNR                                         84

SEQ ID NO: 84          moltype = DNA  length = 145
FEATURE                Location/Qualifiers
source                 1..145
                       mol_type = other DNA
                       organism = synthetic construct
SEQUENCE: 84
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcct                                        145

SEQ ID NO: 85          moltype = DNA  length = 130
FEATURE                Location/Qualifiers
source                 1..130
                       mol_type = other DNA
                       organism = synthetic construct
SEQUENCE: 85
cctgcaggca gctgcgcgct cgctcgctca ctgaggccgc ccgggcgtcg ggcgaccttt  60
ggtcgcccgg cctcagtgag cgagcgagcg cgcagagagg gagtggccaa ctccatcact  120
aggggttcct                                                         130

SEQ ID NO: 86          moltype = DNA  length = 145
FEATURE                Location/Qualifiers
source                 1..145
                       mol_type = other DNA
                       organism = synthetic construct
SEQUENCE: 86
aggaacccct agtgatggag ttggccactc cctctctgcg cgctcgctcg ctcactgagg  60
```

```
ccgcccgggc aaagcccggg cgtcgggcga cctttggtcg cccggcctca gtgagcgagc  120
gagcgcgcag agagggagtg gccaa                                         145

SEQ ID NO: 87          moltype = DNA  length = 141
FEATURE                Location/Qualifiers
source                 1..141
                       mol_type = other DNA
                       organism = synthetic construct
SEQUENCE: 87
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ctgcctgcag g                                             141

SEQ ID NO: 88          moltype = DNA  length = 800
FEATURE                Location/Qualifiers
source                 1..800
                       mol_type = other DNA
                       organism = synthetic construct
SEQUENCE: 88
gagatgtaag gagctgctgt gacttgctca aggccttata tcgagtaaac ggtagtgctg  60
gggcttagac gcaggtgttc tgatttatag ttcaaaacct ctatcaatga gagagcaatc  120
tcctggtaat gtgatagatt tcccaactta atgccaacat accataaacc tcccattctg  180
ctaatgccca gcctaagttg gggagaccac tccagattcc aagatgtaca gtttgctttg  240
ctgggccttt ttcccatgcc tgcctttact ctgccagagt tatattgctg gggttttgaa  300
gaagatccta ttaaataaaa gaataagcag tattattaag tagccctgca tttcaggttt  360
ccttgagtgg caggccaggc ctggccgtga acgttcactg aaatcatggc ctcttggcca  420
agattgatag cttgtgcctg tccctgagtc ccagtccatc acgagcagct ggtttctaag  480
atgctatttc ccgtataaag catgagaccg tgacttgcca gccccacaga gccccgccct  540
tgtccatcac tggcatctgg actccagcct gggttggggc aaagagggaa atgagatcat  600
gtcctaaccc tgatcctctt gtcccacaga tatccagaac cctgaccctg ccgtgtacca  660
gctgagagac tctaaatcca gtgacaagtc tgtctgccta ttcaccgatt ttgattctca  720
aacaaatgtg tcacaaagta aggattctga tgtgtatatc acagacaaaa ctgtgctaga  780
catgaggtct atggacttca                                               800

SEQ ID NO: 89          moltype = DNA  length = 804
FEATURE                Location/Qualifiers
source                 1..804
                       mol_type = other DNA
                       organism = synthetic construct
SEQUENCE: 89
tggagcaaca aatctgactt tgcatgtgca aacgccttca acaacagcat tattccagaa  60
gacaccttct tccccagccc aggtaagggc agctttggtg ccttcgcagg ctgtttcctt  120
gcttcaggaa tggccaggtt ctgcccagag ctctggtcaa tgatgtctaa aactcctctg  180
attggtggtc tcggccttat ccattgccac caaaaccctc tttttactaa gaaacagtga  240
gccttgttct ggcagtccag agaatgacac gggaaaaaag cagatgaaga gaaggtggca  300
ggagagggca cgtggcccag cctcagtctc tccaactgag ttcctgcctg cctgcctttg  360
ctcagactgt ttgcccctta ctgctcttct aggcctcatt ctaagcccct tctccaagtt  420
gcctctcctt atttctccct gtctgccaaa aaatctttcc cagctcacta agtcagtctc  480
acgcagtcac tcattaaccc accaatcact gattgtgccg gcacatgaat gcaccaggtg  540
ttgaagtgga ggaattaaaa agtcagatga ggggtgtgcc cagaggaagc accattctag  600
ttgggggagc ccatctgtca gctgggaaaa gtccaaataa cttcagattg gaatgtgttt  660
taactcaggg ttgagaaaac agctaccttc aggacaaaag tcagggaagg gctctctgaa  720
gaaatgctac ttgaagatac cagccctacc aagggcaggg agaggaccct atagaggcct  780
gggacaggag ctcaatgaga aagg                                          804

SEQ ID NO: 90          moltype = DNA  length = 1178
FEATURE                Location/Qualifiers
source                 1..1178
                       mol_type = other DNA
                       organism = synthetic construct
SEQUENCE: 90
ggctccggtg cccgtcagtg ggcagagcgc acatcgccca cagtccccga gaagttgggg  60
ggaggggtcg gcaattgaac cggtgcctag agaaggtggc gcggggtaaa ctgggaaagt  120
gatgtcgtgt actggctccg cctttttccc gagggtgggg gagaaccgta tataagtgca  180
gtagtcgccg tgaacgttct ttttcgcaac gggtttgccg ccagaacaca ggtaagtgcc  240
gtgtgtggtt cccgcgggcc tggcctcttt acgggttatg gcccttgcgt gccttgaatt  300
acttccactg gctgcagtac gtgattcttg atcccgagct tcgggttgga agtgggtggg  360
agagttcgag gccttgcgct taaggagccc cttcgcctcg tgcttgagtt gaggcctggc  420
ctgggcgctg gggccgccgc gtgcgaatct ggtggcacct tcgcgcctgt ctcgctgctt  480
tcgataagtc tctagccatt taaaattttt gatgacctgc tgcgacgctt tttttctggc  540
aagatagtct tgtaaatgcg ggccaagatc tgcacactgg tatttcggtt tttggggccg  600
cgggcggcga cggggcccgt gcgtcccagc gcacatgttc ggcgaggcgg ggcctgcgag  660
cgcggccacc gagaatcgga cgggggtagt ctcaagctgg ccggcctgct ctggtgcctg  720
gcctcgcgcc gccgtgtatc gccccgccct gggcggcaag gctggcccgg tcggcaccag  780
ttgcgtgagc ggaaagatgg ccgcttcccg gccctgctgc agggagctca aaatggagga  840
cgcggcgctc gggagagcgg gcgggtgagt cacccacaca aaggaaaagg gcctttccgt  900
cctcagccgt cgcttcatgt gactccacgg agtaccgggc gccgtccagg cacctcgatt  960
agttctcgag cttttggagt acgtcgtctt taggttgggg ggaggggttt tatgcgatgg  1020
agtttcccca cactgagtgg gtggagactg aagttaggcc agcttggcac ttgatgtaat  1080
```

```
tctccttgga atttgccctt tttgagtttg gatcttggtt cattctcaag cctcagacag  1140
tggttcaaag ttttttcttt ccatttcagg tgtcgtga                           1178

SEQ ID NO: 91          moltype = DNA  length = 4358
FEATURE                Location/Qualifiers
source                 1..4358
                       mol_type = other DNA
                       organism = synthetic construct
SEQUENCE: 91
gagatgtaag gagctgctgt gacttgctca aggccttata tcgagtaaac ggtagtgctg  60
gggcttagac gcaggtgttc tgatttatag ttcaaaacct ctatcaatga gagagcaatc  120
tcctggtaat gtgatagatt tcccaactta atgccaacat accataaacc tcccattctg  180
ctaatgccca gcctaagttg gggagaccac tccagattcc aagatgtaca gtttgctttg  240
ctgggccttt ttcccatgcc tgcctttact ctgccagagt tatattgctg gggttttgaa  300
gaagatccta ttaaataaaa gaataagcag tattattaag tagccctgca tttcaggttt  360
ccttgagtgg caggccaggc ctggccgtga acgttcactg aaatcatggc ctcttggcca  420
agattgatag cttgtgcctg tccctgagtc ccagtccatc acgagcagct ggtttctaag  480
atgctatttc ccgtataaag catgagaccg tgacttgcca gccccacaga gccccgccct  540
tgtccatcac tggcatctgg actccagcct gggttggggc aaagagggaa atgagatcat  600
gtcctaaccc tgatcctctt gtcccacaga tatccagaac cctgaccctg ccgtgtacca  660
gctgagagac tctaaatcca gtgacaagtc tgtctgccta ttcaccgatt ttgattctca  720
aacaaatgtg tcacaaagta aggattctga tgtgtatatc acagacaaaa ctgtgctaga  780
catgaggtct atggacttca ggctccggtg cccgtcagtg ggcagagcgc acatcgccca  840
cagtccccga gaagttgggg ggaggggtcg gcaattgaac cggtgcctag agaaggtggc  900
gcggggtaaa ctgggaaagt gatgtcgtgt actggctccg cctttttccc gagggtgggg  960
gagaaccgta tataagtgca gtagtcgccg tgaacgttct ttttcgcaac gggtttgccg  1020
ccagaacaca ggtaagtgcc gtgtgtggtt cccgcgggcc tggcctcttt acgggttatg  1080
gcccttgcgt gccttgaatt acttccactg gctgcagtac gtgattcttg atcccgagct  1140
tcgggttgga agtgggtggg agagttcgag gccttgcgct taaggagccc cttcgcctcg  1200
tgcttgagtt gaggcctggc ctgggcgctg gggccgccgc gtgcgaatct ggtggcacct  1260
tcgcgcctgt ctcgctgctt tcgataagtc tctagccatt taaaattttt gatgacctgc  1320
tgcgacgctt tttttctggc aagatagtct tgtaaatgcg ggccaagatc tgcacactgg  1380
tatttcggtt tttggggccg cgggcggcga cggggcccgt gcgtcccagc gcacatgttc  1440
ggcgaggcgg ggcctgcgag cgcggccacc gagaatcgga cgggggtagt ctcaagctgg  1500
ccggcctgct ctggtgcctg gcctcgcgcc gccgtgtatc gccccgccct gggcggcaag  1560
gctggcccgg tcggcaccag ttgcgtgagc ggaaagatgg ccgcttcccg gccctgctgc  1620
agggagctca aaatggagga cgcggcgctc gggagagcgg gcgggtgagt cacccacaca  1680
aaggaaaagg gcctttccgt cctcagccgt cgcttcatgt gactccacgg agtaccgggc  1740
gccgtccagg cacctcgatt agttctcgag cttttggagt acgtcgtctt taggttgggg  1800
ggaggggttt tatgcgatgg agtttcccca cactgagtgg gtggagactg aagttaggcc  1860
agcttggcac ttgatgtaat tctccttgga atttgccctt tttgagtttg gatcttggtt  1920
cattctcaag cctcagacag tggttcaaag ttttttcttt ccatttcagg tgtcgtgacc  1980
accatgcttc ttttggttac gtctctgttg ctttgcgaac ttcctcatcc agcgttcttg  2040
ctgatccccg atattcagat gactcagacc accagtagct tgtctgcctc actgggagac  2100
cgagtaacaa tctcctgcag ggcaagtcaa gacattagca aatacctcaa ttggtaccag  2160
cagaagcccg acggaacggt aaaactcctc atctatcata cgtcaaggtt gcattccgga  2220
gtaccgtcac gattttcagg ttctgggagc ggaactgact attccttgac tatttcaaac  2280
ctcgagcagg aggacattgc gacatatttt tgtcaacaag gtaataccct cccttacact  2340
ttcggaggag gaaccaaact cgaaattacc gggtccacca gtggctctgg gaagcctggc  2400
agtggagaag gttccactaa aggcgaggtg aagctccagg agagcggccc cggtctcgtt  2460
gcccccagtc aaagcctctc tgtaacgtgc acagtgagtg gtgtatcatt gcctgattat  2520
ggcgtctcct ggataaggca gcccccgcga aagggtcttg aatggcttgg ggtaatatgg  2580
ggctcagaga caacgtatta taactccgct ctcaaaagtc gcttgacgat aataaaagat  2640
aactccaaga gtcaagtttt ccttaaaatg aacagtttgc agactgacga taccgctata  2700
tattattgtg ctaaacatta ttactacggc ggtagttacg cgatggatta ttgggggcag  2760
gggacttctg tcacagtcag tagtgctgct gcctttgtcc cggtatttct cccagccaaa  2820
ccgaccacga ctcccgcccc gcgccctccg acacccgctc ccaccatcgc ctctcaacct  2880
cttagtcttc gccccgaggc atgccgaccc gccgccgggg gtgctgttca tacgaggggc  2940
ttggacttcg cttgtgatat ttacatttgg gctccgttgg cgggtacgtg cggcgtcctt  3000
ttgttgtcac tcgttattac tttgtattgt aatcacagga atcgctcaaa gcggagtagg  3060
ttgttgcatt ccgattacat gaatatgact cctcgccggc ctgggccgac aagaaaacat  3120
taccaaccct atgccccccc acgagacttc gctgcgtaca ggtcccgagt gaagttttcc  3180
cgaagcgcag acgctccggc atatcagcaa ggacagaatc agctgtataa cgaactgaat  3240
ttgggacgcc gcgaggagta tgacgtgctt gataaacgcc gggggagaga cccggaaatg  3300
gggggtaaac cccgaagaaa gaatccccaa gaaggactct acaatgaact ccagaaggat  3360
aagatggcgg aggcctactc agaaataggt atgaagggcg aacgacgacg gggaaaaggt  3420
cacgatggcc tctaccaagg gttgagtacg gcaaccaaag atacgtacga tgcactgcat  3480
atgcaggccc tgcctcccag ataataataa aatcgctatc catcgaagat ggatgtgtgt  3540
tggttttttg tgtgtggagc aacaaatctg actttgcatg tgcaaacgcc ttcaacaaca  3600
gcattattcc agaagacacc ttcttcccca gcccaggtaa gggcagcttt ggtgccttcg  3660
caggctgttt ccttgcttca ggaatggcca ggttctgccc agagctctgg tcaatgatgt  3720
ctaaaactcc tctgattggt ggtctcggcc ttatccattg ccaccaaaac cctcttttta  3780
ctaagaaaca gtgagccttg ttctggcagt ccagagaatg acacgggaaa aaagcagatg  3840
aagagaaggt ggcaggagag ggcacgtggc ccagcctcag tctctccaac tgagttcctg  3900
cctgcctgcc tttgctcaga ctgtttgccc cttactgctc ttctaggcct cattctaagc  3960
cccttctcca agttgcctct ccttatttct ccctgtctgc caaaaaatct ttcccagctc  4020
actaagtcag tctcacgcag tcactcatta acccaccaat cactgattgt gccggcacat  4080
gaatgcacca ggtgttgaag tggaggaatt aaaaagtcag atgaggggtg tgcccagagg  4140
aagcaccatt ctagttgggg gagcccatct gtcagctggg aaaagtccaa ataacttcag  4200
```

```
attggaatgt gttttaactc agggttgaga aaacagctac cttcaggaca aaagtcaggg  4260
aagggctctc tgaagaaatg ctacttgaag ataccagccc taccaagggc agggagagga  4320
ccctatagag gcctgggaca ggagctcaat gagaaagg                          4358

SEQ ID NO: 92          moltype = DNA  length = 4364
FEATURE                Location/Qualifiers
source                 1..4364
                       mol_type = other DNA
                       organism = synthetic construct
SEQUENCE: 92
gagatgtaag gagctgctgt gacttgctca aggccttata tcgagtaaac ggtagtgctg  60
gggcttagac gcaggtgttc tgatttatag ttcaaaacct ctatcaatga gagagcaatc  120
tcctggtaat gtgatagatt tcccaactta atgccaacat accataaacc tcccattctg  180
ctaatgccca gcctaagttg gggagaccac tccagattcc aagatgtaca gtttgctttg  240
ctgggccttt ttcccatgcc tgcctttact ctgccagagt tatattgctg gggttttgaa  300
gaagatccta ttaaataaaa gaataagcag tattattaag tagccctgca tttcaggttt  360
ccttgagtgg caggccaggc ctggccgtga acgttcactg aaatcatggc ctcttggcca  420
agattgatag cttgtgcctg tccctgagtc ccagtccatc acgagcagct ggtttctaag  480
atgctatttc ccgtataaag catgagaccg tgacttgcca gccccacaga gccccgccct  540
tgtccatcac tggcatctgg actccagcct gggttggggc aaagagggaa atgagatcat  600
gtcctaaccc tgatcctctt gtcccacaga tatccagaac cctgaccctg ccgtgtacca  660
gctgagagac tctaaatcca gtgacaagtc tgtctgccta ttcaccgatt ttgattctca  720
aacaaatgtg tcacaaagta aggattctga tgtgtatatc acagacaaaa ctgtgctaga  780
catgaggtct atggacttca ggctccggtg cccgtcagtg ggcagagcgc acatcgccca  840
cagtccccga gaagttgggg ggaggggtcg gcaattgaac cggtgcctag agaaggtggc  900
gcggggtaaa ctgggaaagt gatgtcgtgt actggctccg cctttttccc gagggtgggg  960
gagaaccgta tataagtgca gtagtcgccg tgaacgttct ttttcgcaac gggtttgccg  1020
ccagaacaca ggtaagtgcc gtgtgtggtt cccgcgggcc tggcctcttt acgggttatg  1080
gcccttgcgt gccttgaatt acttccactg gctgcagtac gtgattcttg atcccgagct  1140
tcgggttgga agtgggtggg agagttcgag gccttgcgct taaggagccc cttcgcctcg  1200
tgcttgagtt gaggcctggc ctgggcgctg gggccgccgc gtgcgaatct ggtggcacct  1260
tcgcgcctgt ctcgctgctt tcgataagtc tctagccatt taaaattttt gatgacctgc  1320
tgcgacgctt tttttctggc aagatagtct tgtaaatgcg ggccaagatc tgcacactgg  1380
tatttcggtt tttggggccg cgggcggcga cggggcccgt gcgtcccagc gcacatgttc  1440
ggcgaggcgg ggcctgcgag cgcggccacc gagaatcgga cgggggtagt ctcaagctgg  1500
ccggcctgct ctggtgcctg gcctcgcgcc gccgtgtatc gccccgccct gggcggcaag  1560
gctggcccgg tcggcaccag ttgcgtgagc ggaaagatgg ccgcttcccg gccctgctgc  1620
agggagctca aaatggagga cgcggcgctc gggagagcgg gcgggtgagt cacccacaca  1680
aaggaaaagg gcctttccgt cctcagccgt cgcttcatgt gactccacgg agtaccgggc  1740
gccgtccagg cacctcgatt agttctcgag cttttggagt acgtcgtctt taggttgggg  1800
ggaggggttt tatgcgatgg agtttcccca cactgagtgg gtggagactg aagttaggcc  1860
agcttggcac ttgatgtaat tctccttgga atttgccctt tttgagtttg gatcttggtt  1920
cattctcaag cctcagacag tggttcaaag tttttttctt ccatttcagg tgtcgtgacc  1980
accatggcgc ttccggtgac agcactgctc ctccccttgg cgctgttgct ccacgcagca  2040
aggccgcagg tccagttggt gcaaagcggg gcggaggtga aaaaacccgg cgcttccgtg  2100
aaggtgtcct gtaaggcgtc cggttatacg ttcacgaact acgggatgaa ttgggttcgc  2160
caagcgccgg ggcagggact gaaatggatg ggtggataa atacctacac cggcgaacct  2220
acatacgccg acgcttttaa agggcgagtc actatgacgc gcgataccag catatccacc  2280
gcatacatgg agctgtcccg actccggtca gacgacacgg ctgtctacta ttgtgctcgg  2340
gactatggcg attatggcat ggactactgg ggtcagggta cgactgtaac agttagtagt  2400
ggtggaggcg gcagtggcgg ggggggaagc ggaggagggg gttctggtga catagttatg  2460
acccaatccc cagatagttt ggcggtttct ctgggcgaga gggcaacgat taattgtcgc  2520
gcatcaaaga gcgtttcaac gagcggatat tcttttatgc attggtacca gcaaaaaccc  2580
ggacaaccgc cgaagctgct gatctacttg gcttcaaatc ttgagtctgg ggtgccggac  2640
cgattttctg gtagtggaag cggaactgac tttacgctca cgatcagttc actgcaggct  2700
gaggatgtag cggtctatta ttgccagcac agtagagaag tcccctggac cttcggtcaa  2760
ggcacgaaag tagaaattaa aagtgctgct gcctttgtcc cggtatttct cccagccaaa  2820
ccgaccacga ctcccgcccc gcgccctccg acacccgctc ccaccatcgc ctctcaacct  2880
cttagtcttc gccccgaggc atgccgaccc gccgccgggg gtgctgttca tacgagggggc  2940
ttggacttcg cttgtgatat ttacatttgg gctccgttgg cgggtacgtg cggcgtcctt  3000
ttgttgtcac tcgttattac tttgtattgt aatcacagga atcgcaaacg gggcagaaag  3060
aaactcctgt atatattcaa acaaccattt atgagaccag tacaaactac tcaagaggaa  3120
gatggctgta gctgccgatt tccagaagaa gaagaaggag gatgtgaact gcgagtgaag  3180
ttttcccgaa gcgcagacgc tccggcatat cagcaaggac agaatcagct gtataacgaa  3240
ctgaatttgg gacgccgcga ggagtatgac gtgcttgata aacgccgggg gagagacccg  3300
gaaatggggg gtaaaccccg aagaaagaat ccccaagaag gactctacaa tgaactccag  3360
aaggataaga tggcggaggc ctactcagaa ataggtatga agggcgaacg acgacgggga  3420
aaaggtcacg atggcctcta ccaagggttg agtacggcaa ccaaagatac gtacgatgca  3480
ctgcatatgc aggccctgcc tcccagataa taaaaatc gctatccatc gaagatggat  3540
gtgtgttggt tttttgtgtg tggagcaaca aatctgactt tgcatgtgca aacgccttca  3600
acaacagcat tattccagaa gacaccttct tccccagccc aggtaagggc agctttggtg  3660
ccttcgcagg ctgtttcctt gcttcaggaa tggccaggtt ctgcccagag ctctggtcaa  3720
tgatgtctaa aactcctctg attggtggtc tcggccttat ccattgccac caaaaccctc  3780
tttttactaa gaaacagtga gccttgttct ggcagtccag agaatgacac gggaaaaaag  3840
cagatgaaga gaaggtggca ggagagggca cgtggcccag cctcagtctc tccaactgag  3900
ttcctgcctg cctgcctttg ctcagactgt ttgcccctta ctgctcttct aggcctcatt  3960
ctaagcccct tctccaagtt gcctctcctt atttctccct gtctgccaaa aaatctttcc  4020
cagctcacta agtcagtctc acgcagtcac tcattaaccc accaatcact gattgtgccg  4080
gcacatgaat gcaccaggtg ttgaagtgga ggaattaaaa agtcagatga ggggtgtgcc  4140
```

-continued

```
cagaggaagc accattctag ttgggggagc ccatctgtca gctgggaaaa gtccaaataa  4200
cttcagattg gaatgtgttt taactcaggg ttgagaaaac agctaccttc aggacaaaag  4260
tcagggaagg gctctctgaa gaaatgctac ttgaagatac cagccctacc aagggcaggg  4320
agaggaccct atagaggcct gggacaggag ctcaatgaga aagg                  4364

SEQ ID NO: 93          moltype = AA  length = 21
FEATURE                Location/Qualifiers
source                 1..21
                       mol_type = protein
                       organism = synthetic construct
SEQUENCE: 93
MALPVTALLL PLALLLHAAR P                                           21
```

METHODS FOR MANUFACTURING GENETICALLY ENGINEERED CAR-T CELLS

CROSS REFERENCE TO RELATED APPLICATIONS

This application claims the benefit of the filing dates of U.S. Provisional Application No. 63/225,762, filed Jul. 26, 2021, U.S. Provisional Application No. 63/241,801, filed Sep. 8, 2021, and U.S. Provisional Application No. 63/246,975, filed Sep. 22, 2021. The entire contents of each of these applications are incorporated by reference herein.

SEQUENCE LISTING

The instant application contains a Sequence Listing which has been filed electronically in XML format and is hereby incorporated by reference in its entirety. Said XML copy, created on Jul. 25, 2022, is named 095136-0696-051US1_SEQ.xml and is 111,987 bytes in size.

BACKGROUND

Chimeric antigen receptor (CAR) T-cell therapy has shown promising therapeutic effects in treating hematologic cancer. Typically, CAR-T cells are generated by genetic engineering of either patient immune cells (autologous) or immune cells from unrelated human donors (allogenic). Production of high-quality, clinical grade CAR-T cells is a prerequisite for the wide application of this technology. It is therefore of great interest to develop efficient manufacturing processes for large-scale production of CAR-T cells with improved therapeutic activities.

SUMMARY OF THE INVENTION

The present disclosure is based, at least in part, on the development of methods for manufacturing genetically engineered T cells expressing a chimeric antigen receptor (CAR), e.g., an anti-CD19 CAR, an anti-BCMA CAR, or an anti-CD70 CAR, and having one or more additional gene edits to improve CAR-T cell therapeutic activities and in vivo persistency. The manufacturing methods disclosed herein provide several advantages, for example, consistent and high editing efficiencies of target genes and/or low risk in translocation effects. The methods disclosed herein allows for production of a robust supply of clinically useful and advantageous CAR T-cell therapies.

Accordingly, some aspects of the present disclosure feature a method for manufacturing genetically engineered T cells, the method comprising: (i) providing a population of T cells, and (ii) delivering to the T cells: (a) one or more Cas9 enzymes; (b) a first guide RNA (gRNA) targeting a Regnase-1 (Reg1) gene; (c) a second gRNA targeting a Transforming Growth Factor Beta Receptor II (TGFBRII) gene; (d) a third gRNA targeting a target gene (e.g., a T cell receptor alpha chain constant region (TRAC) gene); (e) optionally, a fourth gRNA targeting a beta-2 microglobulin (β2M) gene; and (f) a donor template comprising a nucleic acid sequence encoding a chimeric antigen receptor flanked by a left homology arm and a right homology arm, wherein the left homology arm and the right homology arm are homologous to a locus in the target gene. Such a method can produce genetically engineered T cells comprising a disrupted target gene, optionally a disrupted TRAC gene, optionally a disrupted β2M gene, a disrupted Reg1 gene, a disrupted TGFBRII gene.

In some embodiments, the method may further comprise delivering to the T cells (g) a fifth gRNA targeting a CD70 gene, and wherein the genetically engineered T cells further comprises a disrupted CD70 gene.

In some embodiments, the nucleic acid sequence encoding the CAR may be inserted into the target gene. In some examples, the target gene is the TRAC gene. In some examples, the CAR may bind a tumor antigen. Examples include CD19, CD70, and BCMA.

In some instances, the population of T cells in step (i) comprises activated T cells. In some examples, the activated T cells may be produced by a process comprising: (i-a) incubating a T cell population in the presence of a T cell activating agent in a cell culture vessel to produce the population of activated T cells. In some examples, step (i-a) can be performed for about 24-72 hours, optionally for about 48 hours. In some examples, the T cell activating agent comprises a CD3 agonist and a CD28 agonist. In specific examples, the CD3 agonist and the CD28 agonist are attached to a nanomatrix particle.

In some instances, the T cell population in step (i) can be derived from cryopreserved T cells enriched from human blood cells. In some examples, the human blood cells can be obtained from one or more human donors. For example, the T cell population is prepared by a process comprising: (i-a-1) obtaining blood cells from one or more human donors, (i-a-2) enriching $CD4^+$T cells, $CD8^+$ T cells, or both from the blood cells, and optionally (i-a-3) freezing the enriched T cells from step (i-a-2).

In some embodiments, (a)-(d), and optionally (e) and/or (g) in step (ii) are delivered to the activated T cells by one or more electroporation events. For example, the gRNAs of (b)-(d) and optionally (e) and/or (g) form one or more ribonucleoprotein (RNP) complexes with the one or more Cas9 enzyme of (a). Alternatively or in addition, the donor template is in an adeno-associated viral (AAV) vector.

In some instances, the delivering step (ii) is performed by:

(ii-a) performing a first electroporation to the activated T cells to introduce a first gene editing system to produce a first population of genetically engineered T cells;

(ii-b) culturing the first population of genetically engineered T cells in a medium for T cell recovery, (ii-c) performing a second electroporation to introduce a second gene editing system to the recovered T cells from step (ii-b) to produce a second population of genetically engineered T cells; and (ii-d) incubating the second population of genetically engineered T cells with recombinant AAV particles, which comprise the donor template of (f) to produce the genetically engineered T cells.

The first gene editing system and the second gene editing system collectively comprise the one or more Cas9 enzymes of (a) and the gRNAs of (b)-(d) and optionally (e) and/or (g).

In some examples, the first gene editing system in step (ii-a) comprises one of the Cas9 enzyme(s), the first gRNA that targets the Reg1 gene, and the second gRNA that targets the TGFBRII gene. For example, the Cas9 enzyme and the first and/or the second gRNAs may form an RNP complex. In some instances, the Cas9 enzyme and the first gRNA that targets the Reg1 gene are at a weight ratio of 4:1 to 1:4, e.g., 2:1 to 1:2. Alternatively or in addition, the Cas9 enzyme and the second gRNA that targets the TGFBRII gene are at a weight ratio of 4:1 to 1:4, e.g., 2:1 to 1:2.

In some instances, the first gene editing system in step (ii-a) further comprises the fourth gRNA that targets the β2M gene.

In step (ii-a), the activated T cells may have a concentration of about $1\times10^8$ cells/ml to about $5\times10^8$ cells/ml. In some examples, the activated T cells may have a concentration of about $3\times10^8$ cells/ml. In some examples, the Cas9 enzyme has a concentration of about 40 μg/ml to about 180 μg/ml, for example, about 150 μg/ml, and/or the first gRNA that targets Reg1 may have a concentration of about 40 μg/ml to about 160 μg/ml, e.g., about 120 μg/ml. In other examples, the Cas9 enzyme may have a concentration of about 40 μg/ml to about 150 μg/ml, e.g., about 120 μg/ml; and/or the second gRNA that targets the TGFBRII gene has a concentration of about 80 μg/ml to about 160 μg/ml, e.g., about 120 μg/ml. In some specific examples, the Cas9 enzyme may have a total concentration of about 250 μg/ml to about 300 μg/ml (e.g., about 270 μg/ml), the first gRNA that targets Reg1 may have a concentration of about 120 μg/ml, and the second gRNA that targets the TGFBRII gene may have a concentration of about 120 μg/ml.

In some instances, step (ii-b) may be performed for about 48 hours. In some examples, the medium used in step (ii-b) may contain no T cell activating agent.

In any of the methods disclosed above, the second gene editing system in step (ii-c) comprises the third gRNA that targets the TRAC gene, the fourth gRNA that targets the β2M gene, and the one or more Cas9 enzymes. In some embodiments, each of the third gRNA that targets the TRAC gene and the fourth gRNA that targets the β2M gene forms an RNP complex with the Cas9 enzyme. In some examples, a mixture of the RNP complexes is introduced to the recovered T cells by the second electroporation. For example, the recovered T cells have a concentration of about $1\times10^8$ cells/ml to about $5\times10^8$ cells/ml, e.g., about $3\times10^8$ cells/ml. In specific examples, the Cas9 enzyme has a total concentration of about 300 μg/ml, the third gRNA that targets the TRAC gene has a concentration of about 80 μg/ml, and/or the fourth gRNA that target β2M has a concentration of about 200 μg/ml.

In some embodiments, the second gene editing system in step (ii-c) comprises the third gRNA that targets the TRAC gene, the fifth gRNA that targets the CD70 gene, and the one or more Cas9 enzymes. In some instances, the third gRNA that targets the TRAC gene and the fifth gRNA that targets the CD70 gene form one or more RNPs with the Cas9 enzyme(s) (e.g., two separate RNPs, which can be mixed for electroporation).

In any of the methods disclosed herein, the AAV particles in step (ii-d) are AAV6 particles. In some embodiments, the AAV particles have a multiplicity of infection (MOI) value of about 20,000 to about 50,000 vg/cell. Alternatively or in addition, step (ii-d) is performed for at least one hour.

Any of the methods disclosed above may further comprise:

(iii) expanding the genetically engineered T cells produced in step (ii) to produce an expanded T cell population;

(iv) removing TCRαβ⁺ T cells from the expanded T cell population; and (v) harvesting the genetically engineered T cells depleted with TCRαβ⁺ T cells.

In some embodiments, step (iii) can be performed by seeding the genetically engineered T cells produced in step (ii) at a density of about $0.3\times10^6$ viable cells/cm$^2$ to about $0.5\times10^6$ viable cells/cm$^2$ in one or more cell culture vessels and culturing the T cells for about 3 to about 9 days, e.g., for about 6 to about 9 days. In some embodiments, the T cells can be supplemented with interleukin-2, optionally at a concentration of about 100 IU/ml, and interleukin 7, optionally at a concentration of a concentration of 100 IU/ml, every 3 to 4 days. In some embodiments, the one or more cell culture vessels are static cell culture vessels.

In some embodiments, step (iv) can be performed by contacting the expanded T cells to beads on which anti-TCRαβ antibodies are immobilized, and collecting unbound cells. In some examples, the method may further comprise recovering the T cells after removal of the TCRαβ$^+$ T cells.

In other aspects, provided herein is a method for manufacturing genetically engineered T cells, the method comprising:

(i) providing a population of T cells;

(ii) activating the population of T cells in step (i) to produce a population of activated T cells;

(iii) performing a first electroporation to the activated T cells to introduce a first Cas9 enzyme, a first guide RNA (gRNA) targeting a Regnase 1 (Reg1) gene, and a second gRNA targeting a Transforming Growth Factor Beta Receptor II (TGFBRII) gene to produce a first population of genetically engineered T cells;

(iv) culturing the first population of genetically engineered T cells in a medium for T cell recovery, (v) performing a second electroporation to the recovered cells from step (iv) to introduce a second Cas9 enzyme, a third Cas9 enzyme, a third gRNA targeting a T cell receptor alpha chain constant region (TRAC) gene, and a fourth gRNA targeting a beta-2 microglobulin (β2M) gene to produce a second population of genetically engineered T cells;

(vi) incubating the second population of genetically engineered T cells with recombinant AAV particles, which comprise a donor template, wherein the donor template comprises a nucleic acid sequence encoding a chimeric antigen receptor that binds human CD19 (anti-CD19 CAR) flanked by a left homology arm and a right homology arm, wherein the left homology arm and the right homology arm are homologous to a locus in the TRAC gene;

(vii) expanding the second genetically engineered T cells to produce an expanded T cell population;

(viii) removing TCRαβ$^+$ T cells from the expanded T cell population; and (ix) harvesting the genetically engineered T cells produced in step (viii).

The genetically engineered T cells harvested in step (viii) may comprise a disrupted TRAC gene, a disrupted β2M gene, a disrupted Reg1 gene, a disrupted TGFBRII gene, and the nucleic acid sequence encoding the anti-CD19 CAR, which is inserted into the disrupted TRAC gene.

In some embodiments, the T cell population in step (i) is derived from cryopreserved T cells enriched from human blood cells. For example, the human blood cells are obtained from one or more human donors. In some examples, the T cell population in step (i) is prepared by a process comprising: (i-a) obtaining blood cells from one or more human donors, (i-b) enriching CD4$^+$ T cells, CD8$^+$ T cells, or both from the blood cells. The process may further comprise (i-c) freezing the enriched T cells from step (i-b).

In some embodiments, the activating step (ii) is performed by incubating a T cell population in the presence of a T cell activating agent in a cell culture vessel to produce the population of activated T cells. The T cell activating agent may comprise a CD3 agonist and a CD28 agonist. In some examples, the T cell activating agent such as the CD3 agonist and/or the CD28 agonist can be attached to a nanomatrix particle. In some instances, the activating step (ii) is performed for about 24-72 hours, optionally for about 48 hours.

In some embodiments, in step (iii), the Cas9 enzyme and the first gRNA that targets the Reg1 gene and second gRNA that targets the TGFBRII gene form an RNP complex. For example, the Cas9 enzyme and the first gRNA that targets the Reg1 gene may be at a weight ratio of 4:1 to 1:4, e.g., 2:1 to 1:2. Alternatively or in addition, the Cas9 enzyme and the second gRNA that targets the TGFBRII gene may be at a weight ratio of 4:1 to 1:4, e.g., 2:1 to 1:2. In some examples, the activated T cells have a concentration of about $1\times10^8$ cells/ml to about $5\times10^8$ cells/ml; e.g., about $3\times10^8$ cells/ml.

In some examples, in step (iii), the Cas9 enzyme may have a concentration of about 40 μg/ml to about 180 μg/ml (e.g., about 150 μg/ml) and/or the first gRNA that targets Reg1 may have a concentration of about 40 μg/ml to about 160 μg/ml (e.g., about 120 μg/ml). In other examples, the Cas9 enzyme may have a concentration of about 40 μg/ml to about 150 μg/ml (e.g., about 120 μg/ml); and/or the second gRNA that targets the TGFBRII gene may have a concentration of about 80 μg/ml to about 160 μg/ml (e.g., about 120 μg/ml). In specific examples, the Cas9 enzyme may have a total concentration of about 250 μg/ml to about 300 μg/ml (e.g., about 270 μg/ml); the first gRNA that targets Reg1 may have a concentration of about 120 μg/ml, and the second gRNA that targets the TGFBRII gene may have a concentration of about 120 μg/ml.

In some embodiments, step (iv) can be performed for about 48 hours. In some examples, the medium used in step (iv) contains no T cell activating agent.

In some embodiments, in step (v), each of the third gRNA that targets the TRAC gene and the fourth gRNA that targets the β2M gene may form an RNP complex with the Cas9 enzyme. In some instances, a mixture of the RNP complexes is introduced to the recovered T cells by the second electroporation. In some examples, the recovered T cells have a concentration of about $1\times10^8$ cells/ml to about $5\times10^8$ cells/ml, e.g., about $3\times10^8$ cells/ml. In some specific examples, the Cas9 enzyme may have a total concentration of about 300 μg/ml, the third gRNA that targets the TRAC gene may have a concentration of about 80 μg/ml, and/or the fourth gRNA that target β2M may have a concentration of about 200 μg/ml.

In some embodiments, the AAV particles in step (vi) are AAV6 particles. In some examples, the AAV particles may have a multiplicity of infection (MOI) value of about 20,000 to about 50,000 vg/cell. Alternatively or in addition, step (vi) may be performed for at least one hour.

In some embodiments, step (vii) may be performed by seeding the genetically engineered T cells produced in step (ii) at a density of about $0.3\times10^6$ viable cells/$cm^2$ to about $0.5\times10^6$ viable cells/$cm^2$ in one or more cell culture vessels and culturing the T cells for about 3 to about 9 days, e.g., for about 6 to about 9 days. In some instances, the T cells are supplemented with interleukin-2, optionally at a concentration of about 100 IU/ml, and interleukin 7, for example, at a concentration of a concentration of 100 IU/ml, every 3 to 4 days. In some examples, the one or more cell culture vessels are static cell culture vessels.

In some embodiments, step (viii) is performed by contacting the expanded T cells to beads on which anti-TCRαβ antibodies are immobilized, and collecting unbound cells. Such a step may further comprise recovering the T cells after removal of the $TCR\alpha\beta^+$ T cells.

Further, the present disclosure features a method for manufacturing genetically engineered T cells, the method comprising:

(i) providing a population of T cells;
(ii) activating the population of T cells in step (i) to produce a population of activated T cells;
(iii) performing a first electroporation to the activated T cells to introduce at least a first Cas9 enzyme, a first guide RNA (gRNA) targeting a Regnase 1 (Reg1) gene, a second gRNA targeting a Transforming Growth Factor Beta Receptor II (TGFBRII) gene, and a fourth gRNA targeting a β2M gene to produce a first population of genetically engineered T cells;
(iv) culturing the first population of genetically engineered T cells in a medium for T cell recovery,
(v) performing a second electroporation to the recovered cells from step (iv) to introduce at least a second Cas9 enzyme, a third gRNA targeting a T cell receptor alpha chain constant region (TRAC) gene, and a fifth gRNA targeting a CD70 gene to produce a second population of genetically engineered T cells;
(vi) incubating the second population of genetically engineered T cells with recombinant AAV particles, which comprise a donor template, wherein the donor template comprises a nucleic acid sequence encoding a chimeric antigen receptor that binds human CD70 (anti-CD70 CAR) flanked by a left homology arm and a right homology arm, wherein the left homology arm and the right homology arm are homologous to a locus in the TRAC gene;
(vii) expanding the second genetically engineered T cells to produce an expanded T cell population;
(viii) removing $TCR\alpha\beta^+$ T cells from the expanded T cell population; and
(ix) harvesting the genetically engineered T cells produced in step (viii).

The genetically engineered T cells harvested in step (viii) may comprise a disrupted TRAC gene, a disrupted β2M gene, a disrupted Reg1 gene, a disrupted TGFBRII gene, a disrupted CD70 gene, and the nucleic acid sequence encoding the anti-CD70 CAR, which is inserted into the disrupted TRAC gene.

In some embodiments, the T cell population in step (i) can be derived from cryopreserved T cells enriched from human blood cells. For example, the human blood cells are obtained from one or more human donors. In some examples, the T cell population can be prepared by a process comprising: (i-a) obtaining blood cells from one or more human donors, (i-b) enriching $CD4^+$ T cells, $CD8^+$ T cells, or both from the blood cells. The process may further comprise (i-c) freezing the enriched T cells from step (i-b).

In some embodiments, step (ii) can be performed by incubating a T cell population in the presence of a T cell activating agent in a cell culture vessel to produce the population of activated T cells. The T cell activating agent may comprise a CD3 agonist and a CD28 agonist. In some instances, the T cell activating agent such as the CD3 agonist and/or the CD28 agonist may be attached to a nanomatrix particle. In some examples, step (ii) can be performed for about 24-72 hours, e.g., for about 48 hours.

In some embodiments, in step (iii), the first gRNA that targets the Reg1 gene, the second gRNA that targets the TGFBRII gene, and the fourth gRNA that targets the β2M gene may form one or more RNP complexes with the at least first Cas9 enzyme (e.g., form separate RNPs each comprising one gRNA and a Cas9 enzyme). In some examples, the RNPs can be mixed for use in the electroporation. In some examples, the activated T cells have a concentration of about $1\times10^8$ cells/ml to about $5\times10^8$ cells/ml, e.g., about $3\times10^8$ cells/ml.

In some embodiments, the first gRNA that targets the Reg1 gene may be at a concentration of about 60 μg/ml to about 100 μg/ml. In some examples, the first gRNA that targets the Reg1 gene may be at a concentration of about 80 μg/ml. Alternatively or in addition, the Cas9 enzyme forming an RNP with the first gRNA may be at a concentration of about 120 μg/ml to about 180 μg/ml. In some examples, the Cas9 enzyme forming an RNP with the first gRNA may be at a concentration of 150 μg/ml.

In some embodiments, the fourth gRNA that targets the β2M gene may be at a concentration of about 180 μg/ml to about 220 μg/ml. In some examples, the fourth gRNA that targets the β2M gene may be at a concentration of about 200 μg/ml. Alternatively or in addition, the Cas9 enzyme forming an RNP with the fifth gRNA may be at a concentration of about 120 μg/ml to about 180 μg/ml. In some examples, the Cas9 enzyme forming an RNP with the fifth gRNA may be at a concentration of 150 μg/ml.

In some embodiments, the second gRNA that targets the TGFBRII gene may be at a concentration of about 100 μg/ml to about 160 μg/ml. In some examples, the second gRNA that targets the TGFBRII gene may be at a concentration of about 120 μg/ml. Alternatively or in addition, the Cas9 enzyme forming an RNP with the second gRNA may be at a concentration of about 100 μg/ml to about 150 μg/ml, for example, at a concentration of about 120 μg/ml.

In some embodiments, step (iv) can be performed for about 48 hours. In some examples, the medium used in step (iv) may contain no T cell activating agent.

In some embodiments, in step (v), the third gRNA that targets the TRAC gene and the fifth gRNA that targets the CD70 gene may form one or more RNP complexes with the at least second Cas9 enzyme (e.g., form separate RNPs each comprising a gRNA and a Cas9 enzyme). In some examples, the RNPs can be mixed for use in the electroporation. In some examples, the recovered T cells have a concentration of about $1\times10^8$ cells/ml to about $5\times10^8$ cells/ml, e.g., about $3\times10^8$ cells/ml.

In some embodiments, the third gRNA that targets the TRAC gene may be at a concentration of about 80 μg/ml to about 160 μg/ml. In some examples, the third gRNA that targets the TRAC gene may be at a concentration of 120 μg/ml. Alternatively or in addition, the Cas9 enzyme forming an RNP with the third gRNA may be at a concentration of about 120 μg/ml to about 180 μg/ml, for example, at a concentration of 150 μg/ml.

In some embodiments, the fifth gRNA that target CD70 gene may be at a concentration of about 140 μg/ml to about 160 μg/ml. For example, the fifth gRNA may be at a concentration of about 160 μg/ml. In some instances, the Cas9 enzyme forming an RNP with the fifth gRNA may be at a concentration of about 120 μg/ml to about 180 μg/ml, for example, at a concentration of 150 μg/ml.

In some embodiments, the AAV particles in step (vi) are AAV6 particles. In some examples, the AAV particles have a multiplicity of infection (MOI) value of about 20,000 to about 50,000 vg/cell. In some examples, step (vi) can be performed for at least one hour.

In some embodiments, step (vii) can be performed by seeding the genetically engineered T cells produced in step (ii) at a density of about $0.3\times10^6$ viable cells/$cm^2$ to about $0.5\times10^6$ viable cells/$cm^2$ in one or more cell culture vessels and culturing the T cells for about 3 to about 9 days, for example, for about 6 to about 9 days. The T cells may be supplemented with interleukin-2 (e.g., at a concentration of about 100 IU/ml), and interleukin 7 (e.g., at a concentration of a concentration of 100 IU/ml) every 3 to 4 days. In some examples, the one or more cell culture vessels are static cell culture vessels.

In some embodiments, step (vii) can be performed by contacting the expanded T cells to beads on which anti-TCRαβ antibodies are immobilized and collecting unbound cells. This step may further comprise recovering the T cells after removal of the $TCR\alpha\beta^+$ T cells.

In any of the methods disclosed herein, the one or more Cas9 enzymes are *Streptococcus pyogenes* Cas9 nuclease (spCas9), e.g., comprising the amino acid sequence of SEQ ID NO:1. In some embodiments, the first gRNA that targets the Reg1 gene may comprise a spacer sequence of SEQ ID NO: 5. In some examples, the first gRNA may comprise the nucleotide sequence of SEQ ID NO: 3. In some embodiments, the second gRNA that targets the TGFBRII gene may comprise a spacer sequence of SEQ ID NO: 9. In some examples, the second gRNA may comprise the nucleotide sequence of SEQ ID NO: 7. In some embodiments, the third gRNA that targets the TRAC gene may comprise a spacer sequence of SEQ ID NO: 13. In some examples, the third gRNA may comprise the nucleotide sequence of SEQ ID NO: 11. In some embodiments, the fourth gRNA that targets the β2M gene may comprise a spacer sequence of SEQ ID NO: 17. In some examples, the fourth gRNA may comprise the nucleotide sequence of SEQ ID NO: 15. In some embodiments, the fifth gRNA that targets the CD70 gene may comprise a spacer sequence of SEQ ID NO: 21. In some examples, the fifth gRNA may comprise the nucleotide sequence of SEQ ID NO: 19. Any of the gRNAs disclosed herein may comprise one or more 2'-O-methyl phosphorothioate modification.

In some embodiments, the CAR binds CD19 (anti-CD19 CAR), which may comprise an extracellular domain targeting a cancer antigen, a transmembrane domain, a co-stimulatory domain, and a CD3ζ cytoplasmic signaling domain. In some examples, the extracellular domain thereof may comprise a single-chain variable fragment (scFv) that binds human CD19, the transmembrane domain may be derived from CD8a, and/or the co-stimulatory domain may be derived from CD28. In specific examples, the scFv that binds CD19 comprises the amino acid sequence of SEQ ID NO: 69. In one example, the anti-CD19 CAR comprises the amino acid sequence of SEQ ID NO: 71, or the mature form thereof, which lacks the N-terminal signal peptide. In some examples, the donor template encoding the anti-CD19 CAR may comprise the nucleotide sequence of SEQ ID NO: 91.

In some embodiments, the CAR is an anti-CD70 CAR, which may comprise an extracellular domain targeting a cancer antigen, a transmembrane domain, a co-stimulatory domain, and a CD3ζ cytoplasmic signaling domain. In some examples, and the extracellular domain thereof may comprise a single-chain variable fragment (scFv) that binds human CD70, the transmembrane domain may be derived from CD8a, and/or the co-stimulatory domain may be derived from 4-1BB. In some examples, the scFv that binds CD70 may comprise the amino acid sequence of SEQ ID NO: 76. In one example, the anti-CD70 CAR may comprise the amino acid sequence of SEQ ID NO: 78, or the mature form thereof, which lacks the N-terminal signal peptide. In another example, the donor template comprising the coding sequence of the anti-CD70 CAR may comprise the nucleotide sequence of SEQ ID NO: 92.

Moreover, the present disclosure also provides a population of genetically engineered T cells, which is produced by any of the methods disclosed herein.

The present disclosure further features a method for inhibiting undesired cells in a subject, the method comprising administering to a subject in need thereof an effective amount of the population of genetically engineered T cells disclosed herein, which express a CAR specific to an antigen of the undesired cells. In some embodiments, the undesired cells are CD19+ or CD70+. In some examples, the CAR binds CD19. In other examples, the CAR binds CD70. In some examples, the undesired cells are cancer cells. Examples include hematopoietic cancer cells or solid tumor cells.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

BRIEF DESCRIPTIONS OF THE DRAWINGS

FIGS. 1A-1E include diagrams showing impact of T cell activation timing on gene editing efficiencies. FIG. 1A: editing efficiency of TRAC. FIG. 1B: editing efficiency of β2M. FIG. 1C: editing efficiency of Regnase-1. FIG. 1D: editing efficiency of TGFBRII. FIG. 1E: editing efficiency of CD70. A0-A4: Activation for 0 to 4 days.

FIG. 4 is a schematic illustration depicting an exemplary manufacturing process for preparing genetically engineered T cells using the CRISPR/Cas9 gene editing system. TGFBR2 is equivalent to TGFBRII.

Figures 6A, 6B, 6C:
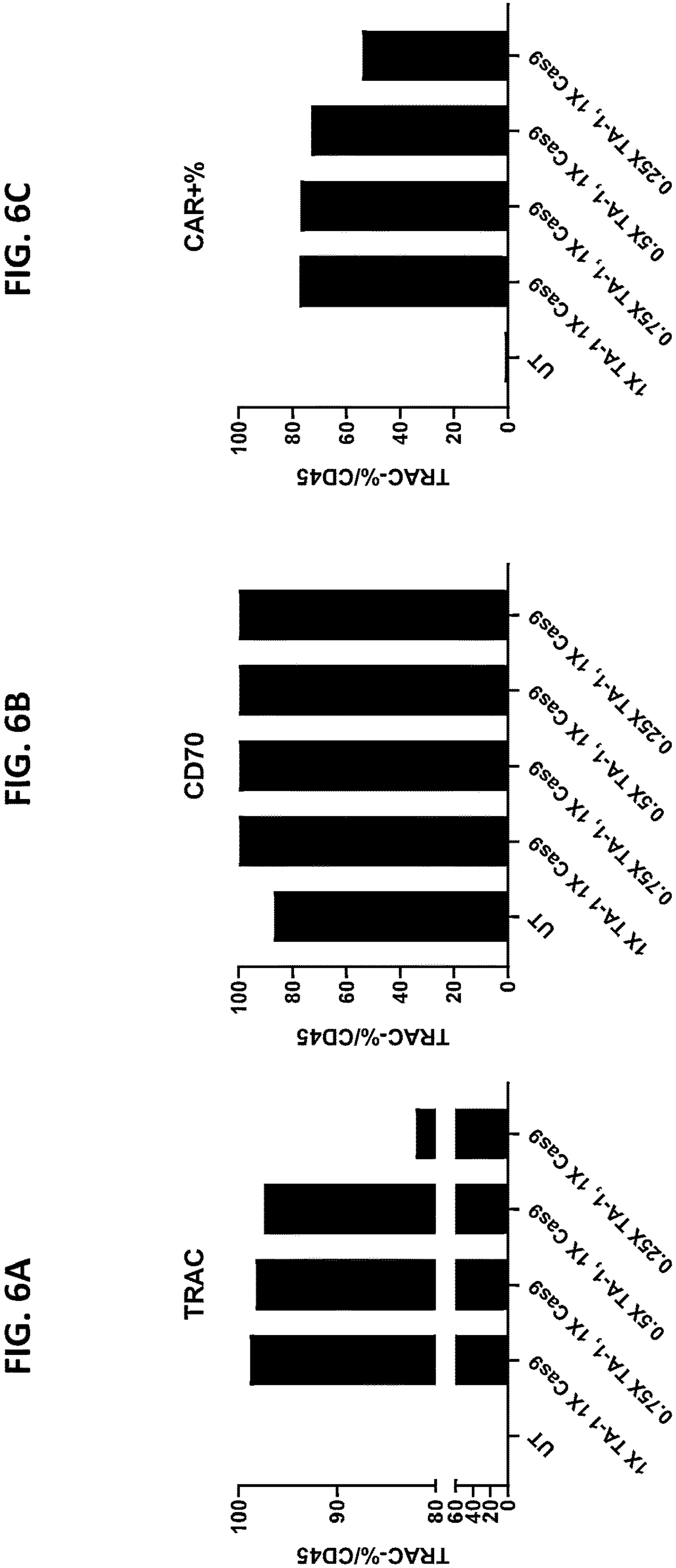

FIGS. 6A-6C include diagrams showing editing efficiencies of TRAC (FIG. 6A) and CD70 (FIG. 6B), and CAR expression levels (FIG. 6C) at various TA-1 guide concentrations and Cas9 concentrations.

Figure 7B:
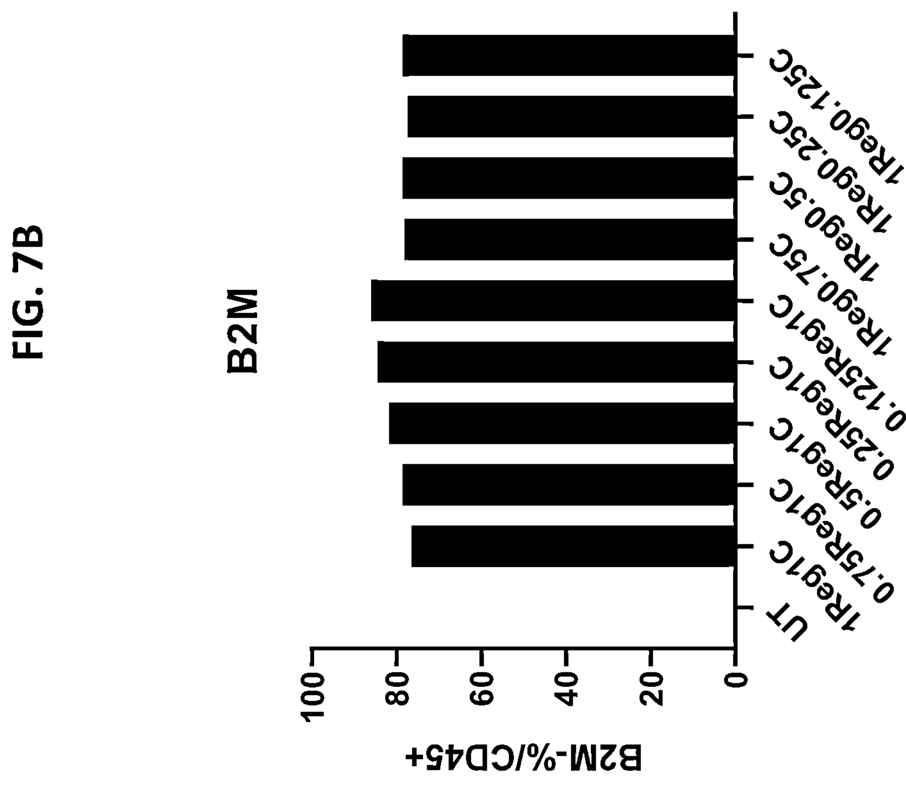
Figure 7A:
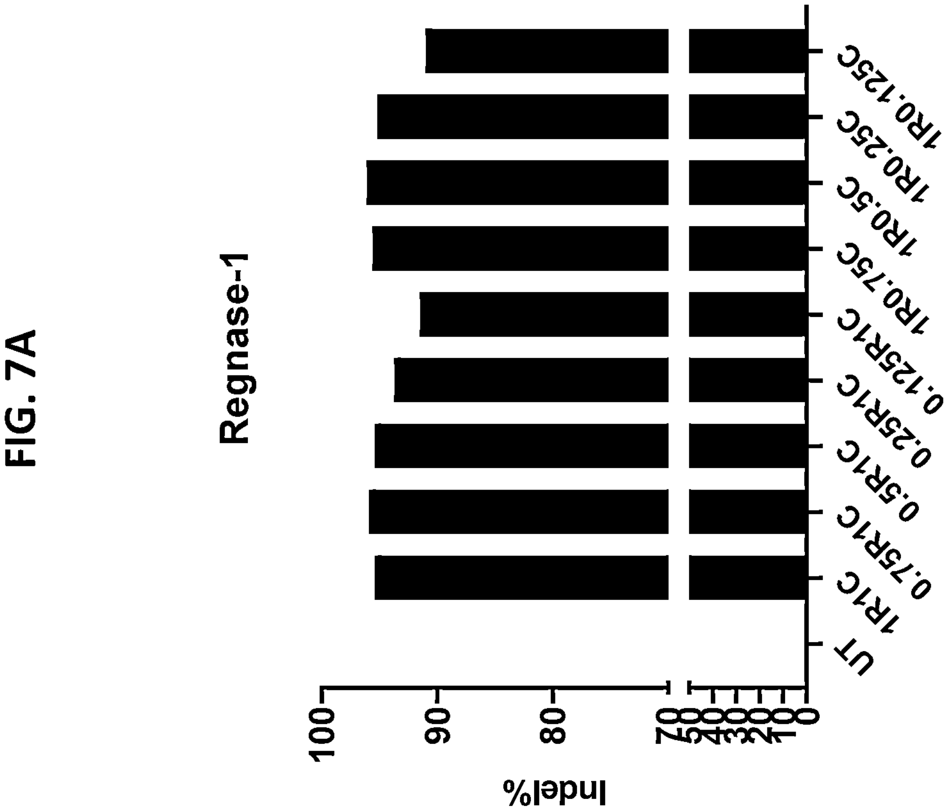

FIGS. 7A-7B include diagrams showing CAR-expressing level (FIG. 7A) and editing efficiencies of β2M (FIG. 7B) at various concentrations of Regase-1 guide.

FIG. 8 is a schematic illustration depicting an exemplary manufacturing process for preparing genetically engineered T cells expressing an anti-CD70 CAR and having disrupted TRAC gene, β2M gene, CD70 gene, Reganase-1 gene, and TGFBRII gene, using the CRISPR/Cas9 gene editing system.

Figure 9B:
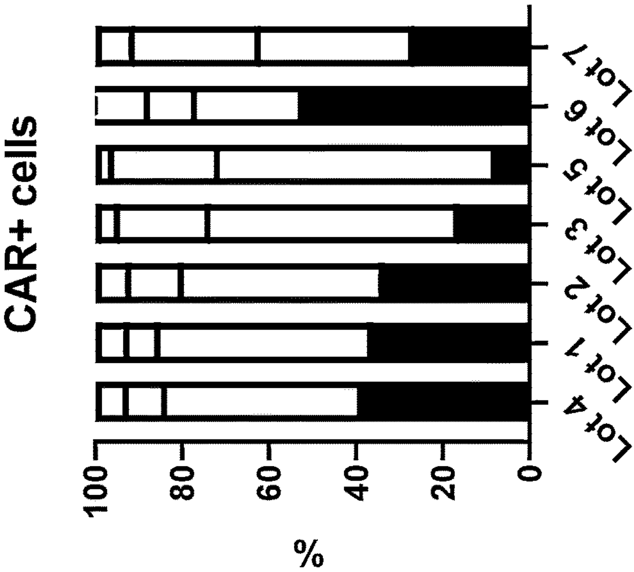
Figure 9A:
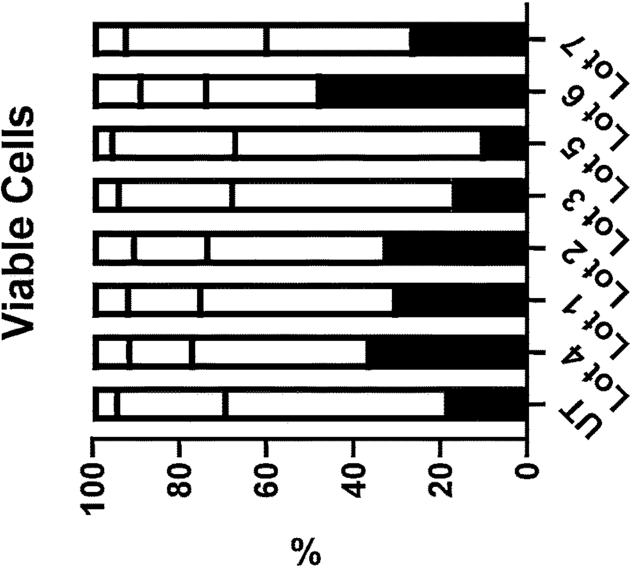
Figure 9D:
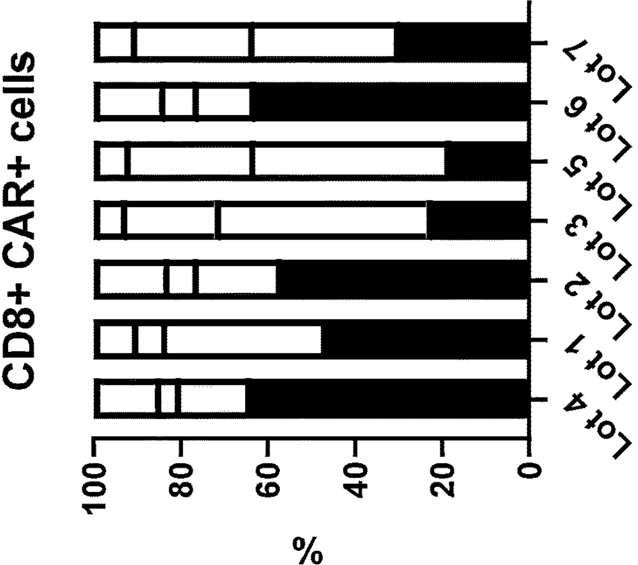
Figure 9C:
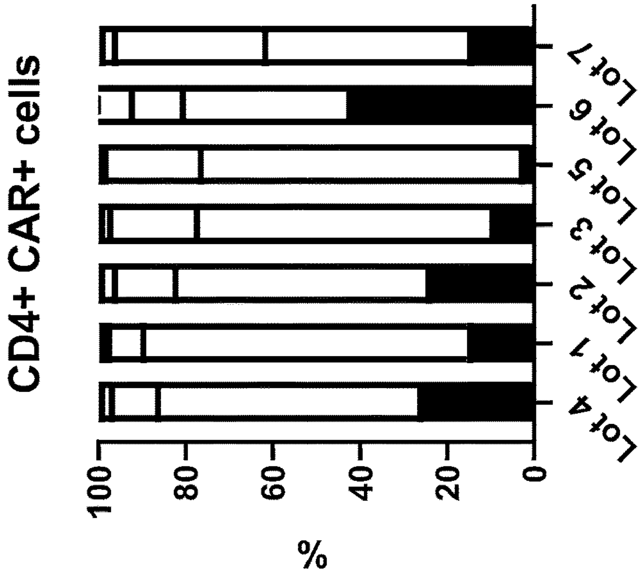

FIGS. 9A-9D include diagrams showing subset cell populations. FIG. 9A: Viable cells; FIG. 9B: CAR+ cells; FIG. 9C: CD4+ CAR+ cells; FIG. 9D: CD8+ CAR+ cells.

Figure 10B:
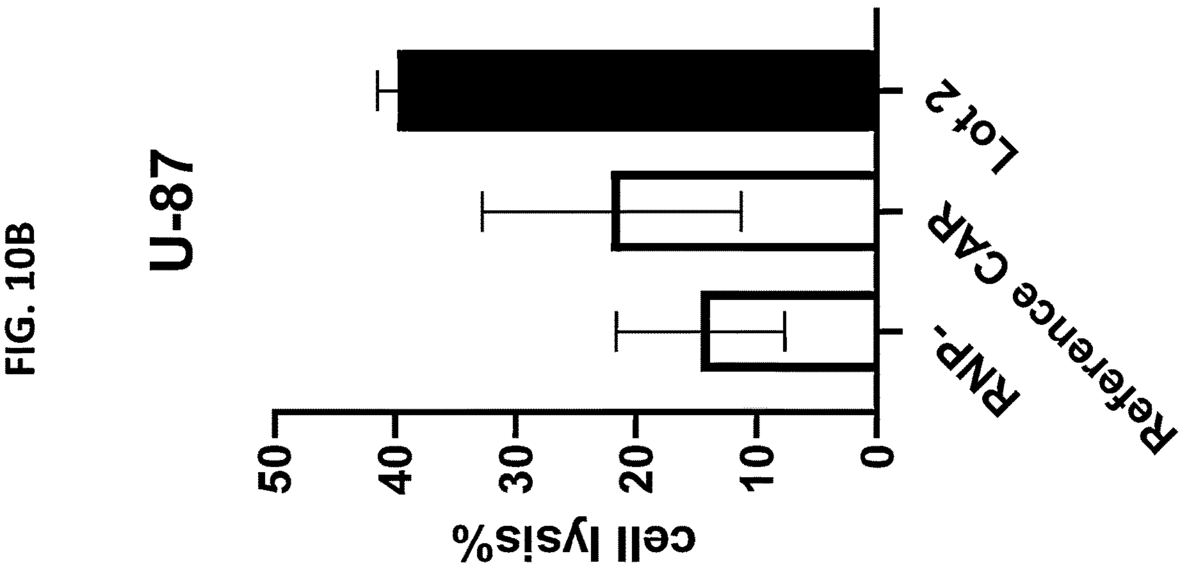
Figure 10A:
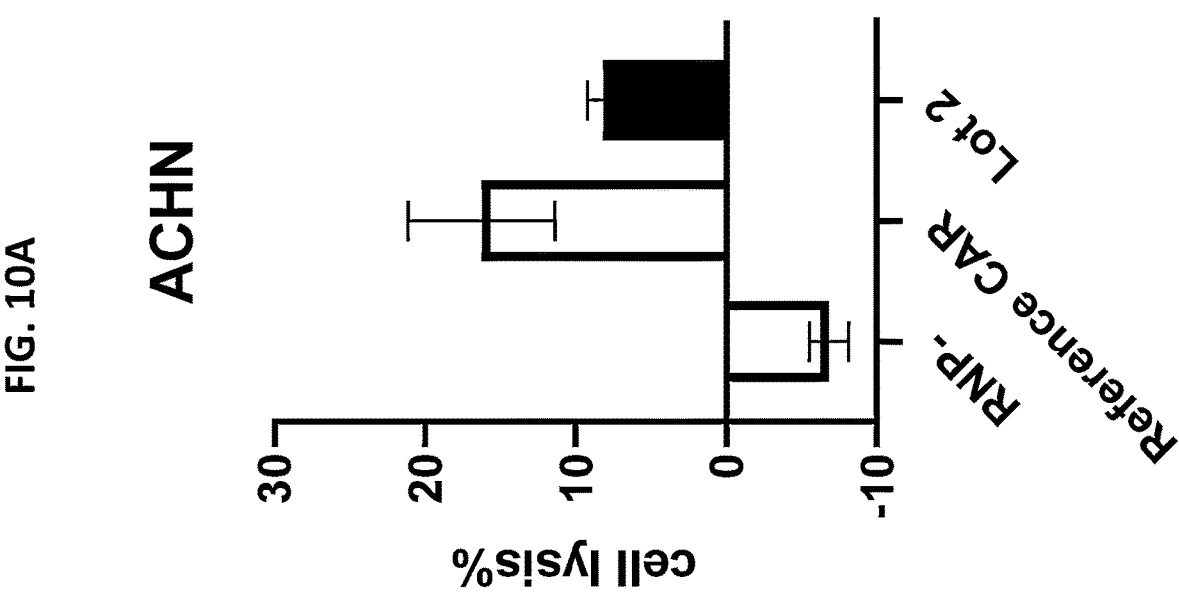

FIGS. 10A-10B include diagrams showing in vitro cell killing by the CAR-T cells. FIG. 10A: ACHN cells; FIG. 10B: U-87 cells.

Figure 11A:
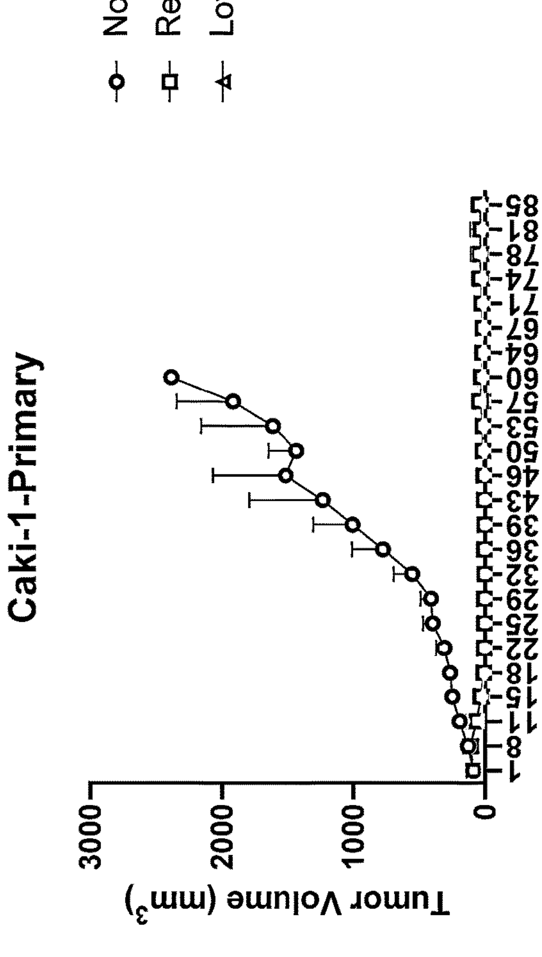
Figure 11B:
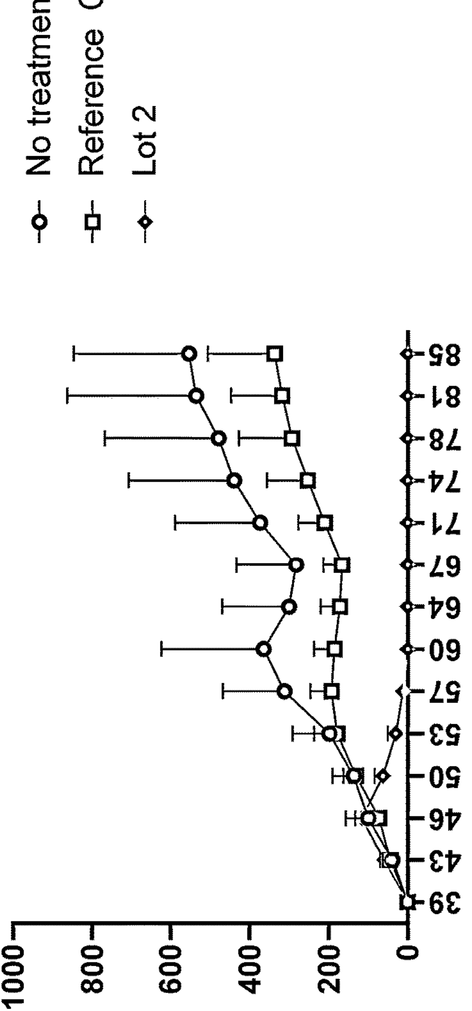

FIGS. 11A-11B include diagrams showing in vivo efficacy comparing mice treated with anti-CD70 CAR-T cells with mice treated with Reference CAR cells or untreated mice. FIG. 11A: mice injected with Caki-1 cells. FIG. 11B: mice rechallenged with ACHN cells.

Figure 12B:
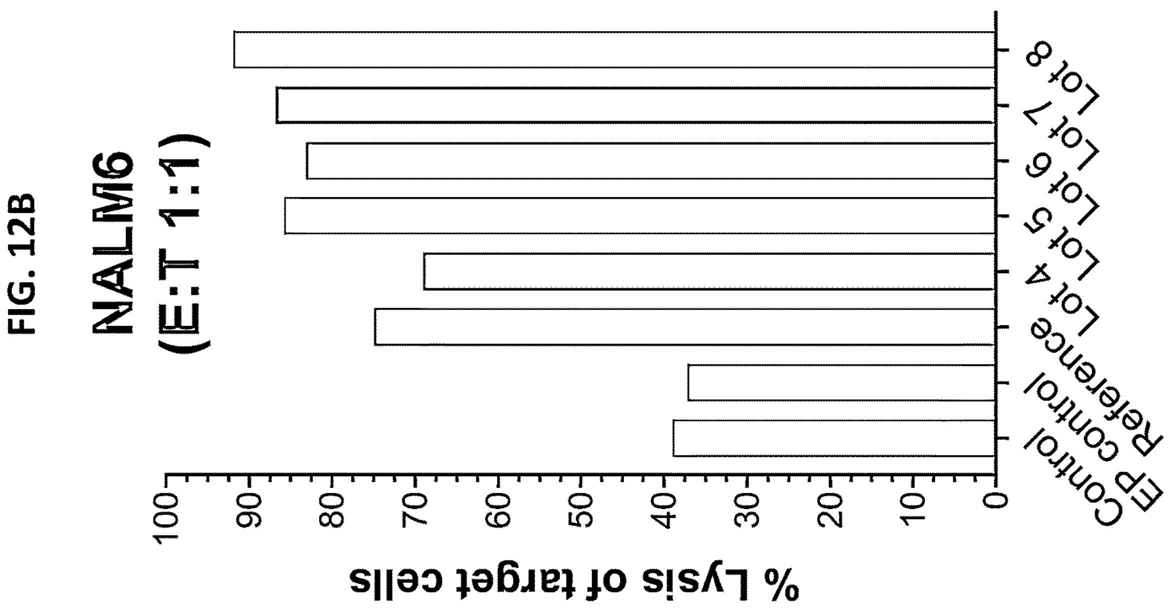
Figure 12A:
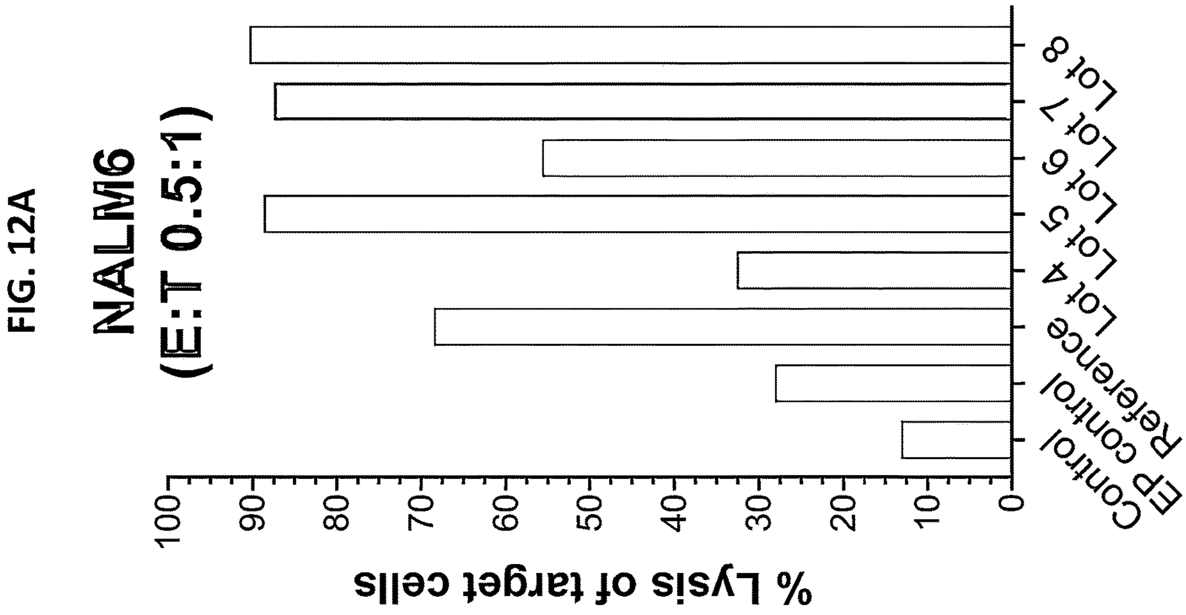

FIGS. 12A-12B include diagrams showing in vitro cell kill assay results using NALM6 cells. FIG. 12A: E:T=0.5:1. FIG. 12B: E:T=1:1.

Figure 13B:
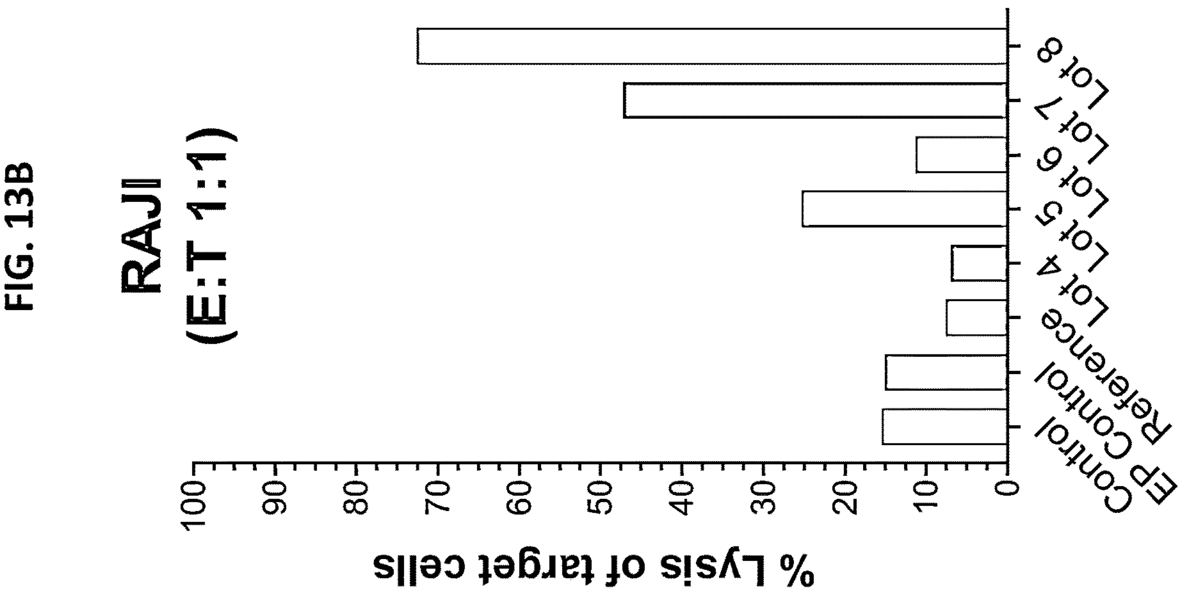
Figure 13A:
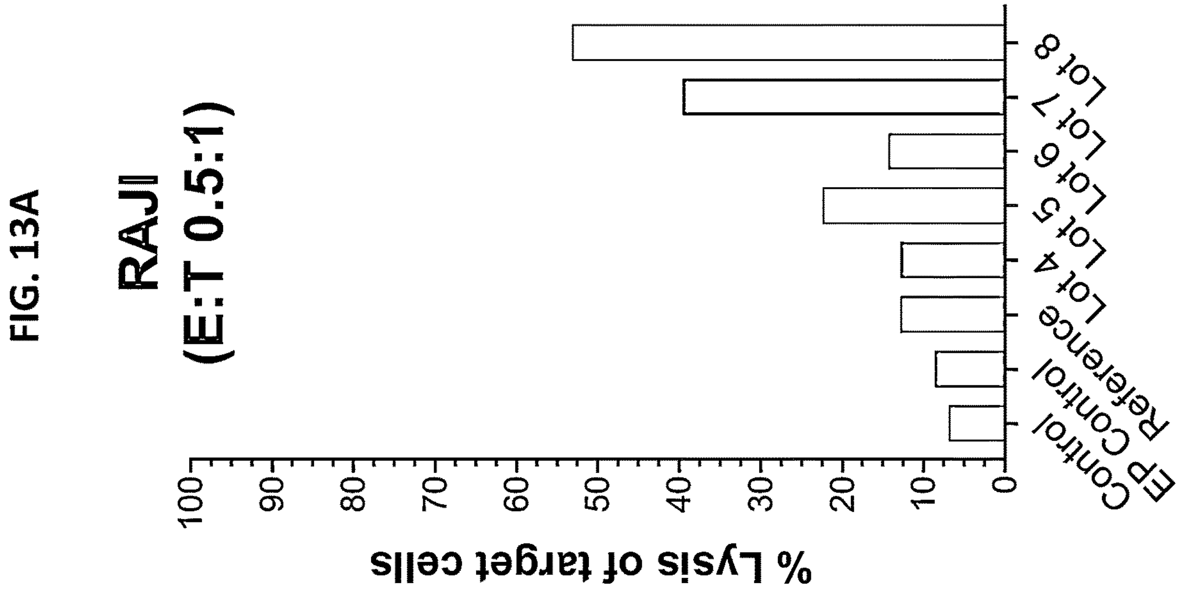

FIGS. 13A-13B include diagrams showing in vitro cell kill assay results using Raji cells. FIG. 13A: E:T=0.5:1. FIG. 13B: E:T=1:1.

Figure 14A:
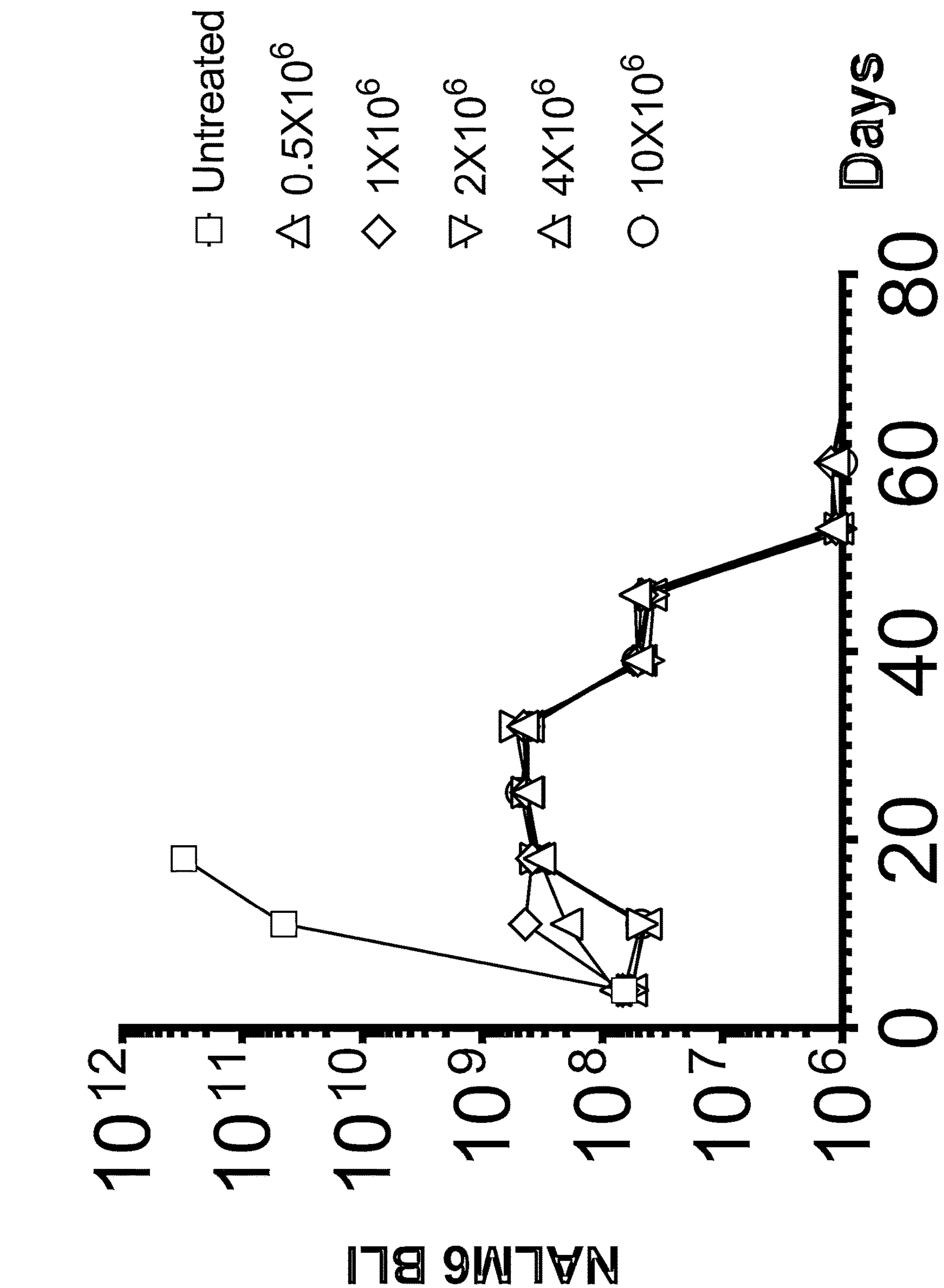
Figure 14B:
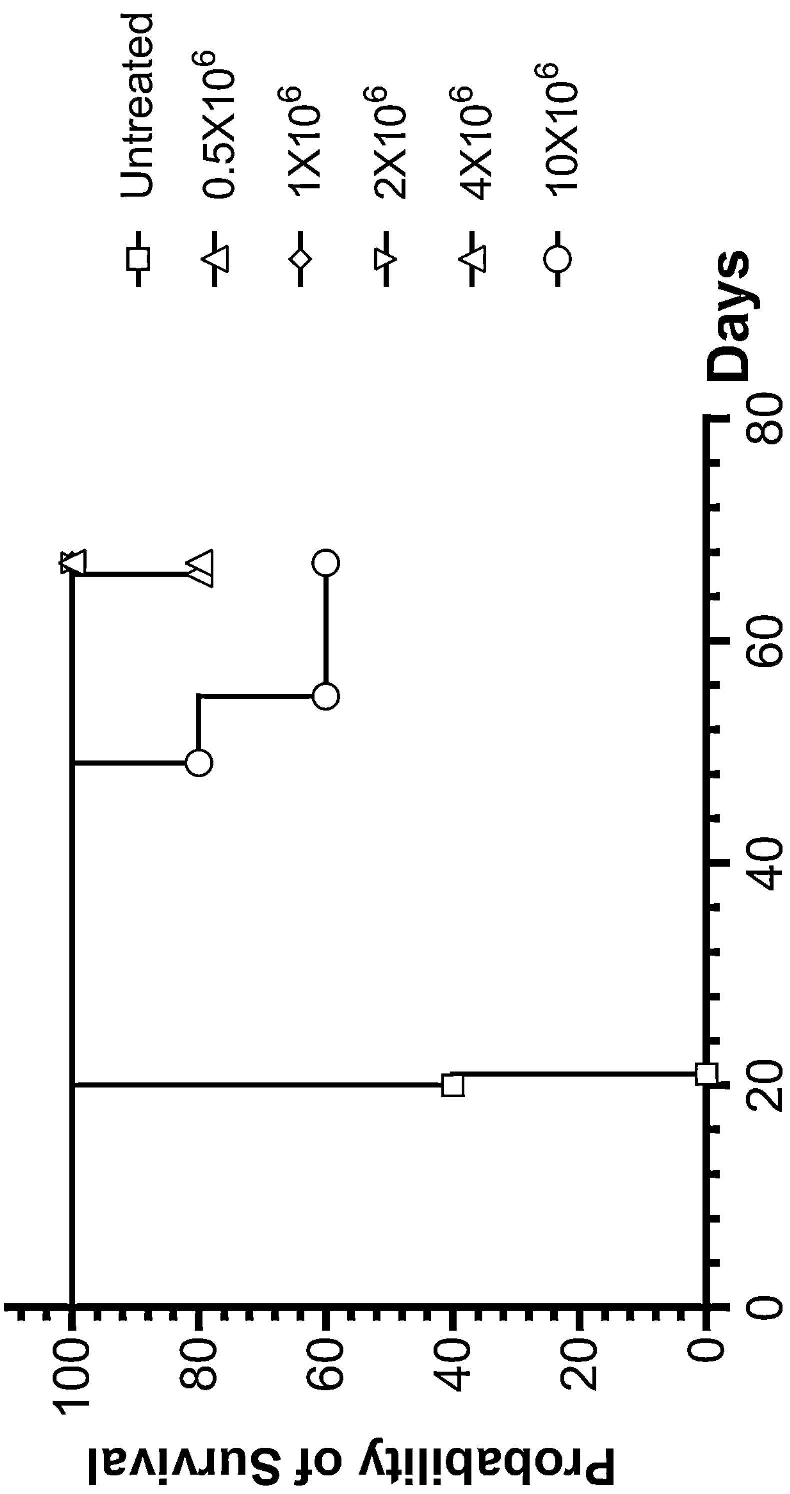

FIGS. 14A-14B include diagrams showing in vivo efficacy in mice inoculated with Nalm6 cells. FIG. 14A: efficacy based on bioluminescence and FIG. 14B: survival rates.

Figure 15A:
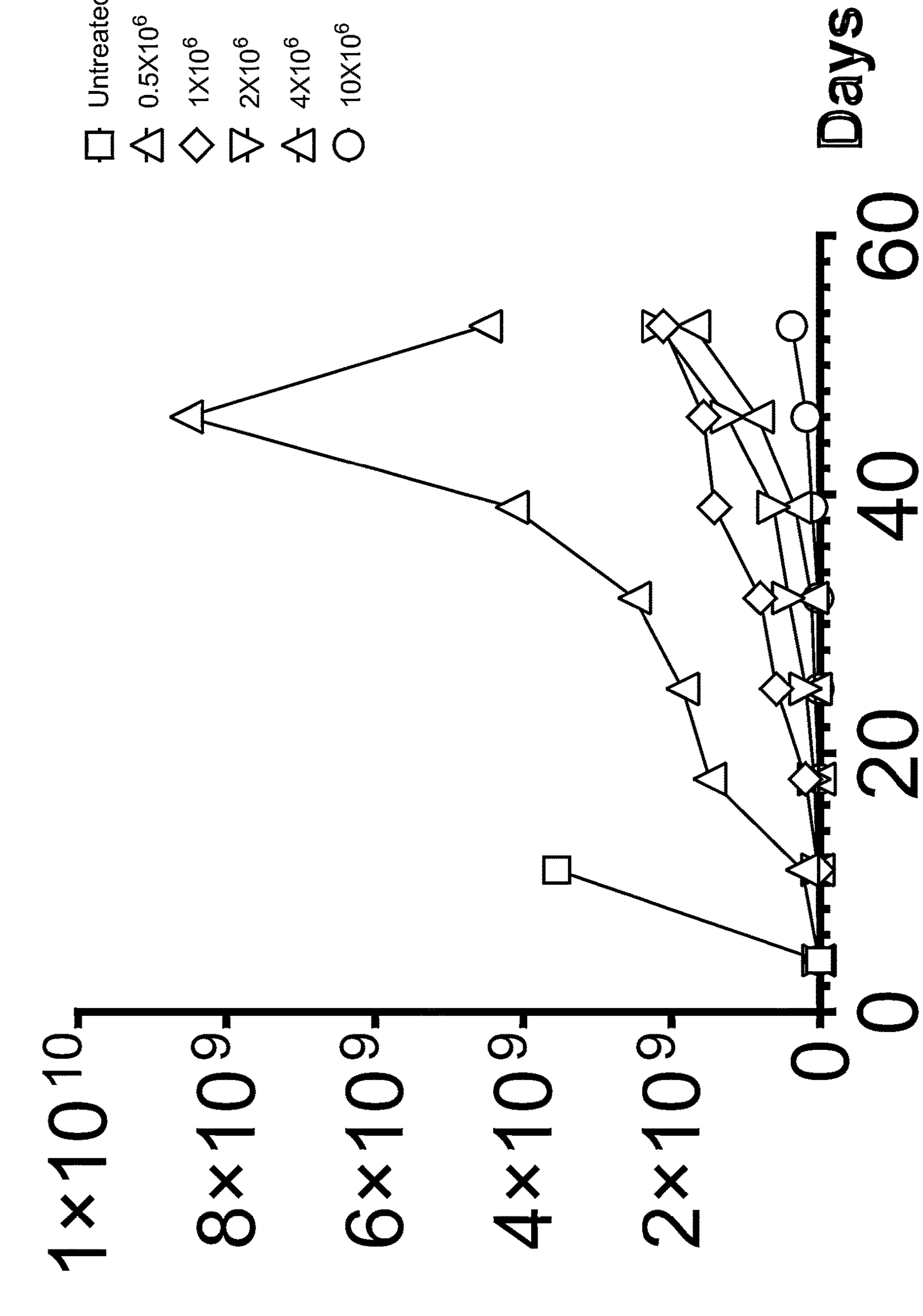
Figure 15B:
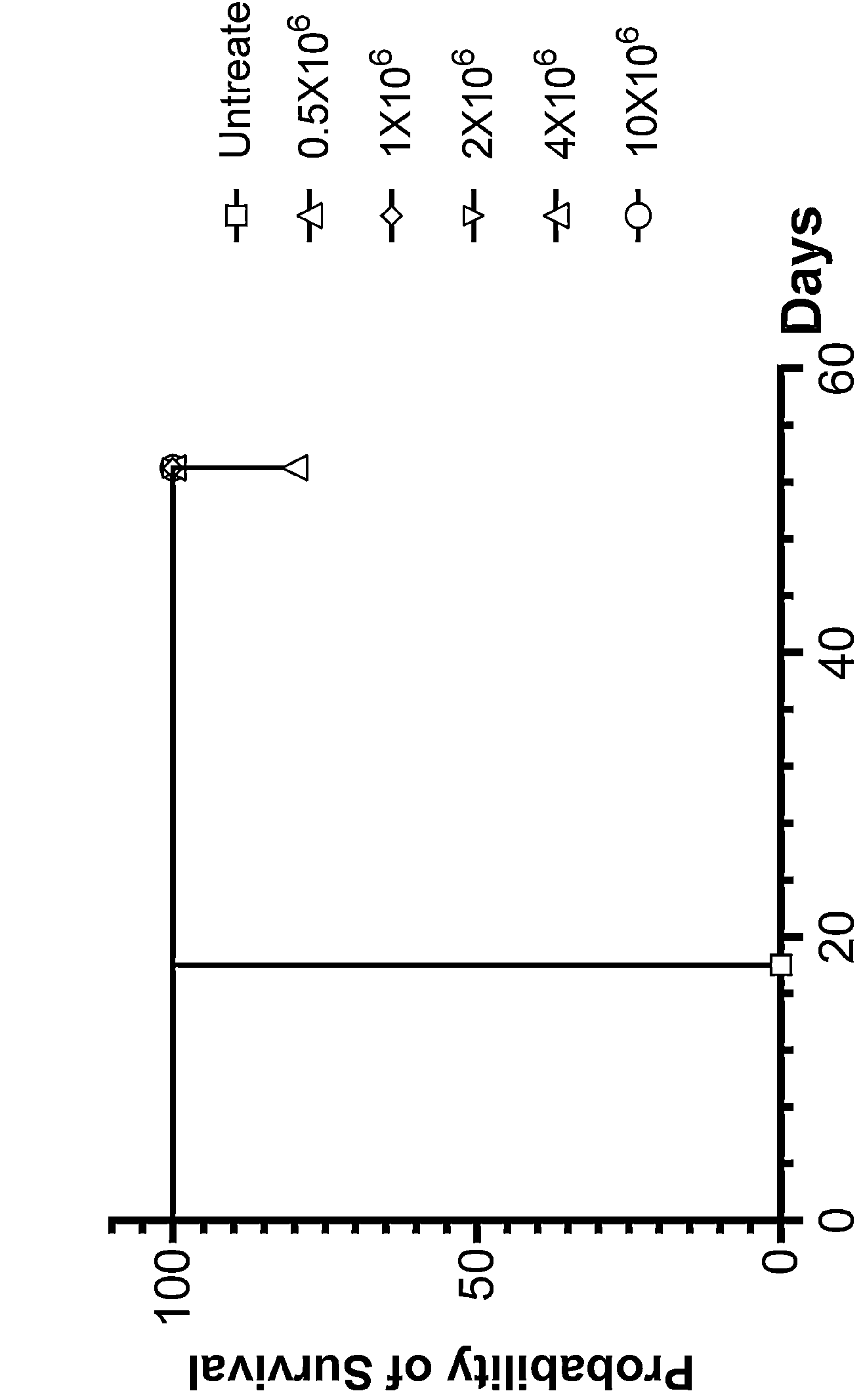

FIGS. 15A-15B include diagrams showing in vivo efficacy in mice inoculated with Raji cells. FIG. 15A: efficacy based on bioluminescence. FIG. 15B: survival rates.

Figure 16A:
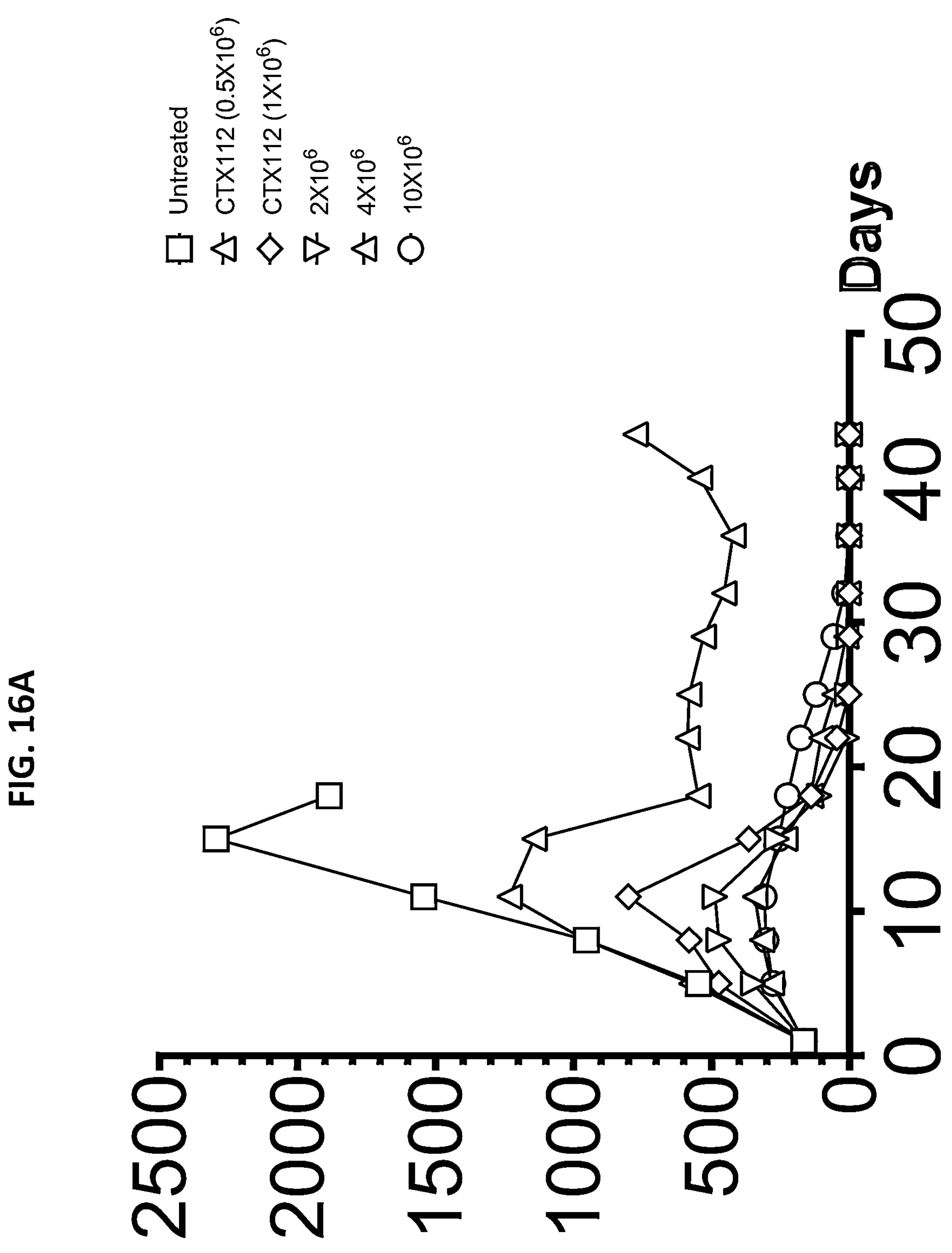
Figure 16B:
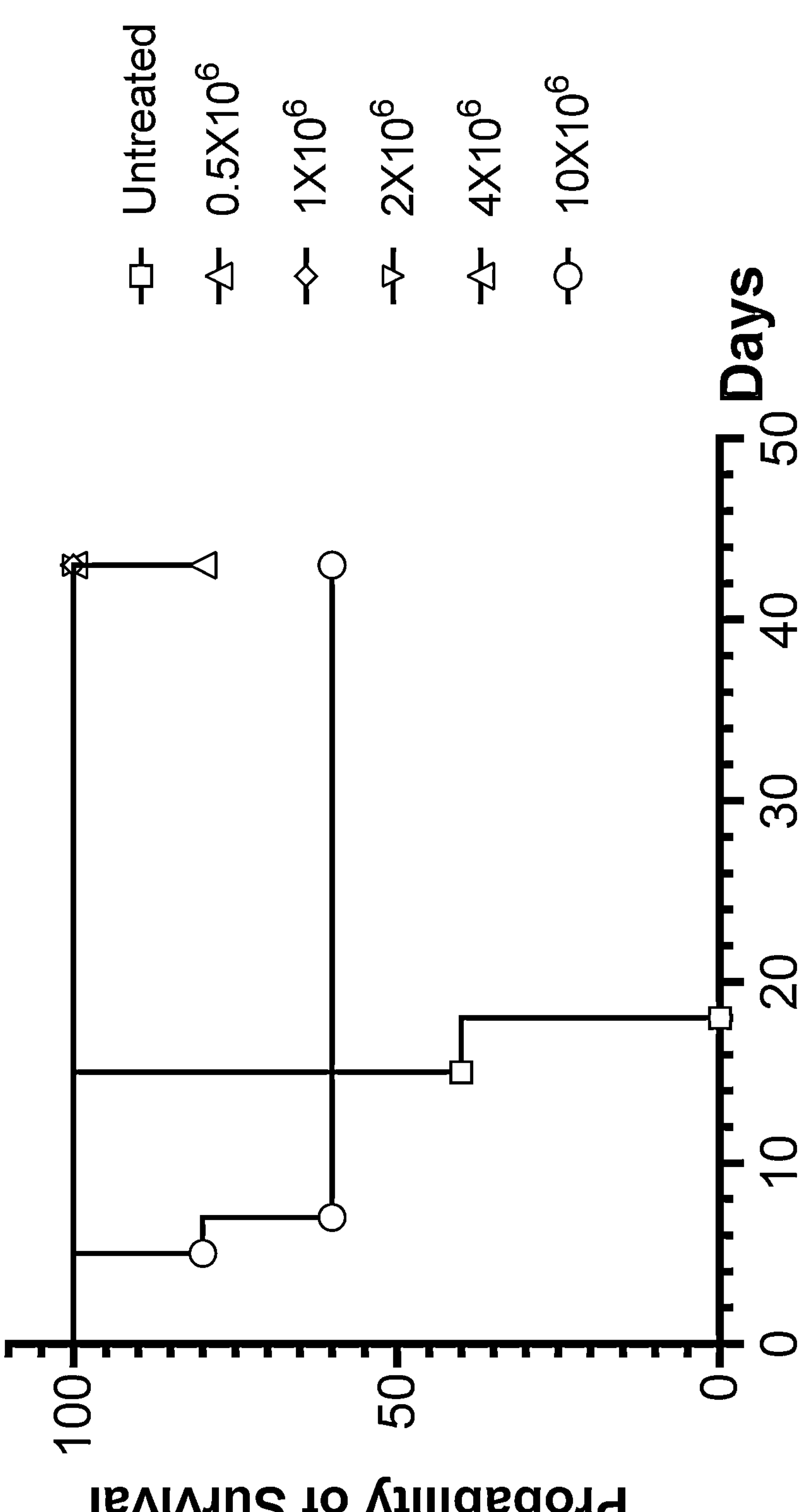

FIGS. 16A-16B include diagrams showing in vivo efficacy in mice inoculated with JeKo cells. FIG. 16A: efficacy based on bioluminescence and FIG. 16B: survival rates.

Figure 17:
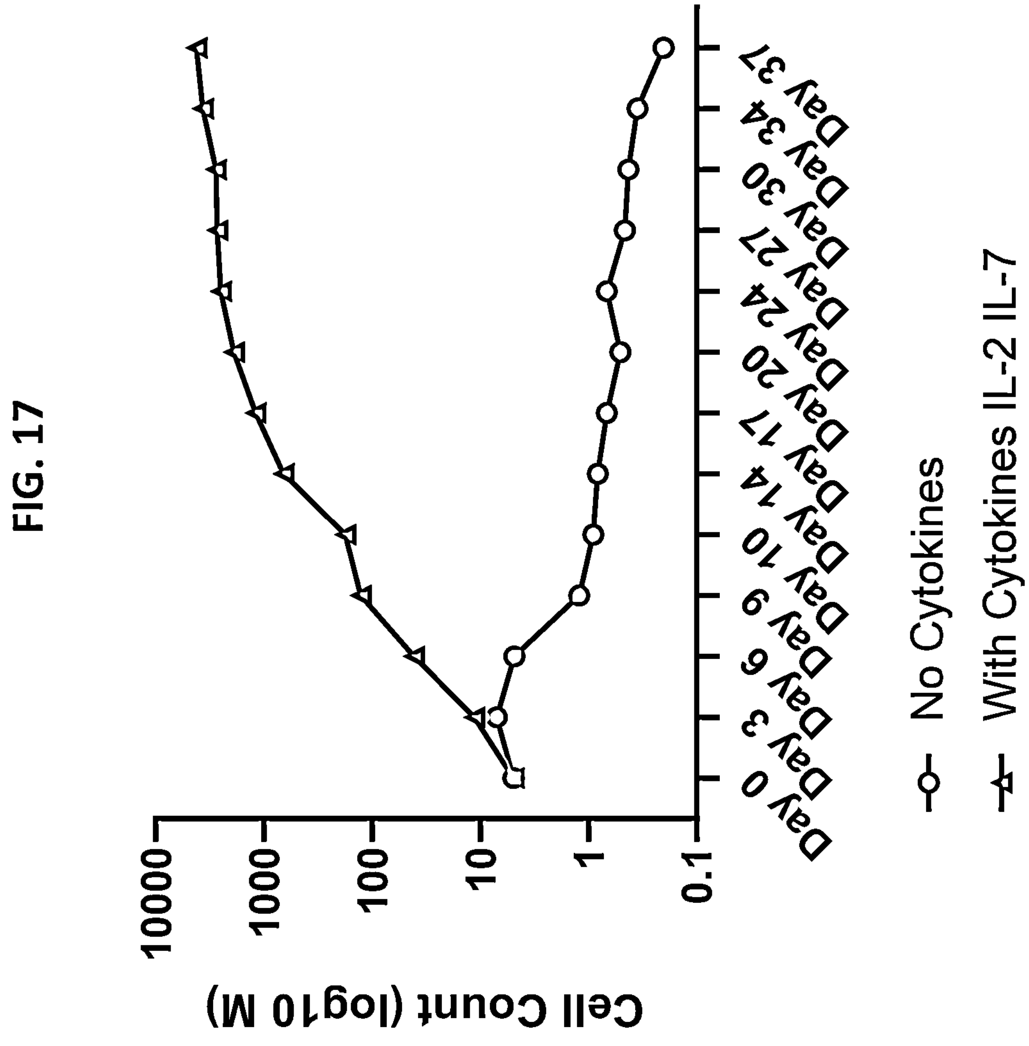

FIG. 17 is a diagram showing cytokine independent growth assay results.

DETAILED DESCRIPTION OF THE INVENTION

The present disclosure is based, at least in part, on the development of advantageous manufacturing processes for producing CAR-T cells, such as anti-CD19 and/or anti-CD70 CAR-T cells, having multiple additional genetic modifications (e.g., disruptions of one or more of Reg1, TGFBRII, TRAC, β2M, and CD70). The methods provided herein allow for effective modification of multiple target genes in T cells, low translocation rates in edited T cells, and high productivity of viable therapeutic T cell products. The improved manufacturing processes disclosed herein led to at least the following advantageous outcomes:

(a) Improved T cell purity and improved T cell viability resulting from the improved T cell enrichment conditions provided herein.

(b) Improved consistency and improved efficiency for producing CAR-expressing T cells resulting from the improved T cell transduction conditions provided herein.

(c) Improved consistency and improved efficiency of gene disruptions in T cells resulting from the improved CRISPR-Cas9-mediated gene editing conditions provided herein.

(d) Increased supply of CAR T-cell therapy resulting from decreased production times and decreased production costs provided by the improved manufacturing processes described herein.

(e) Reduced variability of manufactured drug product resulting from production of uniform and high-quality CAR T-therapies using the improved manufacturing processes described herein.

(f) Simplified AAV transduction condition while maintaining high CAR expression level in T cells.

Accordingly, provided herein are methods for manufacturing genetically engineered T cells expressing a CAR (e.g., an anti-CD19 CAR or an anti-CD70 CAR) and having a disrupted Reg1 gene, a disrupted TGFBRII gene, a disrupted TRAC gene, a disrupted β2M, and optionally a disrupted CD70 gene, via, e.g., the CRISPR/Cas9-mediated gene editing technology.

I. Manufacturing Genetically Engineered T Cells

In some aspects, the present disclosure provides methods for manufacturing genetically engineered CAR-T cells having multiple gene edits, including a disrupted Reg1 gene, a disrupted TGFBRII gene, a disrupted TRAC gene and a disrupted β2M, via, e.g., the CRISPR/Cas gene editing technology. In some instances, the genetically engineered CAR-T cells (e.g., anti-CD70 CAR-T cells) may further include a disrupted CD70 gene. In some instances, the gene editing components may be introduced into T cells (e.g., activated T cells) via multiple electroporation events in a sequential manner. The coding sequence for the CAR construct may be inserted into the disrupted TRAC gene via a donor template, which may be introduced into the T cells using recombinant adeno-associated viral vectors.

A. Source of T Cells

The genetically engineered T cells may be prepared from parent T cells (e.g., non-edited wild-type T cells) obtained from a suitable source, for example, one or more mammal donors. In some examples, the parent non-edited T cells may be obtained from one or more human donors, such as healthy human donors. In some examples, the parent T cells are primary T cells (e.g., non-transformed and terminally differentiated T cells) obtained from one or more human donors (e.g., 2, 3, 4, or 5 human donors). Alternatively, the parent T cells may be differentiated from precursor T cells obtained from one or more suitable donor or stem cells such as hematopoietic stem cells or inducible pluripotent stem cells (iPSC), which may be cultured in vitro.

In some embodiments, the parent T cells can be derived from one or more suitable mammals, for example, one or more human donors. The parent T cells can be obtained from a number of sources, including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, the T cells can be obtained from a unit of blood collected from a subject using any number of techniques known to the skilled person, such as sedimentation, e.g., FICOLL™ separation.

In some instances, the T cell population comprises primary T cells isolated from one or more human donors. Such T cells are terminally differentiated, not transformed, depend on cytokines and/or growth factors for growth, and/or have stable genomes. Alternatively, the T cells may be derived from stem cells (e.g., HSCs or iPSCs) via in vitro differentiation.

In some examples, leukopak samples from suitable a human donor may be used. As known in the art, a leukopak sample is an enriched leukapheresis product collected from peripheral blood. It typically contains a variety of blood cells including monocytes, lymphocytes, platelets, plasma, and red cells. The human donor preferably is a healthy human donor. For example, a human donor candidate may be subject to screening for HBV, HCV, HIV, HTLV, WNV, trypanosome cruzi, and/or CMV. A human subject showing negative results in the screening may be used as a donor for blood cells.

The sources of T-cells that find use in the present methods is not particularly limited. In some embodiments, T cells from a T cell bank can be used as the starting material in any of the manufacturing methods disclosed herein. A T cell bank may comprise T cells with genetic editing of certain genes (e.g., genes involved in cell self renewal, apoptosis, and/or T cell exhaustion or replicative senescence) to improve T cell persistence in cell culture. A T cell bank may be produced from bonafide T cells, for example, non-transformed T cells, terminally differentiated T cells, T cells having stable genome, and/or T cells that depend on cytokines and growth factors for proliferation and expansion. Alternatively, such a T cell bank may be produced from precursor cells such as hematopoietic stem cells (e.g., iPSCs), e.g., in vitro culture. In some examples, the T cells in the T cell bank may comprise genetic editing of one or more genes involved in cell self-renewal, one or more genes involved in apoptosis, and/or one or more genes involved in T cell exhaustion, so as to disrupt or reduce expression of such genes, leading to improved persistence in culture. Compared with the non-edited T counterpart, T cells in a T cell bank may have enhanced expansion capacity in culture, enhanced proliferation capacity, greater T cell activation, and/or reduced apoptosis levels.

B. T Cell Enrichment

In some embodiments, the T cells for use in the manufacturing processes disclosed herein may be enriched from any of the suitable T cell courses disclosed herein via conventional methods or methods disclosed herein. For example, suitable T cells can be enriched from human blood cells using conventional methods or methods disclosed herein.

In some examples, suitable T cells can be isolated from a mixture of immune cells (e.g., those described herein) to produce an isolated T cell population, which may be enriched with one or specific types of T cells. For example, after isolation of peripheral blood mononuclear cells (PBMC), both cytotoxic and helper T lymphocytes can be sorted into naive, memory, and effector T cell subpopulations either before or after activation, expansion, and/or genetic modification. In some instances, the isolated T cell population may be enriched with CD4+ T cells. In other instances, the isolated T cell population may be enriched with CD8+ T cells. In yet other instances, the isolated T cell population may be enriched with CD4+ T cells and CD8+ T cells.

A specific subpopulation of T cells, expressing one or more of the following cell surface markers: TCRαβ, CD3, CD4, CD8, CD27 CD28, CD38 CD45RA, CD45RO, CD62L, CD127, CD122, CD95, CD197, CCR7, KLRG1, MCH-I proteins and/or MCH-II proteins, can be further isolated by positive or negative selection techniques. In some embodiments, a specific subpopulation of T cells, expressing one or more of the markers selected from the group consisting of TCRαβ, CD4 and/or CD8, is further isolated by positive or negative selection techniques. In some embodiments, subpopulations of T cells may be isolated by positive or negative selection prior to genetic engineering and/or post genetic engineering.

An isolated/enriched population of T cells may express one or more of the T cell markers, including, but not limited to a CD3+, CD4+, CD8+, or a combination thereof. In some embodiments, the T cells are isolated from a donor, or subject, and first activated and stimulated to proliferate in vitro prior to undergoing gene editing.

T cells for use in making the genetically engineered T cells may express one or more of the T cell markers, including, but not limited to a $CD4^+$, $CD8^+$, or a combination thereof. In some embodiments, $CD4^+$ T cells can be enriched from human blood cells. In other embodiments, $CD8^+$ T cells can be enriched. In specific examples, both $CD4^+$ and $CD8^+$ T cells are purified from human blood cells.

$CD4^+$ T cells and/or $CD8^+$ T cells can be isolated from a suitable blood cell source, such as those described herein, using any method known in the art or those disclosed herein, for example, using antibodies capable of binding to specific cell-surface biomarkers for the target T cells, e.g., antibodies specific to CD4 and/or antibodies specific to CD8. In some embodiments, enriching $CD4^+$ T cells and $CD8^+$ T cells can be performed using anti-CD4 and anti-CD8 antibodies conjugated to magnetic beads. A cell population comprising $CD4^+$ and $CD8^+$ T cells can be incubated with such magnetic beads under suitable conditions for a suitable period allowing for binding of the target T cells to the magnetic beads via the antibodies conjugated to the beads. Non-bound cells can be washed and $CD4^+$ and $CD8^+$ T cells bound to the beads can be collected using routine methods.

The enriched T cells (e.g., $CD4^+$ T cells and $CD8^+$ T cells) may be evaluated for features such as cell viability and/or purity of the target T cells following routine practice. In some embodiments, the T cell population from the enrichment step disclosed here may have a cell viability of at least about 80% (e.g., at least about 85%, at least about 90%, at least about 95%, or above). Alternatively or in addition to, the enriched T cell population may have a purity of at least about 80% of the target T cells (e.g., $CD4^+$ and/or $CD8^+$ T cells), for example, at least about 85%, at least about 90%, at least about 95%, at least about 97%, about 98% or higher. Alternatively or in addition to, the enriched T cell population may have a purity of at least about 70% of the target T cells (e.g., $CD4^+$ and/or $CD8^+$ T cells), for example, at least about 75%, at least about 80%, at least about 85%, at least about 90%, at least about 95%, at least about 97%, about 98% or higher.

The enriched T cell population (which is also within the scope of the present disclosure) may be used immediately for further processing as disclosed herein. Alternatively, the enriched T cell population may be stored under suitable conditions for future use, for example, via cryopreservation. Prior to further processing, cryopreserved T cells can be thawed following routine procedures. Cell viability of the thawed cells can be assessed to determine whether the thawed cells are suitable for further processing.

T cells from a suitable source can be subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041. In some embodiments, T cells can be activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of the genome editing compositions into the T cells.

In some embodiments, T cells are activated and expanded for about 4 hours, about 6 hours, about 12 hours, about 18 hours, about 24 hours, about 36 hours, about 48 hours, about 60 hours, or about 72 hours prior to introduction of the gene editing compositions into the T cells. In some embodiments, T cells are activated at the same time that genome editing compositions are introduced into the T cells. In some instances, the T cell population can be expanded and/or activated after the genetic editing as disclosed herein. T cell populations or isolated T cells generated by any of the gene editing methods described herein are also within the scope of the present disclosure.

C. T Cell Activation

In some embodiments, the T cells may be activated for a suitable period prior to any of the genetic modifications disclosed herein. For example, the T cells may be activated for about 24 hours to 72 hours before the first gene edit event is performed. In some examples, the T cells can be activated for about 24 hours to 48 hours. In other examples, the T cells can be activated for about 48 hours to about 72 hours. In specific examples, the T cells can be activated for about 48 hours.

T cell activation can be achieved using T cell activating agent or agents, for example, agents that stimulates a CD3/TCR-mediated signaling pathway and/or a co-stimulatory molecule (e.g., CD28) mediated signaling pathway. For example, a T cell activating agent may be a CD3 agonist (e.g., an agonistic anti-CD3 antibody) and activates the CD3/TCR-mediated cell signaling pathway. Alternatively or in addition, a T cell activating agent may be a CD28 agonist (e.g., an anti-CD28 antibody) and activates the co-stimulatory signaling pathway mediated by CD28. Any of the T cell activating agents for use in the method disclosed herein may be conjugated to a support member, such as a nanomatrix particle. In such situations, the T cell activating agents may be conjugated to the same support member. Alternatively, each T cell activating agent may be conjugated to a different support member. In specific examples, the T cell activating agent for use in the method disclosed herein may comprise an anti-CD3 antibody and an anti-CD28 antibody, which may be conjugated to nanomatrix particles. In some embodiments, the T cell activating agent comprises a CD3 agonist and a CD28 agonist attached to a nanomatrix particle. In some embodiments, the CD3 agonist and a CD28 agonist are attached to the same nanomatrix particle. In some embodiments, the CD3 agonist and a CD28 agonist are attached to different nanomatrix particles.

In some embodiments, the T cells can be activated using a commercially available T cell activation agent, for example, TransAct™ (e.g., about 4% to about 8%, for example, about 4%, about 5%, about 6%, about 7% or about 8%). Alternatively or in addition, T cell activation may be performed on the same day (Day 0) when cells are collected/thawed and optionally enriched from a suitable source (e.g., leukopak samples).

To achieve T cell activation, the T cells as disclosed herein, such as enriched T cell (e.g., CD4+/CD8+ T cells), may be placed in a cell culture vessel at a suitable cell seeding density and a suitable cell concentration and incubated in the presence of any of the T cell activating agents disclosed herein for a suitable period to induce T cell activation.

In some instances, ratios of the T cell activating agent to the cell culture medium in the cell culture vessel may range from about 1:10 (v/v) to about 1:15 (v/v). In some examples, the ratio of the T cell activating agent to the cell culture medium in the cell culture vessel may be about 1:10 (v/v), about 1:10.5 (v/v), about 1:11 (v/v), about 1:11.5 (v/v), about 1:12 (v/v), about 1:12.5 (v/v), about 1:13 (v/v), about 1:13.5 (v/v), about 1:14 (v/v), about 1:14.5 (v/v), or about 1:15 (v/v). In specific examples, the ratio of the T cell activating agent to the culture medium in the cell culture vessel is about 1:12.5 (v/v).

Alternatively or in addition, a suitable cell seeding density may be about $1.0\times10^6$ to $2.5\times10^6$ (e.g., $2\times10^6/cm^2$) and a suitable cell concentration may be about $1.0\times10^6$ to $2.5\times10^6$ (e.g., $2\times10^6$/ml). The T cells may be incubated with the T cell activating agent (e.g., an anti-CD3 antibody and an anti-CD28 antibody, both of which may be immobilized on a nanomatrix) for a suitable period as disclosed herein, for example, about 24 to 72 hours, for example. In some examples, the T cells may be incubated with the T cell activating agent for about 48 hours.

Alternatively or in addition, a suitable cell seeding density may be about $1.5\times10^6$ to $2.5\times10^6$ (e.g., $2\times10^6/cm^2$) and a suitable cell concentration may be about $1.5\times10^6$ to $2.5\times10^6$ (e.g., $2\times10^6$/ml). The T cells may be incubated with the T cell activating agent (e.g., an anti-CD3 antibody and an anti-CD28 antibody, both of which may be immobilized on a nanomatrix) for a suitable period as disclosed herein, for example, about 24 to 72 hours, for example. In some examples, the T cells may be incubated with the T cell activating agent for about 48 hours.

In some embodiments, the cell culture vessel may be a static culture vessel, which would allow for relatively large-scale production of the genetically engineered T cells as disclosed herein. Compared to conventional cell culture flasks, static cell culture vessels allow T cells to reside on a highly gas permeable membrane submerged under medium that supplies oxygen and nutrients to the T cells without mixing or shaking. Static culture vessels allow T cell manufacturing without medium change. Accordingly, in some embodiments, the T cell activation process in any of the methods disclosed herein may involve no medium change.

When needed, the activating agent may be removed from the cell culture vessel or diluted prior to the downstream or follow-on gene editing events to minimize any potential impact that the activating agent may confer during gene editing. In some embodiments, the activating agent can be removed from the cell culture vessel using routine methods, e.g., centrifugation. Alternatively, the activating agent may be diluted in the cell culture vessel prior to gene editing, e.g., diluted by addition of media to the cell culture vessel.

In some embodiments, the activated T cells derived from any of the T cell activation processes disclosed herein may be cultured overnight (e.g., about 16 hours) to allow T cells to recover prior to gene editing. In some instances, a culture of activated T cells may still contain the T cell activating agent. In other instances, the culture of activated T cells may have little or no presence of the T cell activating agent. Alternatively, the activated T cells derived from any of the T cell activation processes disclosed herein may be used directly for gene editing without culturing.

D. CRISPR-Cas9-Mediated Gene Editing

The T cells obtained from a suitable source as disclosed herein can be used for gene editing as also disclosed herein via the CRISPR-Cas9-mediated gene editing technology. In some instances, the T cells subject to the gene editing can be enriched, for enriched with CD4+ T cells, CD8+ T cells, or a combination thereof. Alternatively, the T cells can be activated (e.g., for about 48 hours) prior to the gene editing.

The T cells prepared by any of the procedures disclosed herein may be subjected to gene editing to disrupt the Regnase-1 (Reg1) gene, the TGFBRII gene, the TRAC gene, the β2M gene, and optionally the CD70 gene and to incorporate a nucleic acid encoding a CAR such as an anti-CD19 CAR or an anti-CD70 CAR via CRISPR-Cas9-mediated gene editing. In some instances, components for gene disruptions, for example, Cas9 enzymes and guide RNAs specific to the target genes may be delivered to the T cells via electroporation (e.g., single or multiple). In some examples, the components can be delivered to the T cells via two sequential electroporation events. As examples, specific pairing of gRNAs and order for delivering the multiple gRNAs (e.g., in RNP complex form with the Cas9 enzyme) in the two sequential electroporation events can achieve superior results, for example, high gene editing rates and low translocation rates. See, e.g., Example 4 below.

(a) CRISPR-Cas9-Mediated Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an acronym for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

Cas9

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood, that wild-type Cas9 may be used or modified versions of Cas9 may be used (e.g., evolved versions of Cas9, or Cas9 orthologues or variants), as provided herein. In some embodiments, Cas9 comprises a *Streptococcus pyogenes*-derived Cas9 nuclease protein that has been engineered to include C- and N-terminal SV40 large T antigen nuclear localization sequences (NLS). The resulting Cas9 nuclease (sNLS-spCas9-sNLS) is a 162 kDa protein that is produced by recombinant *E. coli* fermentation and purified by chromatography. The spCas9 amino acid sequence can be found as UniProt Accession No. Q99ZW2, which is provided herein as SEQ ID NO: 1 (see Table 8 below).

Guide RNAs (gRNAs)

CRISPR-Cas9-mediated gene editing as described herein includes the use of a guide RNA or a gRNA. As used herein, a "gRNA" refers to a genome-targeting nucleic acid that can direct the Cas9 to a specific target sequence within a target gene (e.g., a Reg1 gene, a TGFBRII gene, a TRAC gene or a β2M gene) for gene editing at the specific target sequence. A guide RNA comprises at least a spacer sequence that hybridizes to a target nucleic acid sequence within a target gene for editing, and a CRISPR repeat sequence.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

A spacer sequence in a gRNA is a sequence (e.g., a 20-nucleotide sequence) that defines the target sequence (e.g., a DNA target sequences, such as a genomic target sequence) of a target gene of interest. In some embodiments, the spacer sequence ranges from 15 to 30 nucleotides. For example, the spacer sequence may contain 15, 16, 17, 18, 19, 29, 21, 22, 23, 24, 25, 26, 27, 28, 29, or 30 nucleotides. In some embodiments, a spacer sequence contains 20 nucleotides.

The "target sequence" is in a target gene that is adjacent to a PAM sequence and is the sequence to be modified by an RNA-guided nuclease (e.g., Cas9). The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence. For example, if the Reg1 gene target sequence is 5'-ACGACGCGTGGGTGGCAAGC-3' (SEQ ID NO: 23), then the gRNA spacer sequence is 5'-ACGACGCGUGGGUGGCAAGC-3' (SEQ ID NO: 5). See also Table 3. The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence is the *S. pyogenes* PAM.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be an sgRNA, which may comprise a 20-nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence. Examples are provided in Table 3 below. In these exemplary sequences, the fragment of "n" refers to the spacer sequence at the 5' end.

In some embodiments, the sgRNA comprises no uracil at the 3' end of the sgRNA sequence. In other embodiments, the sgRNA may comprise one or more uracil residues at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as an sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art. In some embodiments, non-natural modified nucleobases can be introduced into any of the gRNAs disclosed herein during synthesis or post-synthesis. In certain embodiments, modifications are on internucleoside linkages, purine or pyrimidine bases, or sugar. In some embodiments, a modification is introduced at the terminal of a gRNA with chemical synthesis or with a polymerase enzyme. Examples of modified nucleic acids and their synthesis are disclosed in WO2013/052523. Synthesis of modified polynucleotides is also described in Verma and Eckstein, Annual Review of Biochemistry, vol. 76, 99-134 (1998).

In some embodiments, enzymatic or chemical ligation methods can be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

It should be understood that more than one suitable Cas9 and more than one suitable gRNA can be used in methods described herein, for example, those known in the art or disclosed herein. In some embodiments, methods comprise a Cas9 enzyme and/or a gRNA known in the art. Examples can be found in, e.g., in WO 2019/097305A2, and WO2019/215500, the relevant disclosures of each of the prior applications are herein incorporated by reference for the purposes and subject matter referenced herein.

(b) Target Genes and RNA Guides

In some embodiments, the manufacturing methods disclosed herein involving gene editing of one or more of Reg1, TGFBRII, TRAC, β2M, and CD70 genes.

Regnase-1 (Reg1) Gene Editing

Reg1 contains a zinc finger motif, binds RNA and exhibits ribonuclease activity. Reg1 plays roles in both immune and non-immune cells and its expression can be rapidly induced under diverse conditions including microbial infections, treatment with inflammatory cytokines and chemical or mechanical stimulation. Human Reg1 gene is located on chromosome 1p34.3. Additional information can be found in GenBank under Gene ID: 80149.

In some embodiments, the gRNAs targeting a Reg1 gene may target a site within exon 1, exon 2, exon 3, exon 4, exon 5, or exon 6 of the Reg1 gene. In some examples, the gRNA targeting the Reg1 gene may target exon 2. In other examples, the gRNA targeting the Reg1 gene may target exon 4. Such a gRNA may comprise a spacer sequence complementary (complete or partially) to the target sequences in, e.g., exon 2 or exon 4 of a Reg1 gene, or a fragment thereof. Exemplary target sequences of Reg1 and exemplary gRNA sequences are provided in Table 3 below.

In some embodiments, gRNAs targeting the Reg1 genomic region and Cas9 create breaks in the Reg1 genomic region resulting in Indels in the Reg1 gene disrupting expression of the mRNA or protein. In some embodiments, gRNAs targeting the Reg1 genomic region create Indels in the Reg1 gene comprising at least one nucleotide sequence selected from the sequences in Table 7. In some embodiments, gRNA (SEQ ID NO: 3) targeting the Reg1 genomic region creates Indels in the Reg1 gene comprising at least one nucleotide sequence selected from the sequences in Table 7.

TGFBRII Gene Editing

TGFBRII gene, which encodes Transforming Growth Factor Receptor Type II (TGFBRII). TGFBRII receptors are a family of serine/threonine kinase receptors involved in the TGFβ signaling pathway. These receptors bind growth factor and cytokine signaling proteins in the TGFβ family, for example, TGFβs (TGFβ1, TGFβ2, and TGFβ3), bone morphogenetic proteins (BMPs), growth differentiation factors (GDFs), activin and inhibin, myostatin, anti-Müllerian hormone (AMH), and NODAL.

In some embodiments, the gRNAs targeting a TGFBRII gene may target a site within exon 1, exon 2, exon 3, exon 4, exon 5, or exon 6 of the TGFBRII gene. In some examples, the gRNA targeting the TGFBRII gene may target exon 2. In other examples, the gRNA targeting the TGFBRII gene may target exon 4. Such a gRNA may comprise a spacer sequence complementary (complete or partially) to the target sequences in, e.g., exon 2 or exon 4 of a TGFBRII gene. Exemplary target sequences of TGFBRII and exemplary gRNA sequences are provided in Table 3 below.

In some embodiments, gRNAs targeting the TGFBRII genomic region and Cas9 create breaks in the TGFBRII genomic region resulting in Indels in the TGFBRII gene disrupting expression of the mRNA or protein.

TRAC Gene Editing

This disruption leads to loss of function of the TCR and renders the engineered T cell non-alloreactive and suitable for allogeneic transplantation, minimizing the risk of graft versus host disease. In some embodiments, expression of the endogenous TRAC gene is eliminated to prevent a graft-versus-host response. See also WO2019097305, the relevant disclosures of which are incorporated by reference herein for the purpose and subject matter referenced herein.

An exemplary gRNA targeting a TRAC gene is provided in Table 3 below. See also WO2019/097305A2, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22,552,154. Ensembl; ENSG00000277734).

In some embodiments, gRNAs targeting the TRAC genomic region and Cas9 create breaks in the TRAC genomic region resulting in Indels in the TRAC gene disrupting expression of the mRNA or protein. In some embodiments, gRNAs targeting the TRAC genomic region create Indels in the TRAC gene comprising at least one nucleotide sequence selected from the sequences in Table 4. In some embodiments, gRNA (SEQ ID NO: 11) targeting the TRAC genomic region creates Indels in the TRAC gene comprising at least one nucleotide sequence selected from the sequences in Table 4.

β2M Gene Editing 32M is a common (invariant) component of MHC I complexes. Disrupting its expression by gene editing will prevent host versus therapeutic allogeneic T cells responses leading to increased allogeneic T cell persistence. In some embodiments, expression of the endogenous β2M gene is eliminated to prevent a host-versus-graft response.

An exemplary gRNA targeting a β2M gene is provided in Table 3 below. See also WO2019/097305A2, the relevant disclosures of which are incorporated by reference herein for the purpose and subject matter referenced herein. Other gRNA sequences may be designed using the β2M gene sequence located on Chromosome 15 (GRCh38 coordinates: Chromosome 15: 44,711,477-44,718,877; Ensembl: ENSG00000166710).

In some embodiments, gRNAs targeting the β2M genomic region and RNA-guided nuclease create breaks in the β2M genomic region resulting in Indels in the β2M gene disrupting expression of the mRNA or protein. In some embodiments, gRNAs targeting the β2M genomic region create Indels in the β2M gene comprising at least one nucleotide sequence selected from the sequences in Table 5. In some embodiments, gRNA (SEQ ID NO: 15) targeting the β2M genomic region creates Indels in the β2M gene comprising at least one nucleotide sequence selected from the sequences in Table 5.

CD70 Gene Editing

T cell exhaustion is a process of stepwise and progressive loss of T cell functions, which may be induced by prolonged antigen stimulation or other factors. Genes involved in T cell exhaustion refer to those that either positively regulate or negatively regulate this biological process. The genetically engineered T cells disclosed herein may comprise genetic editing of a gene that positively regulates T cell exhaustion to disrupt its expression. Alternatively or in addition, the genetically engineered T cells may comprise genetic editing of a gene that negatively regulates T cell exhaustion to enhance its expression and/or biologic activity of the gene product.

It was also found that disrupting the CD70 gene in immune cells engineered to express an antigen targeting moiety enhanced anti-tumor efficacy against large tumors and induced a durable anti-cancer memory response. Specifically, the anti-cancer memory response prevented tumor growth upon re-challenge. Further, it has been demonstrated disrupting the CD70 gene results in enhanced cytotoxicity of immune cells engineered to express an antigen targeting moiety at lower ratios of engineered immune cells to target cells, indicating the potential efficacy of low doses of engineered immune cells. See, e.g., WO2019/215500, the relevant disclosures of which are incorporated by reference for the purpose and subject matter referenced herein.

Structures of CD70 genes are known in the art. For example, human CD70 gene is located on chromosome 19p13.3. The gene contains four protein encoding exons. Additional information can be found in GenBank under Gene ID: 970.

In some embodiments, the gRNAs targeting a CD70 gene may target a site within exon 1 or exon 3 of a CD70 gene. Such a gRNA may comprise a spacer sequence complementary (complete or partially) to the target sequences in exon 1 or exon 3 of a CD70 gene. Exemplary target sequences in a CD70 gene and exemplary gRNAs specific to the CD70 gene are provided in Table 3 below.

In some embodiments, gRNAs targeting the CD70 genomic region and RNA-guided nuclease create breaks in the CD70 genomic region resulting in Indels in the CD70 gene disrupting expression of the mRNA or protein. In some embodiments, gRNAs targeting the CD70 genomic region create Indels in the CD70 gene comprising at least one nucleotide sequence selected from the sequences in Table 6. In some embodiments, gRNA (SEQ ID NO: 19) targeting the CD70 genomic region creates Indels in the CD70 gene comprising at least one nucleotide sequence selected from the sequences in Table 6.

(c) Delivery of Guide RNAs and Nucleases to T Cells

The CRISPR/Cas nuclease system disclosed herein, comprising one or more gRNAs and at least one RNA-guided nuclease (e.g., a Cas9 enzyme), optionally a donor template as disclosed below, can be delivered to a target cell (e.g., a T cell) for genetic editing of a target gene, via a conventional method. In some embodiments, components of a CRISPR/Cas nuclease system as disclosed herein may be delivered to a target cell separately, either simultaneously or sequentially. In other embodiments, the components of the CRISPR/Cas nuclease system may be delivered into a target together, for example, as a complex. In some instances, gRNA and a RNA-guided nuclease can be pre-complexed together to form a ribonucleoprotein (RNP), which can be delivered into a target cell.

RNPs are useful for gene editing, at least because they minimize the risk of promiscuous interactions in a nucleic acid-rich cellular environment and protect the RNA from degradation. Methods for forming RNPs are known in the art. In some embodiments, an RNP containing an RNA-guided nuclease (e.g., a Cas nuclease, such as a Cas9 nuclease) and one or more gRNAs targeting one or more genes of interest can be delivered a cell (e.g., a T cell). In some embodiments, an RNP can be delivered to a T cell by electroporation.

In some embodiments, an RNA-guided nuclease can be delivered to a cell in a DNA vector that expresses the RNA-guided nuclease in the cell. In other examples, an RNA-guided nuclease can be delivered to a cell in an RNA that encodes the RNA-guided nuclease and expresses the nuclease in the cell. Alternatively or in addition, a gRNA targeting a gene can be delivered to a cell as a RNA, or a DNA vector that expresses the gRNA in the cell.

Delivery of an RNA-guided nuclease, gRNA, and/or an RNP may be through direct injection or cell transfection using known methods, for example, electroporation or chemical transfection. Other cell transfection methods may be used.

In some embodiments, the multiple gRNAs and the one or more RNA-guided nucleases such as Cas9 enzymes disclosed herein may be delivered to the T cells by electroporation, either in a single electroporation event or in multiple ones (e.g., two sequential electroporation events). In each electroporation, a suitable amount of the T cells disclosed herein (e.g., activated T cells) may be mixed with a suitable amount of one or more gRNAs and one or more RNA-guided nucleases (e.g., Cas9 enzymes). The mixture thus formed may be placed in a vial suitable for electroporation, which can be placed in an electroporator. The T cells for use in electroporation may be placed in multiple cell cassettes, depending upon the electroporation instrument used. Suitable electroporation instruments are known to those skilled in the art and could include static and flow electroporators, including the Lonza Nucleofector®, Maxcyte® GT, and MaxCyte® GTx. In some instances, multiple cell cassettes may be used in an electroporation process. More details are provided in Example 5 below.

Electroporation may be performed following conventional approaches or guidance provided herein. After an electroporation event, the T cells may be collected for further processing, for example, for T cell recovery and expansion and/or for further electroporation. In some instances, the cells may be cultured in a fresh medium for a suitable period for recovery after electroporation. Gene editing efficiency may be determined following routine practice. The genetically edited T cells thus produced may be subjected to viral vector transduction for delivery of a nucleic acid configured for CAR expression.

In some instances, the amount of the T cells used in each electroporation may range from about $100\times10^6$ cells/mL to about $400\times10^6$ cells/mL. For example, a suitable amount of the T cells for the first electroporation step may range from about $200\times10^6$ cells/mL to about $350\times10^6$ cells/mL. In some embodiments, the concentration of the enriched T cells may be about $100\times10^6$ cells/mL. In some embodiments, the concentration of enriched T cells may be about $200\times10^6$ cells/mL. In some embodiments, the concentration of enriched T cells may be about $300\times10^6$ cells/mL or about $350\times10^6$ cells/mL.

The amounts of RNA-guided nucleases (e.g., Cas9 enzymes) and the gRNAs forming RNPs with the Cas9 enzyme in each electroporation may vary, depending on the type of nucleases and the type and number of the gRNAs that form the RNP(s). Some examples are provided herein. See, e.g., Examples 2 and 3 below.

In some embodiments, the methods disclosed herein may involve two sequential electroporation events for delivering the RNA-guided nucleases (e.g., Cas9 enzymes) and the multiple gRNAs targeting the Reg1 gene, the TGFBRII gene, the TRAC gene, the β2M gene, and optionally the CD70 gene. The first electroporation event comprises a first CRISPR/Cas9 gene editing system and the second electroporation event comprises a second CRISPR/Cas9 gene editing system. Each CRISPR/Cas9 gene editing system comprises one or more RNA-guided nucleases (e.g., Cas9 enzymes), which can be identical or different, and one or more gRNAs targeting one or more of the listed genes of interest. The nucleases and the gRNAs may form one RNP complex. Alternatively, the nucleases and the gRNAs may form multiple RNP complexes, which can be mixed for electroporation. Some specific examples are provided below.

In some examples, the first electroporation event of a method as disclosed herein may be performed on the same day (Day 0) when the parent T cells are collected/thawed and optionally enriched and/or activated. In some examples, the first electroporation event may be performed on Day 1, for example, after T cell activation for up to 24 hours. In some examples, the first electroporation event may be performed on Day 2, for example, after T cell activation for up to 48 hours. In some examples, the first electroporation event may be performed on Day 3, for example, after T cell activation for up to 72 hours. In some examples, the first electroporation event may be performed on Day 4.

(d) Exemplary Gene Editing for an Edited Anti-CD19 CAR T Cell Product

Figure 5:
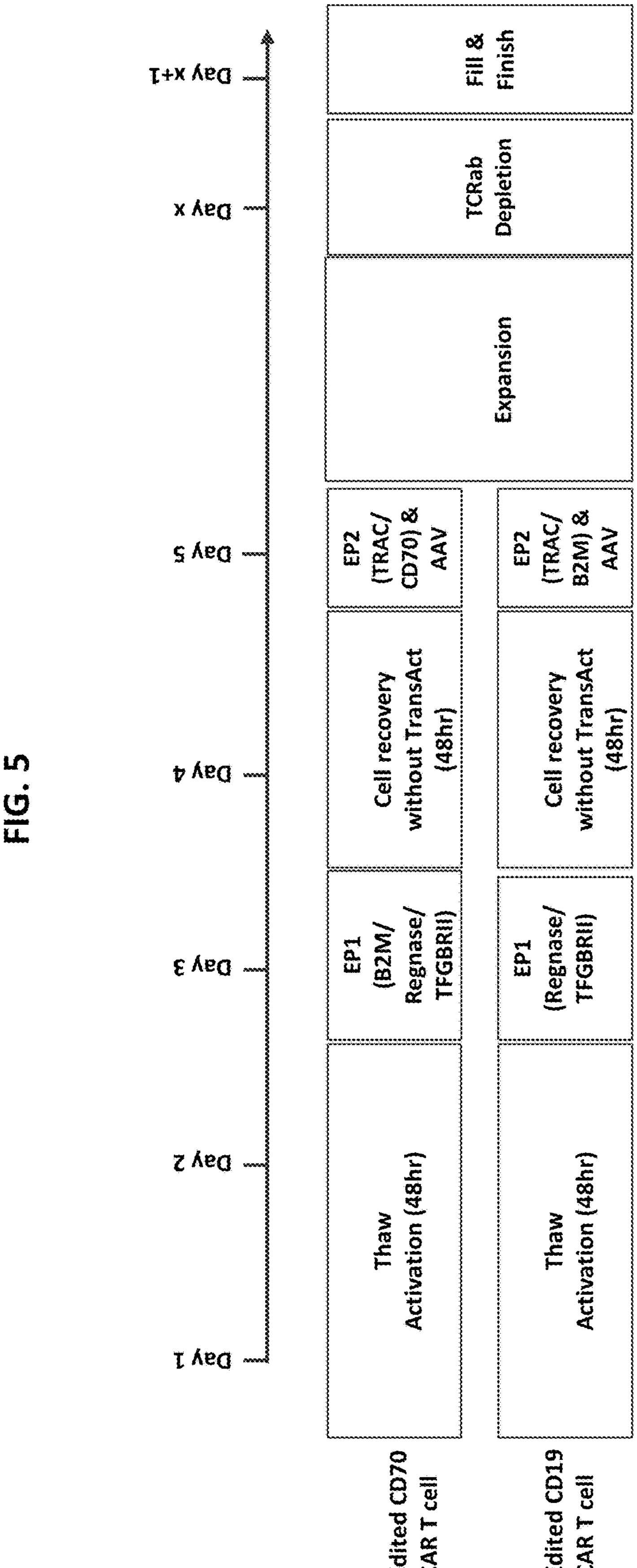
FIG. 5 is a schematic illustration depicting exemplary manufacturing processes for preparing edited anti-CD70 CAR T cells and edited anti-CD19 CAR cells.

An edited anti-CD19 CAR T cell product is a CD19-directed T cell immunotherapy comprised of allogeneic T cells that are genetically modified ex vivo using CRISPR/Cas9 (Clustered Regularly Interspaced Short Palindromic Repeats/CRISPR associated protein 9) gene editing components (sgRNA and Cas9 nuclease). The modifications include targeted disruption of TRAC, β2M, TFGBRII, and Reg1. Gene editing to introduce these genetic modifications may be performed by two sequential electroporation steps. In the first electroporation step, an RNP complex comprising a Cas9 enzyme (e.g., SEQ ID NO:1), a sgRNA targeting the Reg1 gene, and a sgRNA targeting the TGFBRII gene (see Table 3 below for exemplary sgRNAs) can be delivered to the activated T cells. In the second electroporation step, a mixture of RNP complexes each comprising a Cas9 enzyme (e.g., SEQ ID NO:1) and a sgRNA targeting the TRAC gene or the β2M gene (see Table 3 below for exemplary sgRNAs) can be delivered to T cells recovered from the first electroporation step. This gene delivery approach allows for high gene editing efficiency and low translocation rates. FIGS. 4 and 5 provide exemplary illustrations of this two-step electroporation approach. Examples of this approach are also provided below.

In some embodiments, a T cell population enriched with CD4+ T cells and CD8+ T cells may be activated following the disclosures provided herein to produce a population of activated T cells. The activated T cells are subject to a first electroporation to deliver an RNP comprising a Cas9 enzyme (e.g., SEQ ID NO:1), a sgRNA targeting the Reg1 gene, and a sgRNA targeting the TGFBRII gene (see Table 3 below for exemplary sgRNAs). In some instances, the activated T cells used in the first electroporation may range from about $1\times10^8$ cells/ml to about $5\times10^8$ cells/ml; optionally about $3\times10^8$ cells/ml. For example, the amount of the activated T cells for the first electroporation step may range from about $2\times10^8$ cells/mL to about $3\times10^8$ cells/mL. In some examples, the amount of the activated T cells may be about $1\times10^8$ cells/mL. In some examples, the amount of the activated T cells may be about $2\times10^8$ cells/mL. In some examples, the amount of the activated T cells may be about $3\times10^8$ cells/mL.

In the first electroporation step, the sgRNAs targeting TGFBRII and Reg1 may form two separate RNPs with a Cas9 enzyme (which may be identical in the two RNPs). Two RNP complexes may be mixed to form a mixture, which can be used for electroporation. In some instances, the two RNP complexes may contain the same amount of the Cas9 enzyme. For example, both RNP complexes may comprise about 0.1-0.3 mg/ml (e.g., about 0.120-0.150 mg/ml) of the Cas9 enzyme (e.g., the Cas9 enzyme of SEQ ID NO:1). In some examples, each of the RNP complexes may comprise about 0.120 to about 0.150 mg/ml of the Cas9 enzyme, which may be the Cas9 enzyme of SEQ ID NO:1. In other embodiments, the two RNP complexes may contain different amounts of the Cas9 enzyme. In some examples, the RNP complex targeting the TGFBRII gene may comprise a higher amount of the Cas9 enzyme relative to the RNP complex targeting the Reg1 gene. Alternatively, the RNP complex targeting the Reg1 gene may comprise a higher amount of the Cas9 enzyme relative to the RNP complex targeting the TGFBRII gene. For example, the RNP complex targeting the TGFBRII gene may comprise 0.120 mg/ml of the Cas9 enzyme and/or the RNP complex targeting the Reg1 gene may comprise 0.150 mg/ml of the Cas9 enzyme.

In some instances, the Cas9 enzyme and the gRNA targeting Reg1 may be at a weight ratio of 4:1 to 1:4. In some examples, the weight ratio may be 2:1 to 1:2. In specific examples, the Cas9 enzyme and the gRNA targeting Reg1 may be at a weight ratio of 4:1, 3:1, 2:1, 1:1, 1:2, 1:3, or 1:4. Alternatively or in addition, the Cas9 enzyme and the gRNA targeting TGFBRII may be at a weight ratio of 4:1 to 1:4. In some examples, the weight ratio may be 2:1 to 1:2. In specific examples, the Cas9 enzyme and the gRNA targeting TGFBRII may be at a weight ratio of 4:1, 3:1, 2:1, 1:1, 1:2, 1:3, or 1:4.

In some examples, the Cas9 enzyme for each RNP (e.g., the Cas9/Reg1 gRNA RNP or the Cas9/TGFBRII gRNA RNP) may have a concentration of about 40 μg/ml to about 180 μg/ml, for example, about 60 μg/ml to about 160 μg/ml, about 80 μg/ml to about 140 μg/ml, or about 100 μg/ml to about 120 μg/ml. In some examples, the Cas9 enzyme may have a concentration of about 120 μg/ml. In some examples, the Cas9 enzyme may have a concentration of about 100 μg/ml. In some examples, the Cas9 enzyme may have a concentration of about 110 μg/ml. In some examples, the Cas9 enzyme may have a concentration of about 120 μg/ml. In some examples, the Cas9 enzyme may have a concentration of about 130 μg/ml. In some examples, the Cas9 enzyme may have a concentration of about 140 μg/ml. In some examples, the Cas9 enzyme may have a concentration of about 150 μg/ml. In some examples, the Cas9 enzyme may have a concentration of about 160 μg/ml. In some examples, the Cas9 enzyme may have a concentration of about 170 μg/ml. In some examples, the Cas9 enzyme may have a concentration of about 180 μg/ml.

In some examples, the gRNA targeting Reg1 may have a concentration of about 40 μg/ml to about 160 μg/ml, for example, about 60 μg/ml to about 140 μg/ml, about 80 μg/ml to about 120 μg/ml, or about 100 μg/ml to about 150 μg/ml. In some examples, the gRNA targeting Reg1 may have a concentration of about 100 μg/ml. In some examples, the gRNA targeting Reg1 may have a concentration of about 110 μg/ml. In some examples, the gRNA targeting Reg1 may have a concentration of about 120 μg/ml. In some examples, the gRNA targeting Reg1 may have a concentration of about 130 μg/ml. In some examples, the gRNA targeting Reg1 may have a concentration of about 140 μg/ml.

Alternatively or in addition, the gRNA targeting TGFBRII may have a concentration of about 40 μg/ml to about 160 μg/ml, for example, about 60 μg/ml to about 140 μg/ml, about 80 μg/ml to about 120 μg/ml, or about 100 μg/ml to about 150 μg/ml. In some examples, the gRNA targeting TGFBRII may have a concentration of about 100 μg/ml. In some examples, the gRNA targeting TGFBRII may have a concentration of about 110 μg/ml. In some examples, the gRNA targeting TGFBRII may have a concentration of about 120 μg/ml. In some examples, the gRNA targeting TGFBRII may have a concentration of about 130 μg/ml. In some examples, the gRNA targeting TGFBRII may have a concentration of about 140 μg/ml.

In some specific examples, the Cas9 enzyme used in the first electroporation step may have a total concentration of about 250 μg/ml to about 300 μg/ml (e.g., about 270 μg/ml), the gRNA targeting Reg1 may have a concentration of about 100 μg/ml to about 130 μg/ml (e.g., about 120 μg/ml), and the gRNA targeting the TGFBRII gene may have a concentration of about 100 μg/ml to about 130 μg/ml (e.g., about 120 μg/ml).

The T cells after the first electroporation can be collected and cultured in a medium for a suitable period for T cell recovery. In some instances, the T cells may be cultured for about 24-72 hours. In one example, the T cells may be cultured for 48 hours. In this recovery stage, the culture medium may be free of T cell activating agent, such as those disclosed herein (e.g., CD3 agonists and/or CD28 agonists).

The recovered T cells can then be subject to the second electroporation step for delivering RNPs comprising the Cas9 enzyme and the sgRNAs targeting TRAC and β2M. In some instances, the recovered T cells used in the second electroporation may range from about $1\times10^8$ cells/ml to about $5\times10^8$ cells/ml; optionally about $3\times10^8$ cells/ml. For example, the amount of the activated T cells for the first electroporation step may range from about $2\times10^8$ cells/mL to about $3\times10^8$ cells/mL. In some examples, the amount of the activated T cells may be about $1\times10^8$ cells/mL. In some examples, the amount of the activated T cells may be about $2\times10^8$ cells/mL. In some examples, the amount of the activated T cells may be about $3\times10^8$ cells/mL.

In the second electroporation step, the sgRNAs targeting TRAC and β2M may form two separate RNPs with a Cas9 enzyme (which may be identical in the two RNPs). Two RNP complexes may be mixed to form a mixture, which can be used for electroporation. In some instances, the two RNP complexes may contain the same amount of the Cas9 enzyme. For example, both RNP complexes may comprise about 0.1-0.3 mg/ml (e.g., about 0.1-0.2 mg/ml) of the Cas9 enzyme (e.g., the Cas9 enzyme of SEQ ID NO:1). In some examples, each of the RNP complexes may comprise about 0.15 mg/ml of the Cas9 enzyme, which may be the Cas9 enzyme of SEQ ID NO:1. In other embodiments, the two RNP complexes may contain different amounts of the Cas9 enzyme. In some examples, the RNP complex targeting the TRAC gene may comprise a higher amount of the Cas9 enzyme relative to the RNP complex targeting the β2M gene. Alternatively, the RNP complex targeting the β2M gene may comprise a higher amount of the Cas9 enzyme relative to the RNP complex targeting the TRAC gene.

Alternatively or in addition, the two RNP complexes may comprise the same amount of the gRNAs (one targeting TRAC and the other targeting MM). Alternatively, the two RNP complexes may comprise different amounts of the gRNAs. For example, the amount of the gRNA targeting the TRAC gene may range from about 0.035 mg/ml to about 0.8 mg/ml, for example, about 50 μg/ml to about 80 μg/ml. In specific examples, the amount of the gRNA targeting the TRAC gene is about 0.08 mg/ml. Alternatively, or in addition, the amount of the gRNA targeting the β2M gene may range from about 0.075 mg/ml to about 0.3 mg/ml, for example, about 0.1 mg/ml to about 0.3 mg/ml. In specific examples, the amount of the gRNA targeting the β2M gene is about 0.2 mg/ml.

In specific examples, the RNP complex targeting the TRAC gene may comprise about 0.15 mg/ml Cas9 (e.g., the Cas9 of SEQ ID NO:1) and about 0.08 mg/ml of a gRNA targeting the TRAC gene (e.g., the gRNA of TA-1). Alternatively or in addition, the RNP complex targeting the β2M gene may comprise about 0.15 mg/ml Cas9 (e.g., the Cas9 of SEQ ID NO:1) and about 0.2 mg/ml of a gRNA targeting the β2M gene (e.g., the gRNA of β2M-1).

The T cells after the second electroporation may be collected and cultured in a fresh medium for cell recovery. The cells can then be incubated with rAAV particles for delivery of the donor template carrying the CAR-encoding nucleotide sequences. See below disclosures.

(e) Exemplary Gene Editing for Edited Anti-CD70 CAR T Cells

The edited anti-CD70 CAR T cell product is a CD70-directed T cell immunotherapy comprised of allogeneic T cells that are genetically modified ex vivo using CRISPR/Cas9 (Clustered Regularly Interspaced Short Palindromic Repeats/CRISPR associated protein 9) gene editing components (sgRNA and Cas9 nuclease). The modifications include targeted disruption of TRAC, β2M, TFGBRII, Reg1, and CD70. Gene editing to introduce these genetic modifications may be performed by two sequential electroporation steps. In the first electroporation step, an RNP complex comprising a Cas9 enzyme (e.g., SEQ ID NO:1), a sgRNA targeting the Reg1 gene, a sgRNA targeting the TGFBRII gene, and a sgRNA targeting the β2M gene (see Table 3 below for exemplary sgRNAs) can be delivered to the activated T cells. In the second electroporation step, one or more RNP complexes comprising one or more Cas9 enzyme (e.g., SEQ ID NO:1) a sgRNA targeting the TRAC gene, and a sgRNA targeting the CD70 gene (see Table 3 below for exemplary sgRNAs) can be delivered to T cells recovered from the first electroporation step. This gene delivery approach allows for high gene editing efficiency and low translocation rates. FIG. 5 provide exemplary illustrations of this two-step electroporation approach. Examples of this approach are also provided below.

In some embodiments, a T cell population enriched with CD4+ T cells and CD8+ T cells may be activated following the disclosures provided herein to produce a population of activated T cells. The activated T cells are subject to a first electroporation to deliver an RNP comprising a Cas9 enzyme (e.g., SEQ ID NO:1), a sgRNA targeting the Reg1 gene, a sgRNA targeting the TGFBRII gene, and a sgRNA targeting the β2M gene (see Table 3 below for exemplary sgRNAs).

T cells used in the first electroporation may range from about $1\times10^8$ cells/ml to about $5\times10^8$ cells/ml; optionally about $3\times10^8$ cells/ml. For example, the amount of the activated T cells for the first electroporation step may range from about $2\times10^8$ cells/mL to about $3\times10^8$ cells/mL. In some examples, the amount of the activated T cells may be about $1\times10^8$ cells/mL. In some examples, the amount of the activated T cells may be about $2\times10^8$ cells/mL. In some examples, the amount of the activated T cells may be about $3\times10^8$ cells/mL.

In some instances, the Cas9 enzyme and the gRNA targeting Reg1, the gRNA targeting TGFBRII, and/or the gRNA targeting β2M may be at a suitable weight ratio, for example, about 4:1 to 1:4 (e.g., 4:1, 3:1, 2:1, 1:1, 1:2, 1:3, or 1:4). A suitable amount of each of the Cas9 enzyme(s) and the gRNAs may be used in the first electroporation step.

In the first electroporation step, the sgRNAs targeting Reg1, TGFBRII, and β2M may form three separate RNPs with a Cas9 enzyme (which may be identical in the three RNPs). Alternatively, the sgRNAs targeting Reg1, TGFBRII, and β2M may form two separate RNPs with a Cas9 enzyme (which may be identical in the three RNPs), one containing one sgRNA and the other containing the other two. The two or three RNP complexes may be mixed to form a mixture, which can be used for electroporation. In some instances, the two or three RNP complexes may contain the same amount of the Cas9 enzyme. In yet other instances, the sgRNAs targeting Reg1, TGFBRII, and β2M may form one RNP with a Cas9 enzyme.

In some examples, each of the sgRNAs form a separate RNP with the Cas9 enzyme. In some instances, the β2M sgRNA may have a concentration of about 0.1 to about 0.3 mg/mL (e.g., about 0.2 mg/mL) in the RNP. In some instances, the Reg1 sgRNA may have a concentration of about 0.01 to about 0.10 mg/mL, e.g., about 0.04 to about 0.08 mg/mL, in the RNP. In some instances, the TGFBRII sgRNA may have a concentration of about 0.01 to about 0.15 mg/mL, e.g., about 0.06 to about 0.12 mg/mL, in the RNP. One or more of the RNP complexes may comprise about 0.1-0.3 mg/ml (e.g., about 0.1-0.2 mg/ml) of the Cas9 enzyme (e.g., the Cas9 enzyme of SEQ ID NO:1). In some examples, each of the RNP complexes may comprise about 0.15 mg/ml of the Cas9 enzyme, which may be the Cas9 enzyme of SEQ ID NO:1. In other examples, each of the RNP complexes may comprise about 0.12 mg/ml of the Cas9 enzyme, which may be the Cas9 enzyme of SEQ ID NO:1. In other embodiments, the three RNP complexes may contain different amounts of the Cas9 enzyme. In some examples, the RNP complex targeting the Reg1 gene and/or the β2M gene may comprise a higher amount of the Cas9 enzyme relative to the RNP complex targeting the TGFBRII gene.

In some examples, the total amount of the Cas9 enzyme (e.g., SEQ ID NO:1) used in the first electroporation may range from about 0.3 mg/mL to about 0.6 mg/mL, for example, about 0.4 mg/mL to about 0.5 mg/mL. The amounts of the β2M sgRNA (e.g., β2M-1), the Reg1 sgRNA (R7), and the TGFBRII sgRNA (e.g., TGFBRII2-5) may be about 0.2 mg/mL, about 0.04-0.08 mg/mL, and about 0.06-0.12 mg/mL, respectively.

The T cells after the first electroporation can be collected and cultured in a medium for a suitable period for T cell recovery. In some instances, the T cells may be cultured for about 24-72 hours. In one example, the T cells may be cultured for 48 hours. In this recovery stage, the culture medium may be free of T cell activating agent, such as those disclosed herein (e.g., CD3 agonists and/or CD28 agonists).

The recovered T cells can then be subject to the second electroporation step for delivering RNPs comprising the Cas9 enzyme and the sgRNAs targeting TRAC and CD70. In some instances, the recovered T cells used in the second electroporation may range from about $1\times10^8$ cells/ml to about $5\times10^8$ cells/ml; optionally about $3\times10^8$ cells/ml. For example, the amount of the activated T cells for the first electroporation step may range from about $2\times10^8$ cells/mL to about $3\times10^8$ cells/mL. In some examples, the amount of the activated T cells may be about $1\times10^8$ cells/mL. In some examples, the amount of the activated T cells may be about $2\times10^8$ cells/mL. In some examples, the amount of the activated T cells may be about $3\times10^8$ cells/mL.

In the second electroporation step, the sgRNAs targeting TRAC and CD70/32M may form a single RNP with the Cas9 enzyme. Alternatively, they may form two separate RNPs, which may be mixed to form a mixture for use in the electroporation. A suitable amount of each of the Cas9 enzyme and the sgRNAs may be used in the second electroporation.

In the second electroporation step, the sgRNAs targeting TRAC and CD70 may form two separate RNPs with a Cas9 enzyme (which may be identical in the two RNPs). Two RNP complexes may be mixed to form a mixture, which can be used for electroporation. In some instances, the two RNP complexes may contain the same amount of the Cas9 enzyme. For example, both RNP complexes may comprise about 0.1-0.3 mg/ml (e.g., about 0.1-0.2 mg/ml) of the Cas9 enzyme (e.g., the Cas9 enzyme of SEQ ID NO:1). In some examples, each of the RNP complexes may comprise about 0.15 mg/ml of the Cas9 enzyme, which may be the Cas9 enzyme of SEQ ID NO:1. In other embodiments, the two RNP complexes may contain different amounts of the Cas9 enzyme. In some examples, the RNP complex targeting the TRAC gene may comprise a higher amount of the Cas9 enzyme relative to the RNP complex targeting the CD70 gene. Alternatively, the RNP complex targeting the CD70 gene may comprise a higher amount of the Cas9 enzyme relative to the RNP complex targeting the TRAC gene.

Alternatively or in addition, the two RNP complexes may comprise the same amount of the gRNAs (one targeting TRAC and the other targeting CD70). Alternatively, the two RNP complexes may comprise different amounts of the gRNAs. For example, the amount of the gRNA targeting the TRAC gene may range from about 0.05 mg/ml to about 0.25 mg/ml, for example, about 0.1 to about 0.15 mg/mL. In specific examples, the amount of the gRNA targeting the TRAC gene is about 0.12 mg/ml. Alternatively, or in addition, the amount of the gRNA targeting the CD70 gene may range from about 0.05 mg/ml to about 0.3 mg/ml, for example, about 0.1 mg/ml to about 0.2 mg/ml. In specific examples, the amount of the gRNA targeting the CD70 gene is about 0.15 mg/ml or about 0.16 mg/ml.

In specific examples, the RNP complex targeting the TRAC gene may comprise about 0.15 mg/ml Cas9 (e.g., the Cas9 of SEQ ID NO:1) and about 0.12 mg/ml of a gRNA targeting the TRAC gene (e.g., the gRNA of TA-1). Alternatively or in addition, the RNP complex targeting the β2M gene may comprise about 0.15 mg/ml Cas9 (e.g., the Cas9 of SEQ ID NO:1) and about 0.16 mg/ml of a gRNA targeting the CD70 gene (e.g., the gRNA of CD70-7).

The T cells after the second electroporation may be collected and cultured in a fresh medium for cell recovery. The cells can then be incubated with rAAV particles for delivery of the donor template carrying the CAR-encoding nucleotide sequences. See below disclosures.

E. T Cell Transduction

After delivery of the gene editing system(s) disclosed herein, the resultant T cells may be subject to transduction with a viral vector such as an adeno-associated viral (AAV) vector that comprises a nucleic acid sequence encoding a chimeric antigen receptor (CAR) to produce a population of T cells expressing the CAR. In some instances, the viral vector also comprise homology arms flanking the CAR-coding nucleotide sequence. The homology arms target a specific gene locus, allowing for inserting the CAR-coding nucleotide sequence into the target gene locus via homologous recombination. The target gene locus may be one of the target genes for editing as disclosed herein, e.g., Reg1, TGFBRII, TRAC, β2M, or CD70. In a specific example, the target gene locus is a site within the TRAC gene, for example, the site targeted by a gRNA (e.g., TA-1) for editing the TRAC gene. To improve homologous recombination rates and thus CAR-insertion rates, the transduction step is preferred to be performed shortly after delivery of the gene editing system targeting the gene site where the CAR-coding sequence is to be inserted.

Chimeric Antigen Receptor (CAR)

A chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR-T cells the ability to recognize an antigen independent of antigen processing, thus bypassing a major mechanism of tumor escape. Moreover, when expressed on T-cells, CARs advantageously do not dimerize with endogenous T-cell receptor (TCR) alpha and beta chains.

There are various generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional co-stimulatory domain, e.g., CD28, 4-1BB (41BB), or ICOS, to supply a costimulatory signal. Third-generation CARs contain two costimulatory domains (e.g., a combination of CD27, CD28, 4-1BB, ICOS, or OX40) fused with the TCR CD3ζ chain. Maude et al., Blood. 2015; 125(26):4017-4023; Kakarla and Gottschalk, Cancer J. 2014; 20(2):151-155). Any of the various generations of CAR constructs is within the scope of the present disclosure.

Generally, a CAR is a fusion polypeptide comprising an extracellular domain that recognizes a target antigen (e.g., a single-chain variable fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8): 498-505). A CAR construct may further comprise a hinge and transmembrane domain between the extracellular domain and the intracellular domain, as well as a signal peptide at the N-terminus for surface expression. Examples of signal peptides include MLLLVTSLLLCELPHPAFLLIP (SEQ ID NO: 80) and MALPVTALLLPLALLLHAARP (SEQ ID NO: 93). Other signal peptides may be used.

(a) Antigen Binding Extracellular Domain

The antigen-binding extracellular domain is the region of a CAR polypeptide that is exposed to the extracellular fluid when the CAR is expressed on cell surface. In some instances, a signal peptide may be located at the N-terminus to facilitate cell surface expression. In some embodiments, the antigen binding domain can be a single-chain variable fragment (scFv, which may include an antibody heavy chain variable region ($V_H$) and an antibody light chain variable region ($V_L$) (in either orientation). In some instances, the $V_H$ and $V_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized $V_H$ and/or $V_L$ domains. In other embodiments, the $V_H$ and/or $V_L$ domains of the scFv are fully human.

The antigen-binding extracellular domain may be specific to a target antigen of interest, for example, a pathologic antigen such as a tumor antigen. In some embodiments, a tumor antigen is a "tumor associated antigen," referring to an immunogenic molecule, such as a protein, that is generally expressed at a higher level in tumor cells than in non-tumor cells, in which it may not be expressed at all, or only at low levels. In some embodiments, tumor-associated structures, which are recognized by the immune system of the tumor-harboring host, are referred to as tumor-associated antigens. In some embodiments, a tumor-associated antigen is a universal tumor antigen, if it is broadly expressed by most types of tumors. In some embodiments, tumor-associated antigens are differentiation antigens, mutational antigens, overexpressed cellular antigens or viral antigens. In some embodiments, a tumor antigen is a "tumor specific antigen" or "TSA," referring to an immunogenic molecule, such as a protein, that is unique to a tumor cell. Tumor specific antigens are exclusively expressed in tumor cells, for example, in a specific type of tumor cells.

In some examples, the CAR constructs disclosed herein comprise a scFv extracellular domain capable of binding to CD70. In some examples, the CAR constructs disclosed herein comprise a scFv extracellular domain capable of binding to CD19. In some examples, the CAR constructs disclosed herein comprise a scFv extracellular domain capable of binding to BCMA. An example of an anti-CD70 CAR is provided in Examples below.

(b) Transmembrane Domain

The CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. Exemplary transmembrane domains of CD8a are provided in Table 8 below. Other transmembrane domains may be used.

(c) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(d) Intracellular Signaling Domains

Any of the CAR constructs contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3 contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling.

In some embodiments, the CAR polypeptides disclosed herein may further comprise one or more co-stimulatory signaling domains. For example, the co-stimulatory domains of CD28 and/or 4-1BB may be used to transmit a full proliferative/survival signal, together with the primary signaling mediated by CD3. In some examples, the CAR disclosed herein comprises a CD28 co-stimulatory molecule. In other examples, the CAR disclosed herein comprises a 4-1BB co-stimulatory molecule. In some embodiments, a CAR includes a CD3ζ signaling domain and a CD28 co-stimulatory domain. In other embodiments, a CAR includes a CD3ζ signaling domain and 4-1BB co-stimulatory domain. In still other embodiments, a CAR includes a CD3ζ signaling domain, a CD28 co-stimulatory domain, and a 4-1BB co-stimulatory domain.

It should be understood that methods described herein encompasses more than one suitable CAR that can be used to produce genetically engineered T cells expressing the CAR, for example, those known in the art or disclosed herein. Examples can be found in, e.g., WO 2019/097305A2, the relevant disclosures of each of the prior applications are herein incorporated by reference for the purposes and subject matter referenced herein.

In some embodiments, the CAR disclosed herein binds CD19 (also known as a "CD19 CAR" or an "anti-CD19 CAR"). The amino acid sequence of an exemplary CAR that binds CD19 is provided in Table 8 below. In some instances, the anti-CD19 CAR is a mature form, which does not include the N-terminal signal peptide.

In some embodiments, the CAR disclosed herein binds CD70 (also known as a "CD70 CAR" or an "anti-CD70 CAR"). The amino acid sequence of an exemplary CAR that binds CD70 is provided in Table 8 below. In some instances, the anti-CD70 CAR is a mature form, which does not include the N-terminal signal peptide.

AAV Vectors for Delivery of CAR Constructs to T Cells

A nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding a CAR can be designed to insert into a genomic site of interest in the host T cells. In some embodiments, the target genomic site can be in a safe harbor locus.

In some embodiments, a nucleic acid encoding a CAR (e.g., via a donor template, which can be carried by a viral vector such as an adeno-associated viral (AAV) vector) can be designed such that it can insert into a location within a target gene, such as a TRAC gene, to disrupt the target gene, such as the TRAC gene, in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions can be used for this purpose, e.g., those disclosed herein.

In some examples, a genomic deletion in the TRAC gene and replacement by a CAR coding segment can be created by homology directed repair or HDR (e.g., using a donor template, which may be part of a viral vector such as an adeno-associated viral (AAV) vector). In some examples, the gRNA target sequence, or portion thereof, is deleted (e.g., SEQ ID NO: 27). In some embodiments, a disruption in the TRAC gene can be created with an endonuclease as those disclosed herein and one or more gRNAs targeting one or more TRAC genomic regions and inserting a CAR coding segment into the TRAC gene.

A donor template as disclosed herein can contain a coding sequence for a CAR. In some examples, the CAR-coding sequence may be flanked by two regions of homology to allow for efficient HDR at a genomic location of interest, for example, at a TRAC gene using CRISPR-Cas9 gene editing technology. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

A donor template, in some embodiments, can be inserted at a site nearby an endogenous promoter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1α promoter. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

T Cell Transduction

A suitable amount of any of the viral particles such as an AAV particles, which encodes a CAR construct disclosed herein (e.g., an anti-CD19 CAR or an anti-CD70 CAR) may be incubated with a suitable amount of T cells, such as the genetically edited T cells disclosed herein for a suitable period to allow for entry of the viral vector into the T cells. For example, the transduction process may involve the use of a range of optimized multiplicity of infection (MOI) that increases percentages of CARP T cells. In some instances, the MOI of an AAV vector in the transduction process may range from about 1,000 to about 150,000, such as from about 10,000 to about 80,000. In some examples, the MOI of the AAV vector used in the transduction process may be about 1,000 to about 150,000, about 5,000 to about 100,000, about 10,000 to about 100,000, about 10,000 to about 90,000, about 10,000 to about 80,000, about 10,000 to about 70,000, about 10,000 to about 60,000, about 10,000 to about 50,000, about 10,000 to about 40,000, about 10,000 to about 30,000, about 10,000 to about 20,000, about 20,000 to about 80,000, about 30,000 to about 80,000, about 40,000 to about 80,000, about 50,000 to about 80,000, about 60,000 to about 80,000, or about 70,000 to about 80,000. In some examples, the MOI of the AAV vector used in the transduction process may be about 1,000, about 2,500, about 5,000, about 10,000, about 15,000, about 20,000, about 25,000, about 30,000, about 31,000, about 32,000, about 33,000, about 34000, about 35,000, about 40,000, about 50,000, about 60,000, about 70,000, about 80,000, about 90,000, about 100,000, about 110,000, about 120,000, about 130,000, about 140,000, or about 150,000.

In some embodiments, the AAV vector encodes an anti-CD19 CAR (e.g., as disclosed in Table 8 in Example 5 below) and the MOI of such an AAV vector for use in the transduction process is about 20,000. In other embodiments, the AAV vector encodes an anti-CD19 CAR and the MOI of such an AAV vector for use in the transduction process is about 20,000.

After transduction, the T cells may be cultured in a suitable cell culture medium for a suitable period for recovery. The genetically engineered T cells, having disrupted Reg1, TGFBRII, TRAC, β2M, and optionally CD70, genes and expressing the CAR, may be expanded in vitro as disclosed below.

F. T Cell Expansion

The genetically engineered T cells as disclosed herein may be expanded in vitro under suitable conditions to produce a population of genetically engineered T cells to a clinically relevant scale. Cell culture conditions used in this expansion step intend to, at least in part, achieve higher final cell densities in shorter incubation periods (thereby reducing manufacturing cost) and higher potent T cells for use in cell therapy. Potency may be indicated by various T cell functions, e.g., proliferation, target cell killing, cytokine production, activation, migration, and combinations thereof.

In some embodiments, the T cell expansion step may be performed by seeding a population of T cells (e.g., the genetically engineered T cells as disclosed herein) in a cell culture vessel at a seeding density of about 150,000 cells/$cm^2$ to about 600,000 cells/$cm^2$ in a cell vessel. For example, the T cells may be seeded at about 300,000 cells/$cm^2$ to about 500,000 cells/$cm^2$, in a cell vessel. In some aspects, the T cell expansion is performed by seeding a population of T cells in a cell culture vessel at a seeding density of at least about 60,000 cells/$cm^2$, at least about 62,500 cells/$cm^2$, or at least about 83,000 cells/$cm^2$. In some aspects, the T cell expansion is performed by seeding a population of T cells in a cell culture vessel at a seeding density of at least about 150,000 cells/$cm^2$, or at least about 250,000 cells/$cm^2$, or at least about 300,000 cells/$cm^2$, or at least about 400,000 cells/$cm^2$, or at least about 500,000 cells/$cm^2$, or at least about 600,000 cells/$cm^2$. In some aspects, the seeding density is about 250,000 cells/$cm^2$. In other aspects, the seeding density is about 500,000 cells/$cm^2$. In other aspects, the seeding density is about 600,000 cells/$cm^2$.

In some embodiments, the T cell expansion step may be performed by seeding a population of T cells (e.g., the genetically engineered T cells as disclosed herein) in a cell culture vessel at a seeding density of about $2\times10^5$ cells/$cm^2$ to about $7\times10^5$ cells/$cm^2$, and culturing the cells for about 6 days to about 12 days. In some examples, the T cell expansion is performed by seeding a population of T cells in a cell culture vessel at a seeding density of about $2\times10^5$ cells/$cm^2$ to about $7\times10^5$ cells/$cm^2$, about $2\times10^5$ cells/$cm^2$ to about $5\times10^5$ cells/$cm^2$, about $2\times10^5$ cells/$cm^2$ to about $4\times10^5$ cells/$cm^2$, $2\times10^5$ cells/$cm^2$ to about $3\times10^5$ cells/$cm^2$, $3\times10^5$ cells/$cm^2$ to about $5\times10^5$ cells/$cm^2$, or $4\times10^5$ cells/$cm^2$ to about $5\times10^5$ cells/$cm^2$, and culturing the cells for about 6 days to about 12 days, about 6 days to about 11 days, about 6 days to about 10 days, about 6 days to about 9 days, about 6 days to about 8 days, about 6 days to about 7 days, about 7 days to about 12 days, about 7 days to about 11 days, about 7 days to about 10 days, about 7 days to about 9 days, about 7 days to about 8 days, about 8 days to about 12 days, about 8 days to about 9 days, about 9 days to about 12 days, about 10 days to about 12 days, or about 11 days to about 12 days. In some embodiments, the T cell expansion is performed by seeding a population of T cells in a cell culture vessel at a seeding density of about $3\times10^5$ cells/$cm^2$ to about $5\times10^5$ cells/$cm^2$ and culturing the cells for about 7 days to about 9 days.

In some embodiments, the T cell expansion step may include replating the cell culture (i.e., splitting the cell culture into new culture vessels). In some embodiments, the cell culture can be replated at day 3, 4, 5, 6, or 7 post editing at a 1:4 ratio (1 vessel split into 4 new vessels) for further expansion.

T cell expansion may be performed in a static culture vessel, which allows expansion of the T cells without medium change. For example, T cells can be expanded in a static culture vessel for at about 7 days to about 12 days, or at about 7 days to about 9 days without medium change.

G. Depletion of $TCR\alpha\beta^+$ T Cells

In some embodiments, $TCR\alpha\beta^+$ T cells may be depleted from the expanded T cell population disclosed herein to produce a population of allogenic T cells for use in cell therapy. As used herein, "$TCR\alpha\beta^+$ T cell depletion" refers to depleting $TCR\alpha\beta^+$ T cells from a population of cells comprising such. Following $TCR\alpha\beta^+$ T cell depletion, the resultant T cell population may have a substantially low level of $TCR\alpha\beta^+$ T cell (e.g., less than 3% in the total cell population, or less than 2%, less than 1%, or less than 0.5% in the total cell population). In some examples, the resultant T cell population may be free of $TCR\alpha\beta^+$ T cell, i.e., presence of $TCR\alpha\beta^+$ T cell is not dateable via a conventional method (e.g., in an immune assay using an antibody binding to $TCR\alpha\beta^+$ or by flow cytometry).

$TCR\alpha\beta^+$ T cell depletion may be performed using an agent that recognizes $TCR\alpha\beta^+$ T cells to capture the $TCR\alpha\beta^+$ T cells, thereby separating them from those lacking $TCR\alpha\beta^+$, e.g., by performing a magnetic cell separation. Such methods may be carried out by contacting the expanded T cells disclosed above to beads on which anti-$TCR\alpha\beta$ antibodies are immobilized, and collecting unbound cells. Unbound cells (those lacking $TCR\alpha\beta^+$) thus collected may be cultured to allow cell recovery prior, for example, unbound cells may be cultured overnight to allow cells to recover.

H. Harvest of Genetically Engineered T Cells

The genetically engineered T cells produced by any of the methods disclosed herein can then be harvested for therapeutic uses using conventional methods known in the art. For example, harvesting genetically engineered T cells may comprise collecting cells from which $TCR\alpha\beta^+$ has been depleted. The harvested population of genetically engineered T cells may be used as the drug substance. As used herein, a "drug substance" refers to a population of genetically engineered T cells that may be administered to patients. The drug substance may be formulated for therapeutic uses, e.g., formulated in storage media (e.g., CryoStor® CS5) and cryopreserved for future use.

The drug substance may be tested for one or more contaminants, e.g., mycoplasma, human viruses (e.g., HIV, HBV, HCV, CMV), and bacterial endotoxins. Alternatively, or in addition to, the drug substance may be tested for sterility. Contamination free drug substance may be aliquoted into individual patient doses. Alternatively, or in addition to, contamination free drug substance may be stored for therapeutic use.

II. Genetically Engineered T Cells and Therapeutic Applications Thereof

A population of genetically engineered T cells produced by any of the methods described herein is also within the scope of the present disclosure. Such genetically engineered T cells may be used for therapeutic purposes.

In some embodiments, a population of genetically engineered T cells disclosed herein express a CAR (e.g., anti-CD19, anti-BCMA, or anti-CD70 CAR), a disrupted Reg1 gene, a disrupted TGFBRII gene, a disrupted TRAC gene, and optionally a disrupted β2M gene, and optionally a disrupted CD70 gene. The nucleotide sequence encoding the CAR may be inserted in the disrupted TRAC gene (e.g., replacing the site targeted by a sgRNA such as TA-1). In some examples, such a population of genetically engineered T cells may comprise about 70-99% $Reg1^-$ cells, for example about 90-97% $Reg1^-$ cells, about 70-99% $TGFBRII^-$ cells, e.g., for example about 80-89% $TGFBRII^-$ cells, about 70-99% $TCR^-$ cells, for example about 90-99% $TCR^-$ cells, and/or optionally about 60-99% $\beta 2M^-$ cells, for example about 60-82% $\beta 2M^-$ cells, and/or optionally about 70-99% $CD70^-$ cells, for example about 90-99% $CD70^-$ cells. The cell population may also contain at least about 30%-50% (e.g., at least 60%) cells expressing the CAR.

In some embodiments, a population of genetically engineered T cells disclosed herein express an anti-CD19 CAR (e.g., the exemplary anti-CD19 CAR provided in Table 8 below), a disrupted Reg1 gene, a disrupted TGFBRII gene, a disrupted TRAC gene, and a disrupted β2M gene. The nucleotide sequence encoding the anti-CD19 CAR may be inserted in the disrupted TRAC gene (e.g., replacing the site targeted by a sgRNA such as TA-1). In some examples, such a population of genetically engineered T cells may comprise about 90-97% $Reg1^-$ cells, about 80-89% $TGFBRII^-$ cells, about 90-99% $TCR^-$ cells, and/or about 60-82% $\beta 2M^-$ cells. The cell population may also contain at least 50% (e.g., at least 60%) cells expressing the anti-CD19 CAR.

In other embodiments, a population of genetically engineered T cells disclosed herein express an anti-CD70 CAR (e.g., the exemplary anti-CD70 CAR provided in Table 8 below), a disrupted Reg1 gene, a disrupted TGFBRII gene, a disrupted TRAC gene, a disrupted β2M gene, and a disrupted CD70 gene. The nucleotide sequence encoding the anti-CD70 CAR may be inserted in the disrupted TRAC gene (e.g., replacing the site targeted by a sgRNA such as TA-1).

Any of the genetically engineered T cells disclosed herein may be administered to a subject for therapeutic purposes, for example, treatment of a cancer targeted by the CAR construct expressed by the population of genetically engineered T cells. In some instances, the target cancer comprises CD19+ cancer cells. In other instances, the target cancer comprises CD70+ cancers. In some instances, the cancer is a hematopoietic cancer. In other instances, the cancer is a solid tumor.

A subject may be any subject for whom diagnosis, treatment, or therapy is desired. In some embodiments, the subject is a mammal. In some embodiments, the subject is a human.

Non-limiting examples of cancers that may be treated using a genetically engineered T cell population produced by methods described herein include, but are not limited to, multiple myeloma, leukemia (e.g., T cell leukemia, B-cell acute lymphoblastic leukemia (B-ALL), and/or chronic lymphocytic leukemia (C-CLL)), lymphoma (e.g., B-cell non-Hodgkin's lymphoma (B-NHL), Hodgkin's lymphoma, and/or T cell lymphoma), and/or clear cell renal cell carcinoma (ccRCC), pancreatic cancer, gastric cancer, ovarian cancer, cervical cancer, breast cancer, renal cancer, thyroid cancer, nasopharyngeal cancer, non-small cell lung (NSCLC), glioblastoma, and/or melanoma.

Administering may include placement (e.g., transplantation) of the genetically engineered T cell population into a subject by a method or route that results in at least partial localization of the genetically engineered T cell population at a desired site, such as a tumor site, such that a desired effect(s) can be produced. The genetically engineered T cell population can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the lifetime of the subject, i.e., long-term engraftment. For example, in some aspects described herein, an effective amount of the genetically engineered T cell population can be administered via a systemic route of administration, such as an intraperitoneal or intravenous route.

In some embodiments, the genetically engineered T cell population is administered systemically, which refers to the administration of a population of cells other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

An effective amount refers to the amount of a genetically engineered T cell population needed to prevent or alleviate at least one or more signs or symptoms of a medical condition (e.g., cancer), and relates to a sufficient amount of a genetically engineered T cell population to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

An effective amount of a genetically engineered T cell population may comprise at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof.

The efficacy of a treatment using the genetically engineered T cell population manufactured as described herein can be determined by a person of ordinary skill in the art. A treatment is considered "effective", if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Genetically engineered T cell populations manufactured as described herein may also be used in combination therapies. For example, the genetically engineered T cell population manufactured as described herein may be co-used with other therapeutic agents, for treating the same indication, or for enhancing efficacy of the genetically engineered T cell population and/or reducing side effects of the genetically engineered T cell population.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985*; Transcription and Translation* (B. D. Hames & S. J. Higgins, eds. (1984*; Animal Cell Culture* (R. I. Freshney, ed. (1986*; Immobilized Cells and Enzymes* (IRL Press, (1986; and B. Perbal, *A practical Guide To Molecular Cloning* (1984); F. M. Ausubel et al. (eds.).

EXAMPLES

In order that the invention described may be more fully understood, the following examples are set forth. The examples described in this application are offered to illustrate the methods and compositions provided herein and are not to be construed in any way as limiting their scope.

Example 1: Identification of Optimized Timing for T Cell Activation

This Example reports identification of optimized activation period for gene editing using a CRISPR/Cas9 gene editing system. Gene editing levels were examined on T cells activated for different periods of time to identify the optimized period for T cell activation that achieve superior gene editing levels. In brief, genetically engineered T cells were manufacturing in a small-scale process in which enriched T cells were thawed and subsequently activated for 0, 1, 2, 3, or 4 days before electroporation event. For T cell activation, the colloidal polymeric nanomatrix conjugated to recombinant humanized CD3 and CD28 agonists was applied to cells at a 1:12.5 ratio or 40 μL per $1\times10^6$ cells in static culture vessels. T cells were electroporated with TRAC RNP (80 μg/mL TRAC sgRNA and 150 μg/mL Cas9), β2M RNP (200 μg/mL β2M sgRNA and 150 μg/mL Cas9), Regnase-1 RNP (160 μg/mL Regnase sgRNA and 150 μg/mL Cas9) and TGFBRII RNP (160 μg/mL TGFBRII sgRNA and 150 μg/mL Cas9), separately, with an electroporator. A separate amount of T cells was also electroporated with CD70 RNP [80 μg/mL CD70 sgRNA and 150 μg/mL Cas9] with an electroporator. Cell concentration for electroporation is $300\times10^6$/mL. Sequences for the sgRNAs are provided in Table 3 herein. Four days post electroporation, cells were subjected to TIDE analysis to determine editing efficiency (FIGS. 1A-1E). As shown in FIGS. 1A-1E, editing efficiency for TRAC (FIG. 1A), β2M (FIG. 1B), Regnase-1 (FIG. 1C), TGFBRII (FIG. 1D), and CD70 (FIG. 1E) on inactivated T cells (A0) were significantly lower than those on activated T cells. 24, 48, 72 and 96 hours after activation provided equivalent high editing efficiency for all targets except Regnase-1. Decreased editing of Regnase-1 on T cells with 96 hour activation was 65.1% compared with 91% at 24 hrs, 92.8% at 48 hrs and 92.2% at 72 hours. Considering the minimal activation required for satisfying editing efficiency, total 48-hour activation was chosen for the edited anti-CD19 CAR T cell product process and the edited anti-CD70 CAR T cell product process.

Example 2: Identification of Optimized Conditions for Knockout of Regnase-1

This Example reports identification of optimized Regnase-1 guide amount and Cas9 amount for knockout of Regnase-1 using CRISPR-Cas9 dependent gene editing.

Figures 1A, 1B:
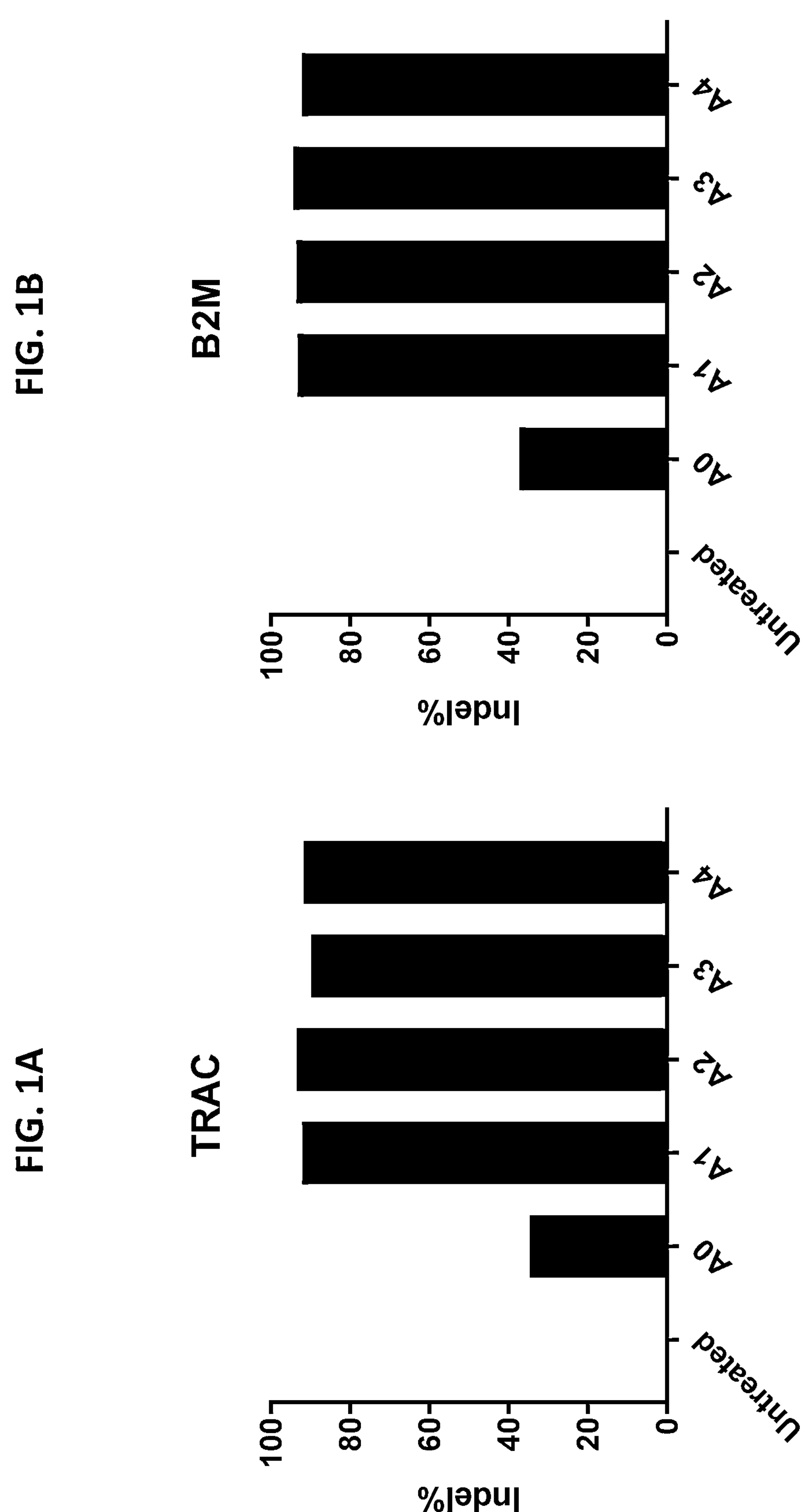
Figures 1C, 1D:
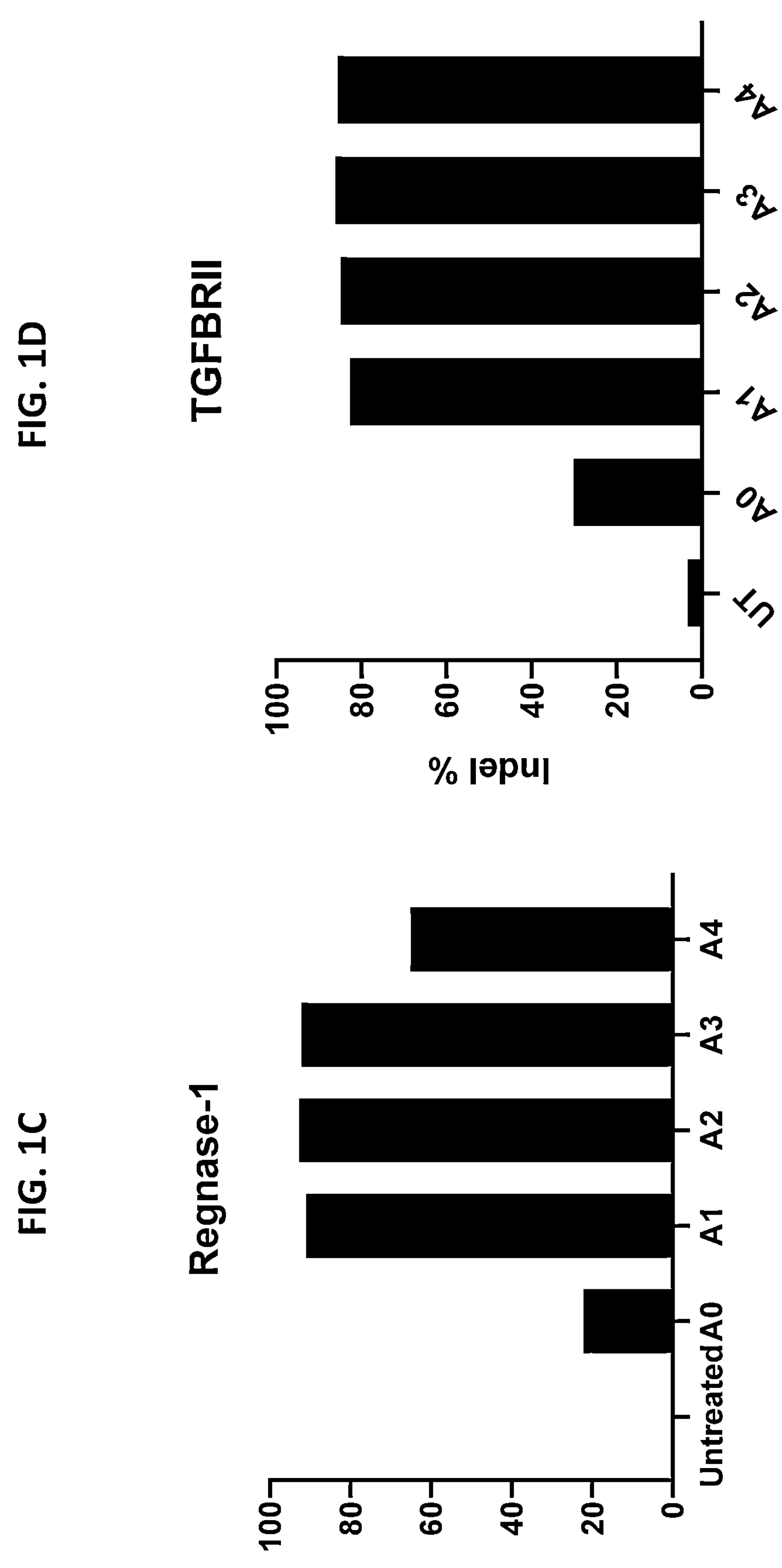
Figure 1E:
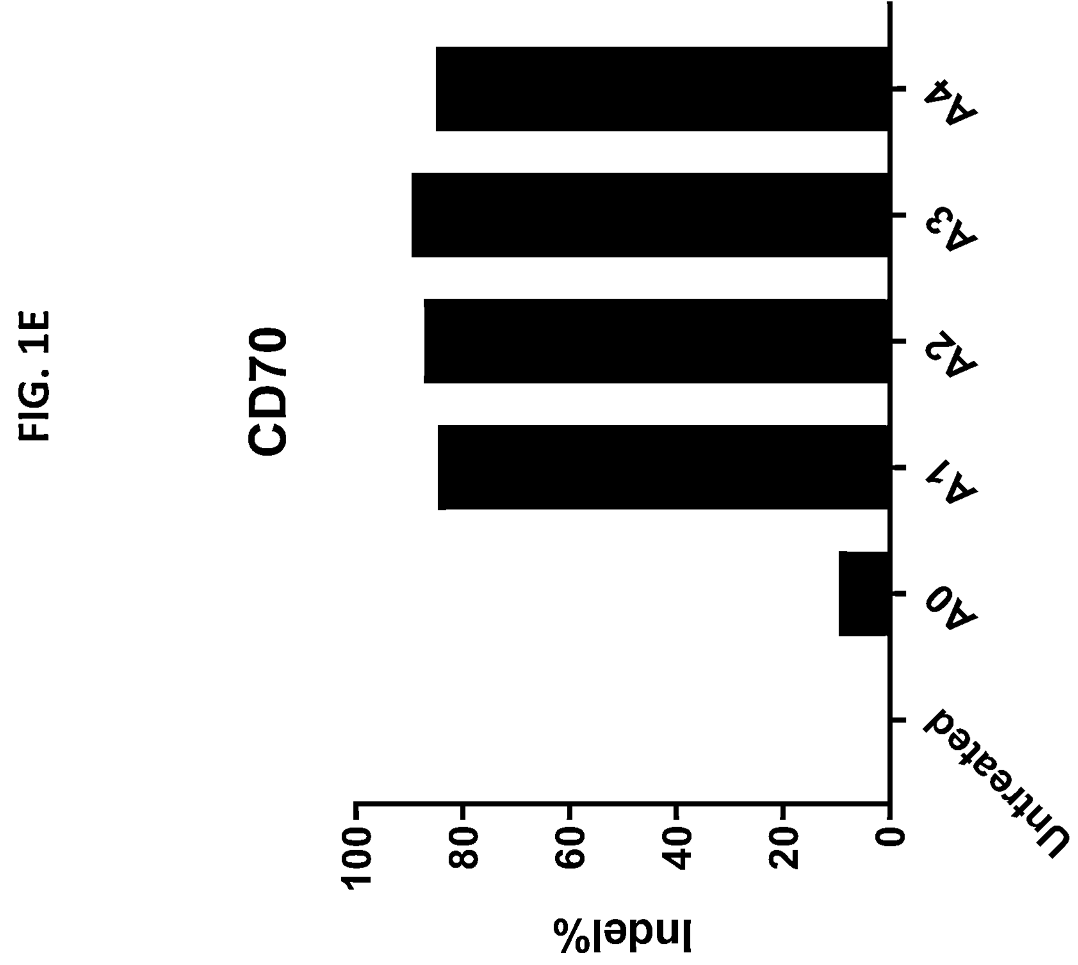
Figure 2:
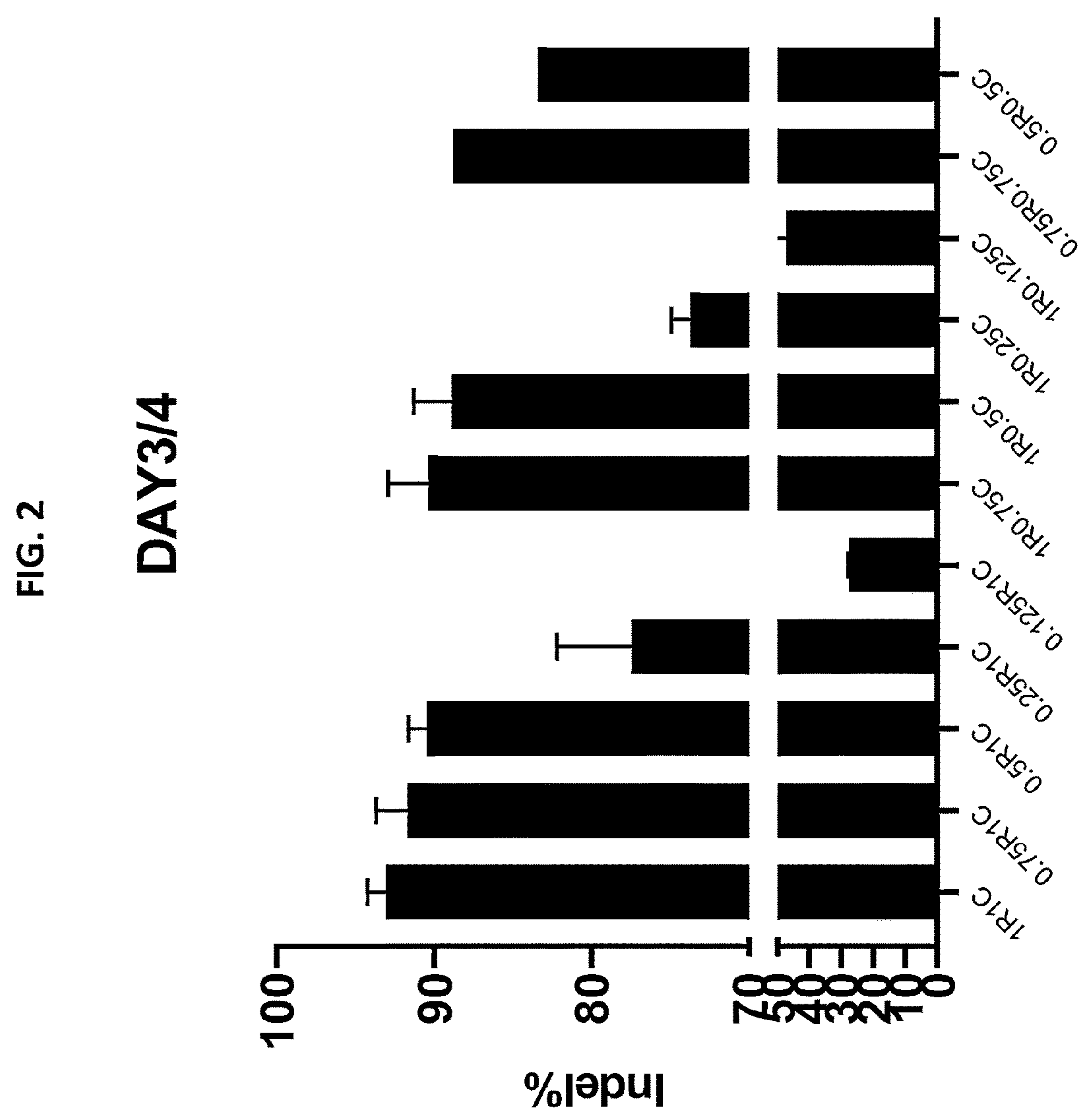
FIG. 2 is a chart showing editing efficiencies of Reg1 at various Reg1 sgRNA and Cas9 RNP doses. 1R: Reg1 sgRNA at 160 μg/ml. 1C: Cas9 at 150 μg/ml.

In brief, genetically engineered T cells were manufactured in a small-scale process, in which RNP complexes targeting Regnase-1 were added after 48 hrs activation. Table 1 shows the amounts of Regnase-1 guide tested, where Regnase sgRNA 1× was 160 μg/mL, Cas9 1× was 150 μg/mL. The sequence of the Regnase sgRNA is provided in Table 3 below. With the goal to maintain greater than 90% Regnase-1 editing (as determined by TIDE; FIG. 2) the optimal dose for Regnase knockout was Regnase-1 of 120 μg/mL and Cas9 of 150 μg/mL.

TABLE 1

| Gene Editing Conditions for Regnase-1 and Editing Efficiency | | | | | |
|---|---|---|---|---|---|
| EP Groups | Regl sgRNA | CAS9 | Indel %-1 | Indel %-2 | Average |
| 1 | 1X | 1X | 93.9 | 92.3 | 93.1 |
| 2 | 0.75X | 1X | 93.1 | 90.3 | 91.7 |
| 3 | 0.5X | 1X | 91.3 | 89.7 | 90.5 |
| 4 | 0.25X | 1X | 80.8 | 74.1 | 77.45 |
| 5 | 0.125x | 1X | 27.7 | 27.1 | 27.4 |
| 6 | 1X | 0.75X | 92.2 | 88.6 | 90.4 |
| 7 | 1X | 0.5X | 90.6 | 87.2 | 88.9 |
| 8 | 1X | 0.25X | 74.6 | 72.9 | 73.75 |
| 9 | 1X | 0.125x | 52.9 | 41.6 | 47.25 |
| 10 | 0.75X | 0.75X | NA | 88.8 | 88.8 |
| 11 | 0.5x | 0.5x | NA | 83.4 | 83.4 |

Example 3: Identification of Optimized Conditions for Knockout of TGFBRII

This Example reports identification of optimized TGFBRII guide amount and Cas9 amount for knockout of TGFBRII using CRISPR-Cas9 dependent gene editing.

Figure 3:
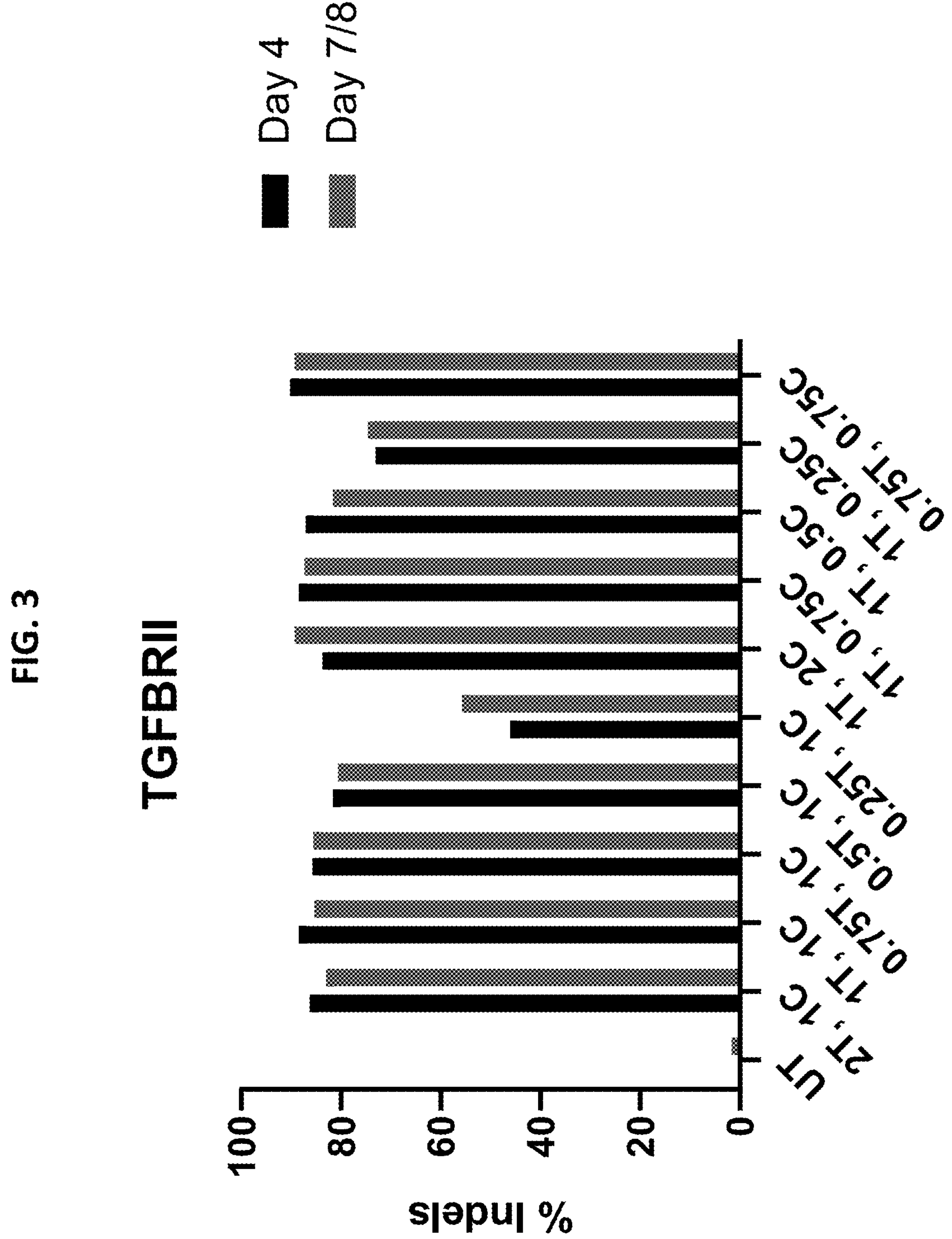
FIG. 3 is a chart showing editing efficiencies of TGFBRII at various TGFBRII sgRNA and Cas9 RNP doses. 1R: TGFBRII sgRNA at 160 μg/ml. 1C: Cas9 at 150 μg/ml.

In brief, genetically engineered T cells were manufactured in a small-scale process, in which RNP complexes targeting TGFBRII were added to the T cells after 48 hrs activation. Table 2 shows the amounts of TGFBRII guide tested, where TGFBRII sgRNA 1× was 160 μg/mL, Cas9 1× was 150 μg/mL. The sequence of the TGFBRII sgRNA is provided in Table 3. With the goal to maintain greater than 80% TGFBRII editing (as determined by TIDE; FIG. 3), the optimal dose for TGFBRII knockout was TGFBRII sgRNA of 120 μg/mL and Cas9 of 120 μg/mL.

number of translocation species generated from single electroporation event, four knockout targets are splinted into 2 electroporation events with two knockout targets in each electroporation. The predicted translocation rates from three target pair options are listed in Table 10. The prediction is based on historical translocation data generated from different experiments.

TABLE 10

| Predicted translocation rate | | | |
|---|---|---|---|
| Option | 1st Electroporation | 2nd Electroporation | Predicted translocation rate |
| 1 | Regnase, TGFBRII | TRAC, B2M | 2 |
| 2 | B2M, TGFBRII | TRAC, Regnase | 1.6 |
| 3 | B2M, Regnase | TRAC, TGFBRII | 2 |

A small scale process with the proposed target pairing as described in Table 10 was performed in T cells from three different donors. Translocation rates were assessed with Anchor seq on the edited anti-CD19 CAR T cell product harvested after 7 days expansion. Translocation rates are listed in Table 11. The translocation rates from three target pairing options were between 1.1% to 2.5%, which were below 3.0%. Due to past experience with the TRAC and B2M pair with a different edited anti-CD19 CAR T cell product and comparable translocation rates detected from the three paring options, Option 1, Regnase and TGFBRII knockout performed in first electroporation and TRAC and B2M knockout performed in second electroporation, was selected for edited anti-CD19 CAR T cell product manufacture process.

TABLE 2

| Gene Editing Conditions for TGFBRII and Editing Efficiency | | | | | | | | |
|---|---|---|---|---|---|---|---|---|
| EP Groups | TGFBRII | CAS9 | Indel %-1 | Indel %-2 Day 4 | Average | Indel %-1 | Indel %-2 Day 7/8 | Average |
| 1 | 1X | 1X | 87.1 | 90.0 | 88.6 | 82.7 | 88.1 | 85.4 |
| 2 | 2X | 1X | 86.4 | NA | 86.4 | 83.0 | NA | 83.0 |
| 3 | 0.75X | 1X | 83.7 | 87.8 | 85.8 | 81.7 | 89.5 | 85.6 |
| 4 | 0.5X | 1X | 81.7 | NA | 81.7 | 80.6 | NA | 80.6 |
| 5 | 0.25X | 1x | 46.1 | NA | 46.1 | 55.8 | NA | 55.8 |
| 6 | 1X | 2X | 83.8 | NA | 83.8 | 89.4 | NA | 89.4 |
| 7 | 1X | 0.75X | 86.3 | 90.7 | 88.5 | 84.4 | 90.3 | 87.4 |
| 8 | 1X | 0.5X | 87.1 | NA | 87.1 | 81.7 | NA | 81.7 |
| 9 | 1x | 0.25x | 73.1 | NA | 73.1 | 74.7 | NA | 74.7 |
| 10 | 0.75X | 0.75X | NA | 90.3 | 90.3 | NA | 89.4 | 89.4 |

Example 4: Identification of Target Pair to Reduce Translocation Rate

An exemplary edited anti-CD19 CAR T cell contains four knock-outs and one knock-in. Target pairing has impact on translocation rate at cutting site. In order to reduce the

TABLE 11

| Translocation rate | | | | | | | | |
|---|---|---|---|---|---|---|---|---|
| Option | 1st EP | 2nd EP | Rep. 1 | Rep. 2 | Rep. 3 | Mean | STDEV | CV |
| 1 | Regnase, TGFBRII | TRAC, B2M | 2.0% | 1.9% | 2.5% | 2.1% | 0.3% | 15% |
| 2 | B2M, TGFBRII | TRAC, Regnase | 1.1% | 1.2% | 1.3% | 1.2% | 0.1% | 8% |
| 3 | B2M, Regnase | TRAC, TGFBRII | 1.4% | 1.4% | 1.1% | 1.3% | 0.2% | 13% |

Example 5: Manufacturing Process Development for Making Genetically Engineered T Cells Expressing an Anti-CD19 CAR and Having Genetically Disrupted Regnase-1, TGFBRII, TRAC and 112M Genes Overview An edited anti-CD19 CAR T cell product is a CD19-directed T cell immunotherapy comprised of allogeneic T cells that are genetically modified ex vivo using CRISPR/Cas9 (Clustered Regularly Interspaced Short Palindromic Repeats/CRISPR associated protein 9) gene editing components (sgRNA and Cas9 nuclease).

The modifications include targeted disruption of T cell receptor alpha constant (TRAC), β2M, TFGBRII, and Regnase-1 (Reg1). The disruption of the TRAC locus results in loss of expression of the T cell receptor (TCR) and is intended to reduce the probability of Graft versus Host Disease (GvHD), while the disruption of the β2M locus results in lack of expression of the major histocompatibility complex type I (MHC I) proteins and is intended to improve persistence by reducing the probability of host rejection. The disruption of Regnase-1 results in enhanced CAR-T expansion and efficacy. The disruption of TGFBRII is intended to improve CAR-T efficacy.

The CAR is composed of an anti-CD19 scFv, the CD8 transmembrane domain, a CD28 co-stimulatory domain, and a CD3ζ signaling domain. Sequences of the CAR components are provided in Table 8 below. Expression of the anti-CD19 CAR is driven by the EF-1α promoter.

An exemplary process flow schematic for the edited anti-CD19 CAR T cell product is depicted in FIG. 4.

Evolution of Manufacturing Process

Based on the conditions determined by the optimized processes described in Examples 1-4, the edited anti-CD19 CAR T cell product manufacturing process was performed.

Selection of the Starting Materials

The starting materials for production of edited anti-CD19 CAR T cell product include:

- leukopaks collected from healthy donors
- bacterially-derived Cas9 nuclease
- TA 1 sgRNA, which targets the TRAC locus
- B2M 1 sgRNA, which targets the B2M locus
- ZC3H12A-10 sgRNA, which targets the Regnase-1 locus
- TGFBR2-5 sgRNA, which targets the TGFBR2 locus
- rAAV-138 recombinant AAV-6 viral vector, which encodes the anti-CD19 CAR gene Structure information for the components used in making the genetic modifications of the edited anti-CD19 CAR T cell product, as well as edited TRAC, β2M, and Reg1 gene loci, is provided in Tables 3 and 5-9 below.

Manufacturing Process Description of the Edited Anti-CD19 CAR T Cell Product (i) T Cell Enrichment T cells were enriched from the leukapheresis materials (Leukopaks) via magnetic separation using a mixture of anti-CD8 and anti-CD4 antibody-coated magnetic beads using an automated cell processing system. Prior to enrichment, leukopaks were sampled for cell count and viability (≥80%).

Enriched cells were isolated in PBS/EDTA Buffer with HSA, and then sampled for cell count, viability (≥80%), T cell purity (≥70% CD3), and sterility. The cells were then centrifuged at 4±1° C. and resuspended in CryoStor CS5 at a target concentration of $50\times10^6$ viable cells/mL.

(ii) T Cell Cryopreservation

The cells were sampled for cell count, viability (≥80%) and then aliquoted into ethyl vinyl acetate cryobags at the target cell number of $2{,}500\times10^6$ cells/bag (30-70 mL of cell suspension). One Leukopak may be sufficient to produce 1-2 bags of T cells. Each bag is heat-sealed, labeled, stored at 2-8° C. until transfer to a controlled-rate freezer and subsequently transferred to vapor phase liquid nitrogen for storage.

(iii) T Cell Thawing, Activation, and First Electroporation

One frozen bag of enriched T cells was thawed, transferred into a 3 L bag and diluted into Supplemented X-VIVO™ 15 media (X-VIVO™ 15, 5% Human Serum, 100 IU/mL rhIL2, 100 IU/mL rhIL7). The cells were sampled for cell count and viability (≥70%).

The cells were seeded to a target density $2\times10^6$ viable cells/mL in static cell culture vessels, each at a total volume of approximately 500 mL of Supplemented X-VIVO™ 15 media/colloidal polymeric nanomatrix conjugated to recombinant humanized CD3 and CD28 agonists. Soluble colloidal polymeric nanomatrix conjugated to recombinant humanized CD3 and CD28 agonists solution was added at the ratio of 1:12.5 (v/v) to activate the cells.

The static cell culture vessels were incubated at 37±1° C. and 5±1% $CO_2$ for 48±4 hours. Throughout the process, whenever the static cell culture vessels are handled, they were inspected for tears and leaks, and the presence of clear, yellow medium.

The cells were centrifuged at 540 g at 20±1° C. for 15 minutes. The cell pellet was resuspended in Electroporation Buffer and centrifuged again under the same conditions. The cells were resuspended in Electroporation Buffer a second time to a target concentration of $300\times10^6$ cells/mL.

Cas9 nuclease was mixed with Regnase-1 sgRNA and TGFBRII sgRNA in a microcentrifuge tube and incubated for no less than 10 minutes at room temperature to form the ribonucleoprotein (RNP) complex. The Cas9/sgRNA was then mixed with the cells, bringing Cas9, Regnase-1 sgRNA and TGFBRII sgRNA to a final concentration of 0.27 mg/mL, 0.12 mg/mL and 0.12 mg/mL, respectively.

The mixture was aliquoted and loaded into an electroporation cassette by pipetting. Cassettes were capped and sequentially electroporated using the transfection system based on flow electroporation.

After electroporation, the cells were pooled from each cassette in a 125 mL Erlenmeyer flask and incubated at 37° C. for no less than 20 minutes. The cells were sampled for viability (≥50%) and count.

Edited cells were seeded at $2\times10^6$/mL with each total of 5 L Supplemented X-VIVO™ 15 media for recovery for 48 hours.

T cell expansion was observed before the second electroporation discussed below, which is unique for this process. See Table 12 below.

(iv) Second Electroporation and Transduction

The volume of Supplemented X-VIVO™ 15 media was reduced to a final volume of approximately 500 mL using a pump connected to the static cell culture vessel dip-tube.

The static cell culture vessel was gently swirled to allow the cells to resuspend in the media. The cells were sampled for cell count, viability (≥70%).

The cells were transferred to 500 mL centrifuge tubes and centrifuged at 540 g, at 20±1° C. for 15 minutes. The cell pellet was resuspended in Electroporation Buffer and centrifuged again under the same conditions. The cells were resuspended in Electroporation Buffer a second time to a target concentration of $300\times10^6$ cells/mL.

Cas9 nuclease was mixed with TA-1 sgRNA and with B2M-1 sgRNA in separate microcentrifuge tubes. Each solution was incubated for no less than 10 minutes at room temperature to form each ribonucleoprotein (RNP) complex. The two Cas9/sgRNA mixtures were combined, and mixed with the cells, bringing Cas9, TA-1 and B2M-1 to a final concentration of 0.3 mg/mL, 0.08 mg/mL, and 0.2 mg/mL, respectively.

The mixture was aliquoted and loaded into an electroporation cassette by pipetting. Cassettes were capped and sequentially electroporated using the transfection system based on flow electroporation.

After electroporation, the cells were pooled from each cassette in a 125 mL Erlenmeyer flask and incubated at 37° C. for no less than 20 minutes. The cells were sampled for viability (≥70%) and count. The cells were diluted to a target of $1\times10^7$ cells/mL with X-VIVO™ 15 media, and freshly thawed rAAV-138 was added at a MOI of 20,000-50,000 vg/cell. The cells were incubated at 37° C., 5% $CO_2$ for no less than 60 minutes.

(v) Cell Expansion

Cells were diluted with Supplemented X-VIVO™ 15 media, sampled for cell viability (≥70%) and count, and seeded to a density between $0.3\times10^6$ viable cells/cm$^2$ to $0.5\times10^6$ viable cells/cm$^2$ into four static cell culture vessels, and one smaller static cell culture vessel that acted as a satellite culture for cell monitoring). The static cell culture vessels were incubated at 37±1° C. and 5±1% $CO_2$.

The cell cultures were incubated for up to 9 days. During this time, the cultures were supplemented every 3 to 4 days with 100 IU/mL of rhIL2 and rhIL7 per mL of culture volume.

The satellite cell culture was tested for cell count, viability, and T cell purity throughout expansion. When the cell density in the satellite culture reaches approximately $30\times10^6$/cm$^2$ the TCRαβ depletion was performed. If cell density of the satellite does not reach $30\times10^6$/cm$^2$, TCRαβ depletion on the main cultures was performed on Day 9.

(vi) TCRαβ Depletion

The medium of each static cell culture vessel was reduced to a final volume of approximately 500 mL using a pump connected to the static cell culture vessel dip-tube. After the bulk of the media was removed, the static cell culture vessels were gently swirled to resuspend the cells in the media.

The cells were transferred to 500 mL centrifuge tubes fitted with dip-tubes that connect to the static cell culture vessel. The cells were sampled for viability (≥70%), count, and % CAR. The cells were then centrifuged at 540 g at 20±1° C. for 15 minutes. The cell pellets were resuspended and pooled in less than 650 mL PBS/EDTA containing 0.5% HSA. The cell suspension was transferred to a sterile bag which is connected to the automated cell processing system. The automated cell processing system incubates the cells with a biotin-conjugated anti-TCRαβ antibody. The cells were washed and incubated with anti-biotin magnetic beads to allow for depletion of the TCRαβ$^+$ cells using the automated cell processing system.

The cells were tested for cell count, viability (~70-92%), and % CAR cells.

(vii) Cell Recovery

The depleted cells were resuspended in Supplemented X-VIVO™ 15 media and transferred into 3 L bag(s), seeded into static cell culture vessel(s) and incubated overnight at 37±1° C. and 5±1% $CO_2$.

(viii) Cell Harvest (Drug Substance)

To harvest cells, the static cell culture vessels were removed from the incubator and allowed to rest for sedimentation of cells. The growth medium was removed from each static cell culture vessel using a pump to a final volume of approximately 500 mL. The removed media was sampled for sterility.

The static cell culture vessels were gently swirled to allow the cells to resuspend in the media. The contents of each static cell culture vessel were transferred in a 3 L transfer bag using the pump, and sampled for concentration, viability and Drug Substance lot release testing. The cells were then filtered through a 40 μm blood transfusion filter by gravity into a separate sterile 3 L bag.

The step recovery and viability from each step during the manufacturing process is shown in Table 12 and Table 13, separately.

TABLE 12

| Step Recovery | | | | | | | | |
|---|---|---|---|---|---|---|---|---|
| | Small Scale | | | | Mid Scale | Manufacture Scale | | |
| | DP Lot | | | | | | | |
| | Lot 1 | Lot 2 | Lot 3 | Lot 4 | Lot 5 | Lot 6 | Lot 7 | Lot 8 |
| | T cell Lot | | | | | | | |
| | LPT21-IO-02 | LPT21-IO-01 | LPT21-IO-03 | LPT21-IO-01 | LPT21-IO-03 | LPT20-IO-03 | LPT21-IO-03 | LPT21-IO-08 |
| Post Thawing | 83% | 78% | 77% | 82% | 89% | 72% | 79% | 79% |
| Before 1st EP | 75% | 95% | 90% | 84% | 89% | 92% | 92% | 91% |
| Post 1st EP | 58% | 61% | 60% | 56% | 93% | 73% | 81% | 79% |
| Before 2nd EP | 228% | 401% | 306% | 225% | 340% | 444% | 224% | 319% |
| Post 2nd EP/Before AAV | 47% | 69% | 58% | 83% | 91% | 71% | 82% | 85% |
| Post AAV/Before expansion | 69% | 93% | 82% | 78% | 80% | 88% | 80% | 87% |
| Post expansion/ at harvest | 7180% | 3420% | 4240% | 4630% | 7560% | 6650% | 4670% | 4900% |
| post depletion | | | n.a. | | n.a. | 87% | 87% | 73% |
| post recovery | | | n.a. | | n.a. | 84% | 69% | 64% |
| Total (till harvest) | 1923% | 3978% | 2577% | 2601% | 13703% | 8866% | 4047% | |

TABLE 13

| Viability (%) between each unit operation | | | | | | | | |
|---|---|---|---|---|---|---|---|---|
| | Small Scale | | | | Mid Scale | Manufacture Scale | | |
| | DP Lot | | | | | | | |
| | Lot 1 | Lot 2 | Lot 3 | Lot 4 | Lot 5 | Lot 6 | Lot 7 | Lot 8 |
| | T cell Lot | | | | | | | |
| | LPT21-IO-02 | LPT21-IO-01 | LPT21-IO-03 | LPT21-IO-01 | LPT21-IO-03 | LPT20-IO-03 | LPT21-IO-03 | LPT21-IO-08 |
| Post Thawing | 95 | 92 | 96 | 93 | 98 | 96 | 97 | 97 |
| Before 1st EP | 92 | 96 | 96 | 96 | 97 | 95 | 96 | 96 |
| Post 1st EP | 83 | 86 | 91 | 88 | 94 | 91 | 91 | 92 |
| Before 2nd EP | 92 | 98 | 97 | 97 | 99 | 98 | 98 | 96 |
| Post 2nd EP/Before AAV | 69 | 91 | 81 | 89 | 92 | 90 | 79 | 91 |
| Post AAV/Before expansion | 59 | 83 | 77 | 80 | 88 | 82 | 76 | 87 |
| Post expansion/ at harvest | 96 | 99 | 98 | 99 | 97 | 97 | 97 | 92 |
| Post volume reduction | | | n.a. | | | 93 | 97 | 96 |
| Post depletion | | | | | | 98 | 92 | 93 |
| Post recovery | | | | | | 97 | 94 | 92 |

Characterization of the Edited Anti-CD19 CAR T Cell Product

The edited anti-CD19 CAR T cell product is a CD19-directed T cell immunotherapy comprised of allogeneic T cells that express an anti-CD19 CAR, and that have genetically disrupted Regnase-1, TGFBRII, TRAC, and β2M genes. Flow cytometry assessment of B2M, TRAC, and CAR expression in the edited cells is shown in Table 14. For manufacture scale production, at harvest, 99.99% of the cells were TRAC$^-$, 82.6% of the cells were B2M$^-$, and 56% of the cells expressed the CAR. Editing efficiency of Regnase and TGFBRII at genomic DNA level is 97% and 86%, separately.

TABLE 14

| Editing efficiency | | | | | | | | |
|---|---|---|---|---|---|---|---|---|
| | Small Scale | | | | Mid Scale | Manufacture Scale | | |
| | DP Lot | | | | | | | |
| | Lot 1 | Lot 2 | Lot 3 | Lot 4 | Lot 5 | Lot 6 | Lot 7 | Lot 8 |
| | T cell Lot | | | | | | | |
| | LPT21-IO-02 | LPT21-IO-01 | LPT21-IO-03 | LPT21-IO-01 | LPT21-IO-03 | LPT20-IO-03 | LPT21-IO-03 | LPT21-IO-08 |
| TRAC$^-$ % | 91.3 | 97.8 | 93.8 | 94.0 | 94.1 | 99.9 | 99.9 | 99.4 |
| B2M$^-$ % | 63.8 | 81.1 | 73.5 | 71.7 | 71.7 | 82.6 | 83.0 | 82.7 |
| Regnase Indel % | 97.0 | 97.0 | 95.3 | 97.0 | 97.6 | 97.1 | 94.3 | 94.6 |
| TGFBRII Indel % | 83.6 | 88.8 | 80.6 | 85.8 | 81.2 | 85.8 | 87.7 | 81.3 |
| CAR + % | 57.8 | 52.1 | 56.9 | 49.9 | 63.6 | 56.2 | 67.6 | 66.1 |
| AAV HDR % | 46.5 | 44.2 | 39.9 | 37.9 | 51.6 | 54.7 | | n/a |

Translocation events in the anti-CD19 CAR T cell product disclosed herein were further assessed by anchor sequencing. See Table 15.

TABLE 15

| | Small Scale | | | | Mid Scale | Manufacture Scale | |
|---|---|---|---|---|---|---|---|
| | DP Lot | | | | | | |
| | Lot 1 | Lot 2 | Lot 3 | Lot 4 | Lot 5 | Lot 6 | Lot 7 |
| | T cell Lot | | | | | | |
| | LPT21-IO-02 | LPT21-IO-01 | LPT21-IO-03 | LPT21-IO-01 | LPT21-IO-03 | LPT20-IO-03 | LPT21-IO-08 |
| Translocation (Anchor Seq) | 2.0% | 1.9% | 2.5% | 1.8% | 1.7% | 1.8% | |

The various lots of anti-CD19 CAR T cell product was further characterized by subset phenotype analysis and exhaustion phenotype analysis. Example flow panels are shown in Table 16. The various lots were assessed for memory cell markers. Within viable CAR+, CD4+CAR+, and CD8+CAR+ populations, CD45RA+CD62L+ cells, CD45RA-CD62L+ cells, CD45RA-CD62L− cells, and CD45RA+CD62L− cells were defined as Naïve T cells, central memory (CM) T cells, effector memory (EM) T cells, and terminal effector (TE) T cells, respectively. These populations within the anti-CD19 CAR T cell product were defined as subsets. FIGS. 9A-9D show the percentage of naïve, terminal effector (TE), effector memory (EM), and central memory (CM) cells in total viable cells (FIG. 9A), CAR+ cells (FIG. 9B), CD4+ CAR+ cells (FIG. 9C), and CD8+ CAR+ cells (FIG. 9D) of Lots 1-7. Greater than 90% Viable cells, CAR+ cells, and CD4+ CAR+ cells are composed of Naïve T cells, CM and EM in Lots of 1-7. In 4 out of 7 Lots, there are greater 90% of Naïve T cells, CM and EM within CD8+ CAR+ cells while 80%-90% of Naïve T cells, CM and EM were seen in other 3 out of 7 lots.

TABLE 16

Flow Panels for Characterization of T Cell Populations

| Exhaustion | Subset |
|---|---|
| CD4 | CD4 |
| CD8 | CD8 |
| CAR | CD45RO |
| CD57 | CD45RA |
| Lag3 | CD62L |
| PD1 | CD27 |
| Tim3 | |

Translocation events in the anti-CD19 CAR T cell product disclosed herein are to be further assessed ddPCR. Further, the anti-CD19 CAR T cell product is to be further characterized, for example, by karyotyping.

In Vitro Cell Killing Assay

The potency of the anti-CD19 CAR T cell product from manufacturing scale lots was assessed. In addition, the potency of the TCRα/β-depleted anti-CD19 CAR with genetically disrupted TRAC and β2M genes and with or without disrupted Regnase-1 and TGFBRII genes was compared. Two different tumor cell lines, Nalm6 and Raji, were evaluated. Table 17 lists the cell samples tested.

TABLE 17

Description of CAR T cell samples tested

| Sample ID | Sample Description |
|---|---|
| Control | Untreated control (T cells with no edits) |
| EP control | Only EP1, EP2 performed (no transduction) |
| Reference | TCRα/β depleted anti-CD19 CAR T with disrupted TRAC and β2M genes |
| Lot 4 | anti-CD19 CAR T with disrupted TRAC, β2M, Regnase-1 and TGFBRII genes (undepleted) |
| Lot 5 | anti-CD19 CAR T with disrupted TRAC, β2M, Regnase-1 and TGFBRII genes (undepleted) |
| Lot 6 | TCRa/b depleted anti-CD19 CAR T cells with disrupted TRAC, β2M, Regnase-1 and TGFBRII genes - Manufacturing Scale Lot #1 |
| Lot 7 | TCRa/b depleted anti-CD19 CAR T cells with disrupted TRAC, β2M, Regnase-1 and TGFBRII genes - Manufacturing Scale Lot #2 |
| Lot 8 | TCRa/b depleted anti-CD19 CAR T cells with disrupted TRAC, β2M, Regnase-1 and TGFBRII genes - Manufacturing Scale Lot #3 |

The ability of CART or control T cells to kill target cells was assessed using a flow cytometry-based cytotoxicity assay. Target cells were labeled with 5 μM efluor670 (Thermo Fisher Scientific, Waltham, MA), washed and incubated overnight (50,000 target cells/well; 96-well U-bottom plate [Corning, Tewksbury, MA]) in co-cultures with CART or control T cells at varying ratios. The next day, wells were washed and media was replaced with 200 μL of fresh media containing a 1:500 dilution of 5 mg/mL 4',6-diamidino-2-phenylindole (DAPI) (Thermo Fisher Scientific, Waltham, MA) to enumerate dead/dying cells. Finally, 25 μL of CountBright beads (Thermo Fisher Scientific) was added to each well, and cells were then analyzed by flow cytometry using a Novocyte flow cytometer (ACEA Biosciences, San Diego, California). Flowjo software (v10, Flowjo, Ashland, OR) was used to analyze flow cytometry data files (fcs files).

Cells per μL were calculated from analyzed flow cytometry data using the following equation:

Cells/μL=((number of live [DAPI negative] target cell events)/(number of bead events))×((Assigned bead count of lot(beads/50 μL))/(volume of sample))

Total cells were calculated by multiplying cells/μL×the total volume of cells.

The percent cell lysis was then calculated using the following equation:

% Cell lysis=(1−((Total Number of target Cells in Test Sample)/(Total Number of Target Cells in Control Sample))×100

Comparable results have been obtained with or without the use of counting beads. When counting beads were not used gated live events for target and control samples were used in the percent lysis calculation.

The results are presented in FIGS. 12A, 12B, 13A, and 13B (see also Tables 18 and 19). The average % lysis of Nalm6 cells for TCRα/β-depleted anti-CD19 CAR T cells with disrupted TRAC, β2M, Regnase-1 and TGFBRII genes at 0.5:1 ratio of drug product:Nalm6 cells was 78% and at 1:1 ratio was 87%. The increase in potency of this CAR T product compared to TCRα/β-depleted anti-CD19 CAR T cells with disrupted TRAC and β2M genes was 9% and 12%, respectively. The average % lysis of Raji cells for TCRα/β-depleted anti-CD19 CAR T cells with disrupted TRAC, β2M, Regnase-1 and TGFBRII genes at 0.5:1 ratio of drug product:Raji cells was 36% and at 1:1 ratio was 44%. The increase in potency of this CART product compared to TCRα/β-depleted anti-CD19 CAR T cells with disrupted TRAC and β2M genes was 23% and 36% respectively.

TABLE 18

| % lysis of NALM target cells | | |
|---|---|---|
| Sample ID | 0.5:1 ratio | 1:1 ratio |
| Control | 13 | 39 |
| EP control | 28 | 37 |
| Reference | 68 | 75 |
| Lot 4 | 33 | 69 |
| Lot 5 | 89 | 86 |
| Lot 6 | 56 | 83 |
| Lot 7 | 87 | 87 |
| Lot 8 | 90 | 92 |

TABLE 19

| % lysis of Raji target cells | | |
|---|---|---|
| Sample ID | 0.5:1 ratio | 1:1 ratio |
| Control | 7 | 15 |
| EP control | 9 | 15 |
| Reference | 13 | 8 |
| Lot 4 | 13 | 7 |
| Lot 5 | 22 | 25 |
| Lot 6 | 14 | 11 |
| Lot 7 | 40 | 47 |
| Lot 8 | 53 | 73 |

This demonstrates that the potency of the TCRα/β-depleted anti-CD19 CAR T cells with disrupted TRAC, β2M, Regnase-1 and TGFBRII genes in all the large-scale Manufacturing lots relative to each other was consistent across both ratios and cell lines. This also demonstrates that TCRα/β-depleted anti-CD19 CAR T cells with disrupted TRAC, β2M, Regnase-1 and TGFBRII genes were more potent than TCRα/β-depleted anti-CD19 CAR T cells with disrupted TRAC and β2M genes.

In Vivo Efficacy Assay

The potency of the TCRα/β-depleted anti-CD19 CAR T cell product with genetically disrupted TRAC and β2M genes and with or without disrupted Regnase-1 and TGFBRII genes was assessed and evaluated in in vivo models with Nalm6, JEKO, and Raji-LUC.

Intravenous Disseminated NAME and RAJI-1 Tumor Xenograft Model

In brief, 5-8 week old female CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. At the start of the study, the mice were divided into treatment groups. The mice were inoculated with Nalm6-Fluc-GFP (Nalm6-Fluc-Neo/eGFP—Puro) cells intravenously to model disseminated disease. On Day 1, all mice received an intravenous injection of 0.5×10$^6$ Nalm6 or RAJI-1 cells/mouse. On Day 4, mice received an intravenous injection of CAR T cells. During the course of the study, the mice were monitored daily and body weight was measured two times weekly. Bioluminescence (BLI; total ROI, photon/s) was measured twice weekly beginning on Day 4 of the study. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

- Loss of body weight of 20% or greater sustained for a period of greater than 1 week;
- Tumors that inhibit normal physiological function such as eating, drinking, mobility and ability to urinate and or defecate;
- Prolonged, excessive diarrhea leading to excessive weight loss (>20%); or
- Persistent wheezing and respiratory distress.
- Animals were also considered moribund if there was prolonged or excessive pain or distress as defined by clinical observations such as: prostration, hunched posture, paralysis/paresis, distended abdomen, ulcerations, abscesses, seizures and/or hemorrhages.

Subcutaneous JeKo-1 Tumor Xenograft Model

Efficacy of CAR T cells were evaluated in the Subcutaneous Model using methods employed by Translations Drug Development, LLC (Scottsdale, AZ) and described herein. In brief, 5-8 week old female CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. At the start of the study, the mice were divided into treatment groups. On Day 1 mice received an intravenous injection of 5×10$^6$ JeKo-1 cells/mouse subcutaneously in the right flank. At an average tumor size 150 mm$^3$, mice received a single 200 μl intravenous dose of CAR T cells per. Tumor volume and body weight was recorded twice weekly; gross observations daily. Tumor volume is calculated using this formula:

$$(mm^3)=(a\times b^2/2) \text{ where '}b\text{' is the smallest diameter and '}a\text{' is the largest diameter.}$$

'n.d.' indicates no data since the mice did not survive

Results

The in vivo efficacy of the CAR-T cells in the xenograft mouse models described herein is measured by levels of Bioluminescence (BLI) as shown in FIGS. 14A, 15A, and 16A and Tables 20-22.

TABLE 20

| BLI (×10$^6$) in NALM6 model | | | | | | |
|---|---|---|---|---|---|---|
| | | Cell Number | | | | |
| Days | Untreated | 0.5 × 10$^6$ | 1 × 10$^6$ | 2 × 10$^6$ | 4 × 10$^6$ | 10 × 10$^6$ |
| 4 | 66 | 78 | 68 | 56 | 58 | 66 |
| 11 | 45040 | 199 | 439 | 46 | 44 | 48 |
| 18 | 306200 | 336 | 383 | 356 | 371 | 374 |
| 25 | n.d. | 422 | 431 | 422 | 415 | 482 |
| 32 | n.d. | 460 | 454 | 525 | 419 | 406 |
| 39 | n.d. | 51 | 51 | 41 | 48 | 52 |
| 46 | n.d. | 54 | 47 | 37 | 40 | 42 |
| 53 | n.d. | 1 | 1 | 1 | 1 | 1 |
| 60 | n.d. | 1 | 1 | 1 | 1 | 1 |
| 67 | n.d. | 1 | 1 | 1 | 1 | 1 |

TABLE 21

| BLI (×10$^6$) in Raji model | | | | | | |
|---|---|---|---|---|---|---|
| | | Cell Number | | | | |
| Days | Untreated | 0.5 × 10$^6$ | 1 × 10$^6$ | 2 × 10$^6$ | 4 × 10$^6$ | 10 × 10$^6$ |
| 4 | 12 | 20 | 18 | 23 | 22 | 21 |
| 11 | 3554 | 244 | 32 | 37 | 35 | 21 |
| 18 | n.d. | 1488 | 201 | 83 | 21 | 21 |

TABLE 21-continued

| BLI (×10^6) in Raji model | | | | | | |
|---|---|---|---|---|---|---|
| | | Cell Number | | | | |
| Days | Untreated | 0.5 × 10^6 | 1 × 10^6 | 2 × 10^6 | 4 × 10^6 | 10 × 10^6 |
| 25 | n.d. | 1853 | 592 | 198 | 76 | 22 |
| 32 | n.d. | 2503 | 807 | 428 | 118 | 30 |
| 39 | n.d. | 4152 | 1428 | 627 | 338 | 111 |
| 46 | n.d. | 8536 | 1573 | 1252 | 843 | 189 |
| 53 | n.d. | 4513 | 2115 | 2180 | 1706 | 385 |

TABLE 22

| BLI in JEKO model | | | | | | |
|---|---|---|---|---|---|---|
| | | Cell Number | | | | |
| Days | Untreated | 0.5 × 10^6 | 1 × 10^6 | 2 × 10^6 | 4 × 10^6 | 10 × 10^6 |
| 1 | 167 | 166 | 165 | 165 | 165 | 167 |
| 5 | 547 | 574 | 474 | 350 | 282 | 278 |
| 8 | 954 | 957 | 581 | 473 | 318 | 302 |
| 11 | 1543 | 1233 | 801 | 488 | 343 | 310 |
| 15 | 2295 | 1143 | 366 | 264 | 235 | 258 |
| 18 | 1886 | 549 | 140 | 110 | 140 | 226 |
| 22 | n.d. | 587 | 46 | 10 | 103 | 179 |
| 25 | n.d. | 582 | 3 | 8 | 56 | 120 |
| 29 | n.d. | 529 | 0 | 2 | 13 | 57 |
| 32 | n.d. | 456 | 0 | 0 | 6 | 19 |
| 36 | n.d. | 422 | 0 | 0 | 3 | 4 |
| 40 | n.d. | 543 | 0 | 0 | 2 | 2 |
| 43 | n.d. | 776 | 0 | 6 | 1 | 0 |

FIGS. 14B, 15B, and 16B show the survival rates. In the Nalm6 tumor model, only 1 mouse in the 4×10^6 CAR T cell group was euthanized on day 67, and 2 mice in the 10×10^6 CAR T cell group were euthanized on days 49 and 55. All the mice in the untreated group were euthanized on days 20-21. In the Raji tumor model, all the mice in the untreated group were euthanized on day 18. One mouse in the 0.5×10^6 CAR T cell group was euthanized on day 53 while all the mice in the other groups survived. In the JEKO tumor model, all the mice in the untreated group were euthanized by day 18. One mouse in the 0.5×10^6 CAR T cell group was euthanized on day 43, while 2 mice in the 10×10^6 CAR T cell group was euthanized on days 5 and 7.

Example 6: Identification of Target Pair to Reduce Translocation Rate in the Edited Anti-CD70 CAR T Cells An exemplified population of edited anti-CD70 CAR T cells contained five disrupted endogenous genes (knock-outs) and one exogenous nucleic acid (knock-in) encoding the anti-CD70 CAR. Pairing of the guide RNAs targeting the endogenous genes may have impact on translocation rate at the cutting sites. In order to reduce the number of translocation species generated from single electroporation event, five knockout targets were splinted into 2 electroporation events with two or three knockout targets in each electroporation. The predicted translocation rates from three target pair options are listed in Table 23. The prediction was based on historical translocation data generated from different experiments.

TABLE 23

| Predicted translocation rate | | | |
|---|---|---|---|
| Option | 1st Electroporation | 2nd Electroporation | Predicted translocation rate |
| 1 | CD70, TGFBRII | TRAC, B2M, Regnase-1 | 2.9 |
| 2 | B2M, Reganse-1 | TRAC, CD70, TGFBRII | 4.0 |
| 3 | B2M, Regnase-1, TGFBRII | TRAC, CD70 | 4.4 |

A small scale process with proposed target pairing in Table 24 were performed in T cells from three to four different donors. Translocation rates were assessed with Anchor seq on the edited anti-CD70 CAR T cells harvested after 7 days expansion. Translocation rates from three target pairing options were between 3.0%-5.0%. See Table 24.

TABLE 24

| Translocation rate | | | | | | | | | |
|---|---|---|---|---|---|---|---|---|---|
| Option | 1st EP | 2nd EP | Rep. 1 | Rep. 2 | Rep. 3 | Rep. 4 | Mean | STDEV | Cv |
| 1 | CD70, TGFBRII | TRAC, B2M, Regnase-1 | 3.40% | 4.90% | 5.80% | 4.30% | 4.60% | 1.01% | 21.96% |
| 2 | B2M, Reganse-1 | TRAC, CD70, TGFBRII | 3.50% | 2.90% | 3.70% | n.a | 3.37% | 0.42% | 12.37% |
| 3 | B2M, Regnase-1, TGFBRII | TRAC, CD70 | 3.80% | 4.00% | 5.00% | 4.80% | 4.40% | 0.59% | 13.38% |

Translocation rates for Option 3 (B2M, Regnase-1, TGFBRII in 1st EP and TRAC and CD70 in 2nd EP) were assessed with Anchor seq and ddPCR and compared between small scale and manufacturing lots for on the edited anti-CD70 CAR T cells harvested after 7 days expansion. Translocation rates between small scale and manufacture scale were comparable. See Table 25.

TABLE 25

| Translocation Data | | | | |
|---|---|---|---|---|
| | | Small Scale | | Manufacture |
| | | DP Lot | | |
| | | Lot 1 | Lot 2 | Scale Lot 3 |
| | | T cell Lot | | |
| | | LPT21-IO-01 | LPT20-IO-15 | LPT21-IO-02 |
| Translocation | Anchor Seq | 3.80% | 4.00% | 3.90% |
| | ddPCR | 4.7% | 5.7% | 5.5% |

Example 7: Identification of Optimized Conditions for Disruption of TRAC Paired with CD70

This Example reports identification of optimized TA-1 guide amount and Cas9 amount for disruption of TRAC using CRISPR-Cas9 dependent gene editing when paired with CD70 editing.

In brief, genetically engineered T cells were manufactured in a small-scale process, in which RNP complexes targeting TRAC and CD70 were added after 48 hrs activation. Table 26 shows the amounts of TA-1 guide tested, where TA-1 sgRNA 1× was 160 μg/mL and Cas9 1× was 150 μg/mL. The amount of sgRNA and Cas9 targeting CD70 remained constant: 160 μg/mL for CD70-7 sgRNA and 150 μg/mL for Cas9. With the goal to maintain >95% TRAC editing, >95% CD70 editing and high CAR+% (as determined by flow cytometry; FIGS. 6A-6C, Table 26), the optimal dose for TRAC knockout when electroporated with CD70 was TA-1 sgRNA of 120 μg/mL and Cas9 of 150 μg/mL.

TABLE 26

| TRAC-% and CD70-% upon Different TA-1 sgRNA and Cas9 Doses | | | | | |
|---|---|---|---|---|---|
| EP Groups | TA-1 sgRNA | CAS9 | TRAC-% | CD70-% | CAR+% |
| 1 | 1X | 1X | 98.91 | 99.81 | 77.55 |
| 2 | 0.75X | 1X | 98.30 | 99.85 | 77.24 |
| 3 | 0.5X | 1X | 97.48 | 99.80 | 73.18 |
| 4 | 0.25X | 1X | 82.02 | 99.86 | 54.14 |

Example 8: Identification of Optimized Conditions for Disruption of Regnase-1 when Paired with 112M This Example reports identification of optimized Regnase-1 guide amount and Cas9 amount for disruption of Regnase-1 using CRISPR-Cas9 dependent gene editing.

In brief, genetically engineered T cells were manufactured in a small-scale process in which RNP complexes targeting Regnase-1 were added after 48 hrs activation. Table 27 shows the amounts of Regnase-1 guide and Cas9 tested when electroporated together with B2M-1, where Regnase sgRNA 1× was 160 μg/mL, Cas9 1× was 150 μg/mL. B2M-1 sgRNA and Cas9 dose targeting B2M locus remained constant as 200 μg/mL for sgRNA and 150 μg/mL for Cas9. The goal was to maintain high Regnase-1 editing (as determined by TIDE (FIGS. 7A-7B, Table 27) and high B2M editing (as determined by flow cytometry, FIGS. 7A-7B, Table 27). 0.75× and 0.5× Regnase sgRNA maintained Regnase-1 editing above 95%. 0.75×, 0.5× and 0.25× Cas9 maintained Regnase editing above 95%. However, decrease in Cas9 did not increase B2M editing efficiency, which was maintained at 75-80%. Decrease in Regnase sgRNA to 0.5× and 0.25× increased B2M editing above 80%. Considering combined outcome of Regnase editing (>95%) and B2M editing (>80%), the optimal dose for Regnase knockout when electroporated with β2M was Regnase-1 sgRNA of 80 μg/mL and Cas9 of 150 μg/mL.

TABLE 27

| Regnase Indel % and B2M-% upon Different sgRNA and Cas9 Doses | | | | |
|---|---|---|---|---|
| EP Groups | Regnase-1 sgRNA | CAS9 | Regnase Indel % | β2M⁻% (flow cytometry) |
| 1 | 1X | 1X | 95.4 | 76.5 |
| 2 | 0.75X | 1X | 95.9 | 78.6 |
| 3 | 0.5X | 1X | 95.4 | 81.8 |
| 4 | 0.25X | 1X | 93.7 | 84.5 |
| 5 | 0.125X | 1X | 91.5 | 86 |
| 6 | 1X | 0.75X | 95.6 | 78.2 |
| 7 | 1X | 0.5X | 96.1 | 78.6 |
| 8 | 1X | 0.25X | 95.2 | 77.4 |
| 9 | 1X | 0.125X | 91 | 78.6 |

Example 9: Identification of Optimized Conditions for Disruption of TGFBRII

This Example reports identification of optimized TGFBRII guide amount and Cas9 amount for knockout of TGFBRII using CRISPR-Cas9 dependent gene editing.

In brief, genetically engineered T cells were manufactured in a small-scale process in which RNP complexes targeting TGFBRII were added to the T cells after 48 hrs activation. Table 28 shows the amounts of TGFBRII guide and Cas9 tested, where TGFBRII sgRNA 1× was 160 μg/mL and Cas9 1× was 150 μg/mL.

With the goal to maintain greater than 80% TGFBRII editing (as determined by TIDE; FIG. 3), the optimal dose for TGFBRII knockout was TGFBRII sgRNA of 120 μg/mL and Cas9 of 120 μg/mL.

TABLE 28

TGFBRII Indel % upon Different sgRNA and Cas9 Doses

| EP Groups | TGFBRII | CAS9 | Indel %-1 | Indel %-2 Day 4 | Average | Indel %-1 | Indel %-2 day 7/8 | Average |
|---|---|---|---|---|---|---|---|---|
| 1 | 1X | 1X | 87.1 | 90 | 88.55 | 82.7 | 88.1 | 85.4 |
| 2 | 2X | 1X | 86.4 | NA | 86.4 | 83 | NA | 83 |
| 3 | 0.75X | 1X | 83.7 | 87.8 | 85.75 | 81.7 | 89.5 | 85.6 |
| 4 | 0.5X | 1X | 81.7 | NA | 81.7 | 80.6 | NA | 80.6 |
| 5 | 0.25X | 1x | 46.1 | NA | 46.1 | 55.8 | NA | 55.8 |
| 6 | 1X | 2X | 83.8 | NA | 83.8 | 89.4 | NA | 89.4 |
| 7 | 1X | 0.75X | 86.3 | 90.7 | 88.5 | 84.4 | 90.3 | 87.35 |
| 8 | 1X | 0.5X | 87.1 | NA | 87.1 | 81.7 | NA | 81.7 |
| 9 | 1x | 0.25x | 73.1 | NA | 73.1 | 74.7 | NA | 74.7 |
| 10 | 0.75X | 0.75X | NA | 90.3 | 90.3 | NA | 89.4 | 89.4 |

Example 10: Manufacturing Process Development for Making Genetically Engineered T Cells Expressing an Anti-CD70 CAR and Having Genetically Disrupted Regnase-1, TGFBRII, CD70, TRAC and 112M Genes Overview An edited anti-CD70 CAR T cell product is a CD70-directed T cell immunotherapy comprised of allogeneic T cells that are genetically modified ex vivo using CRISPR/Cas9 (Clustered Regularly Interspaced Short Palindromic Repeats/CRISPR associated protein 9) gene editing components (sgRNA and Cas9 nuclease).

The modifications include targeted disruption of T cell receptor alpha constant (TRAC), β2M, CD70, TFGBRII, and Regnase-1. The disruption of the TRAC locus results in loss of expression of the T cell receptor (TCR) and is intended to reduce the probability of Graft versus Host Disease (GvHD), while the disruption of the β2M locus results in lack of expression of the major histocompatibility complex type I (MHC I) proteins and is intended to improve persistence by reducing the probability of host rejection. Disruption of CD70 locus to downregulate CD70 surface expression reduces target driven fratricide of CAR T cells. The disruption of Regnase-1 results in enhanced CAR-T expansion and efficacy. The disruption of TGFBRII is intended to improve CAR-T efficacy.

The CAR is composed of a humanized CD70 single chain variable fragment (scFv) derived from murine antibody clone 1F6 (a previously characterized anti-CD70 monoclonal antibody), the CD8 transmembrane domain, a 41-BB co-stimulatory domain, and a CD3ζ signaling domain. Expression of the anti-CD70 CAR is driven by the EF-1α promoter.

An exemplary process flow schematic for the edited anti-CD70 CAR T cell product manufacturing process is depicted in FIG. 8.

Evolution of Manufacturing Process

Based on the conditions determined by the optimized processes described in Examples 1 and 6-10, the edited anti-CD70 CAR T cell product manufacturing process was performed.

Selection of the Starting Materials

The starting materials for production of edited anti-CD70 CAR T cell product include:

- leukopaks collected from healthy donors
- bacterially-derived Cas9 nuclease
- TA 1 sgRNA, which targets the TRAC locus
- B2M 1 sgRNA, which targets the B2M locus
- CD70-7 sgRNA, which targets the CD70 locus
- ZC3H12A-10 sgRNA, which targets the Regnase-1 locus
- TGFBR2-5 sgRNA, which targets the TGFBR2 locus
- rAAV-145b recombinant AAV-6 viral vector, which encodes the anti-CD70 CAR gene Structure information for the components used in making the genetic modifications of the edited anti-CD70 CAR T cell product, as well as edited TRAC, B2M, and CD70 gene loci, is provided in Tables 3, 5, 6, 8, and 9 below.

Manufacturing Process Description of the Edited Anti-CD70 CAR T Cell Product (i) T Cell Enrichment T cells were enriched from the leukapheresis materials (Leukopaks) via magnetic separation using a mixture of anti-CD8 and anti-CD4 antibody-coated magnetic beads using an automated cell processing system. Prior to enrichment, leukopaks were sampled for cell count and viability (≥80%).

Enriched cells were isolated in PBS/EDTA Buffer with HSA, and then sampled for cell count, viability (≥80%), T cell purity (≥70% CD3), and sterility. The cells were then centrifuged at 4±1° C. and resuspended in CryoStor CS5 at a target concentration of $50\times10^6$ viable cells/mL.

(ii) T Cell Cryopreservation

The cells were sampled for cell count, viability (≥80%) and then aliquoted into ethyl vinyl acetate cryobags at the target cell number of $2{,}500\times10^6$ cells/bag (30-70 mL of cell suspension). One Leukopak may be sufficient to produce 1-2 bags of T cells. Each bag is heat-sealed, labeled, stored at 2-8° C. until transfer to a controlled-rate freezer and subsequently transferred to vapor phase liquid nitrogen for storage.

(iii) T Cell Thawing, Activation, and First Electroporation

One frozen bag of enriched T cells was thawed, transferred into a 3 L bag and diluted into Supplemented X-VIVO™ 15 media (X-VIVO™ 15, 5% Human Serum, 100 IU/mL rhIL2, 100 IU/mL rhIL7). The cells were sampled for cell count and viability (≥70%).

The cells were seeded to a target density $2\times10^6$ viable cells/mL in static cell culture vessels, each at a total volume of approximately 500 mL of Supplemented X-VIVO™ 15 media/colloidal polymeric nanomatrix conjugated to recombinant humanized CD3 and CD28 agonists. Soluble colloidal polymeric nanomatrix conjugated to recombinant humanized CD3 and CD28 agonists solution was added at the ratio of 1:12.5 (v/v) to activate the cells.

The static cell culture vessels were incubated at 37±1° C. and 5±1% $CO_2$ for 48±4 hours. Throughout the process, whenever the static cell culture vessels are handled, they were inspected for tears and leaks, and the presence of clear, yellow medium.

The cells were centrifuged at 540 g at 20±1° C. for 15 minutes. The cell pellet was resuspended in Electroporation Buffer and centrifuged again under the same conditions. The cells were resuspended in Electroporation Buffer a second time to a target concentration of $300\times10^6$ cells/mL.

Cas9 nuclease was mixed with B2M-1 sgRNA, Regnase-1 sgRNA and TGBRII sgRNA in a microcentrifuge tube and incubated for no less than 10 minutes at room temperature to form the ribonucleoprotein (RNP) complex. The Cas9/sgRNA was then mixed with the cells, bringing Cas9, B2M sgRNA, Regnase-1 sgRNA and TGFBRII sgRNA to a final concentration of 0.42 mg/mL, 0.20 mg/mL 0.08 mg/mL, and 0.12 mg/mL, respectively.

The mixture was aliquoted and loaded into an electroporation cassette by pipetting. Cassettes were capped and sequentially electroporated using the transfection system based on flow electroporation.

After electroporation, the cells were pooled from each cassette in a 125 mL Erlenmeyer flask and incubated at 37° C. for no less than 20 minutes. The cells were sampled for viability (≥50%) and count.

Edited cells were seeded at $2\times10^6$/mL with each total of 5 L Supplemented X-VIVO™ 15 media for recovery for 48 hours.

(iv) Second Electroporation and Transduction

The volume of Supplemented X-VIVO™ 15 media was reduced to a final volume of approximately 500 mL using a pump connected to the static cell culture vessel dip-tube.

The static cell culture vessel was gently swirled to allow the cells to resuspend in the media. The cells were sampled for cell count, viability (≥70%).

The cells were transferred to 500 mL centrifuge tubes and centrifuged at 540 g, at 20±1° C. for 15 minutes. The cell pellet was resuspended in Electroporation Buffer and centrifuged again under the same conditions. The cells were resuspended in Electroporation Buffer a second time to a target concentration of $300\times10^6$ cells/mL.

Cas9 nuclease was mixed with CD70-7 sgRNA and with TA-1 sgRNA in one microcentrifuge tubes. Solution was incubated for no less than 10 minutes at room temperature to form ribonucleoprotein (RNP) complex. The Cas9/sgRNA mixtures were mixed with the cells, bringing Cas9, CD70-7 and TA-1 to a final concentration of 0.3 mg/mL, 0.16 mg/mL, and 0.12 mg/mL, respectively.

The mixture was aliquoted and loaded into an electroporation cassette by pipetting. Cassettes were capped and sequentially electroporated using the transfection system based on flow electroporation.

After electroporation, the cells were pooled from each cassette in a 125 mL Erlenmeyer flask and incubated at 37° C. for no less than 20 minutes. The cells were sampled for viability (≥70%) and count. The cells were diluted to a target of $1\times10^7$ cells/mL with X-VIVO™ 15 media, and freshly thawed rAAV-145b was added at a MOI of 20,000-50,000 vg/cell. The cells were incubated at 37° C., 5% $CO_2$ for no less than 60 minutes.

(v) Cell Expansion

Cells were diluted with Supplemented X-VIVO™ 15 media, sampled for cell viability (≥70%) and count, and seeded to a density between $0.3\times10^6$ viable cells/cm$^2$ to $0.5\times10^6$ viable cells/cm$^2$ into four static cell culture vessels, and one smaller static cell culture vessel that acted as a satellite culture for cell monitoring). The static cell culture vessels were incubated at 37±1° C. and 5±1% $CO_2$.

The cell cultures were incubated for up to 9 days. During this time, the cultures were supplemented every 3 to 4 days with 100 IU/mL of rhIL2 and rhIL7 per mL of culture volume.

The satellite cell culture was tested for cell count, viability, and T cell purity throughout expansion. When the cell density in the satellite culture reaches approximately $30\times10^6$/cm$^2$ the TCRαβ depletion was performed. If cell density of the satellite does not reach $30\times10^6$/cm$^2$, TCRαβ depletion on the main cultures was performed on Day 9.

(vi) TCRαβ Depletion

The medium of each static cell culture vessel was reduced to a final volume of approximately 500 mL using a pump connected to the static cell culture vessel dip-tube. After the bulk of the media was removed, the static cell culture vessels were gently swirled to resuspend the cells in the media.

The cells were transferred to 500 mL centrifuge tubes fitted with dip-tubes that connect to the static cell culture vessel. The cells were sampled for viability (≥70%), count, and % CAR. The cells were then centrifuged at 540 g at 20±1° C. for 15 minutes. The cell pellets were resuspended and pooled in less than 650 mL PBS/EDTA containing 0.5% HSA. The cell suspension was transferred to a sterile bag which is connected to the automated cell processing system. The automated cell processing system incubates the cells with a biotin-conjugated anti-TCRαβ antibody. The cells were washed and incubated with anti-biotin magnetic beads to allow for depletion of the TCRαβ$^+$ cells using the automated cell processing system.

The cells were tested for cell count, viability (≥70%), and % CAR cells.

(vii) Cell Recovery

The depleted cells were resuspended in Supplemented X-VIVO™ 15 media and transferred into 3 L bag(s), seeded into static cell culture vessel(s) and incubated overnight at 37±1° C. and 5±1% $CO_2$.

(viii) Cell Harvest (Drug Substance)

To harvest cells, the static cell culture vessels were removed from the incubator and allowed to rest for sedimentation of cells. The growth medium was removed from each static cell culture vessel using a pump to a final volume of approximately 500 mL. The removed media was sampled for sterility.

The static cell culture vessels were gently swirled to allow the cells to resuspend in the media. The contents of each static cell culture vessel were transferred in a 3 L transfer bag using the pump, and sampled for concentration, viability and Drug Substance lot release testing. The cells were then filtered through a 40 μm blood transfusion filter by gravity into a separate sterile 3 L bag.

The step recovery and viability from each step during the manufacturing process is shown in Table 29 and Table 30, separately. The RNP dose for the manufacture scale observations was TRAC-adjusted and the depletion day was on Day 10 (6 days expansion).

TABLE 29

| Step Recovery | | | | | |
|---|---|---|---|---|---|
| | Small Scale | | Manufacture Scale DP Lot | | |
| | Lot 1 | Lot 2 | Lot 3 T cell Lot | Lot 4 | Lot 5 |
| | LPT21-IO-01 | LPT20-IO-15 | LPT21-IO-02 | LPT21-IO-05 | LPT21-IO-09 |
| Post Thawing | 82% | 79% | 79% | 79% | 88% |
| Before 1st EP | 84% | 94% | 73% | 95% | 94% |
| Post 1st EP | 64% | 62% | 67% | 91% | 77% |
| Before 2nd EP | 271% | 332% | 277% | 244% | 220% |
| Post 2nd EP/Before AAV | 65% | 77% | 74% | 75% | 77% |
| Post AAV/Before expansion | 67% | 91% | 91% | 69% | 74% |
| Post expansion/at harvest | 7030% | 5210% | 6030% | 7361% | 4936% |
| post depletion | n.a. | | 84% | 69% | 79% |
| post recovery | | | 97% | 79% | 92% |
| Total (till harvest) | 3658% | 5602% | 4414% | 4745% | 3011% |
| % Increase | 305% | 467% | 368% | 395% | 251% |

TABLE 30

| Viability (%) between Each Unit Operation | | | | | |
|---|---|---|---|---|---|
| | Small Scale | | Manufacture Scale DP Lot | | |
| | Lot 1 | Lot 2 | Lot 3 T cell Lot | Lot 4 | Lot 5 |
| | LPT21-IO-01 | LPT20-IO-15 | LPT21-IO-02 | LPT21-IO-05 | LPT21-IO-09 |
| Post Thawing | 93 | 97 | 96 | 98 | 98 |
| Before 1st EP | 96 | 95 | 94 | 97 | 96 |
| Post 1st EP | 85 | 91 | 86 | 95 | 94 |
| Before 2nd EP | 96 | 98 | 95 | 97 | 96 |
| Post 2nd EP/Before AAV | 82 | 90 | 85 | 91 | 90 |
| Post AAV/Before expansion | 75 | 85 | 74 | 86 | 79 |
| Post expansion/at harvest | 97 | 98 | 97 | 97 | 97 |
| Post volume reduction | | | 97 | 96 | 97 |
| Post depletion | | | 98 | 96 | 98 |
| Post recovery | | | 97 | 98 | 97 |

Characterization of the Edited Anti-CD70 CAR T Cell Product

The edited anti-CD70 CAR T cell product is a CD70 directed T cell immunotherapy comprised of allogeneic T cells that express an anti-CD70 CAR, and that have genetically disrupted CD70, Regnase-1, TGFBRII, TRAC, and β2M genes. Flow cytometry assessment of B2M, TRAC, CD70 and CAR expression in the edited cells is shown in Table 31. For manufacture scale production, at harvest, 99.98% of the cells were $TRAC^{-}$, 65.91% of the cells were B2M−, 99.98% of the cells were $CD70^{-}$, and 80.54% of the cells expressed the CAR. HDR indicating CD70 CAR cassette integration at genomic DNA level was 76.10%. Editing efficiency of Regnase and TGFBRII at genomic DNA level was 95.20% and 85.80%, separately.

TABLE 31

| Editing efficiency | | | | | |
|---|---|---|---|---|---|
| | Small Scale | | Manufacture Scale DP Lot | | |
| | Lot 1 | Lot 2 | Lot 3 T cell Lot | Lot 4 | Lot 5 |
| | LPT21-IO-01 | LPT20-IO-15 | LPT21-IO-02 | LPT21-IO-05 | LPT21-IO-09 |
| TRAC-% | 98.68% | 99.51% | 99.98% | 99.98% | 99.98% |
| B2M-% | 65.91% | 68.60% | 65.91% | 70.50% | 71.10% |
| CD70-% | 99.87% | 99.10% | 99.98% | 99.62% | 99.57% |
| Regnase Indel % | 97.40% | 96.90% | 95.20% | 96.7% | 96.4% |
| TGFBRII Indel % | 85.20% | 83.00% | 85.80% | 86.9% | 87.5% |
| CAR + % | 84.10% | 80.00% | 80.54% | 82.30% | 83.80% |
| HDR | 58.35% | 62.20% | 76.10% | | |
| CD5 + % | 98.70% | 98.50% | 99.80% | 97.20% | 98.00% |

In vitro Cell Kill Assay. The ability of the anti-CD70 CAR T cell product to kill CD70 positive ACHN and U-87 target cells was assessed using a flow cytometry-based cytotoxicity assay. In brief, 50,000 human target cells (CD70-positive cells, A498 and ACHN, and CD70-negative cells, MCF7) per well were plated in an opaque-walled 96-well plate overnight. The next day, the cells were labeled with eFluor670 and incubated for 24 hours with anti-CD70 CAR T cell product at ratios of 0.125:1, 0.25:1, 0.5:1, 1:1, 2:1, and 4:1 of T cells to target cells. Reference CAR cells (allogeneic T cells that express an anti-CD70 CAR, and that have genetically disrupted CD70, TRAC, and β2M genes) and RNP− cells were also assessed as a comparison. After manually washing off T cells with PBS, the remaining viable target cells were quantified using a CellTiter-Glo luminescent cell viability assay (CellTiter-Glo 2.0® Assay, Promega). The anti-CD70 CAR T cell product showed target cell cytotoxicity comparable to the Reference CAR cells (FIGS. 10A-10B).

In vivo Study. The ability of the anti-CD70 CAR T cell product to kill tumors in mice was studied in vivo. 5e6 Caki-1 tumor cells were inoculated into the right flank of NSG mice 22 days prior to CAR-T administration. Tumor size ($mm^3$) was evaluated every 3-4 days post CAR-T administration. Anti-CD70 CAR T cell product, as well as the Reference CAR cells, were administrated at dose of 8e6 CAR+ cells per mouse. Four to five mice were included per group. Untreated mice were used as negative control. The in vivo study indicated similar tumor growth kinetics (i.e., suppression of tumor growth) between anti-CD70 CAR T cell product and Reference CAR cells (FIG. 11A) with complete control or clearance of tumor in treated groups. At day 39, the mice were further inoculated with ACHN tumor cells in the left flank at dose of 1e7 cells per mouse as rechallenge. Tumor size ($mm^3$) developed by ACHN cells was evaluated every 3-4 days. The rechallenged in vivo study indicated continued increased in tumor size in no treatment and the Reference CAR cells treated mice, while the anti-CD70 CAR T cell product treated mice demonstrated shrink in tumor size on day 50 and undetectable tumor on day 60, indicating suppression of tumor growth (FIG. 11B).

The various lots of anti-CD70 CAR T cell product was further characterized by subset phenotype analysis and exhaustion phenotype analysis. Example flow panels are shown in Table 32.

Briefly, the cells were collected and counted by staining with Trypan Blue or other dyte and loaded into a hemocytometer. Cells at $0.5\times10^6$-$1\times10^6$ were taken into an Eppendorf, washed and centrifuged. The cells were then resuspended in 100 μL CAR primary antibody and incubated at 4° C. for 1 hour. The cells were then washed twice and incubated with secondary antibody at 4° C. for 30 min. After washing, the cells were resuspended in buffer and acquisition done.

TABLE 32

| Flow Panels for Characterization of T Cell Populations | |
|---|---|
| Exhaustion | Subset |
| CD4 | CD4 |
| CD8 | CD8 |
| CAR | CD45RO |
| CD57 | CD45RA |
| Lag3 | CD62L |
| PD-1 | CD27 |
| Tim3 | |

Four separate lots were assessed for memory cell markers. Within viable cells, CAR+, CD4+CAR+, and CD8+ CAR+ populations were defined as Naïve T cells, central memory (CM) T cells, effector memory (EM) T cells, and terminal effector (TE) T cells, respectively. These populations within the anti-CD70 CAR T cell product were defined as subsets. FIGS. 9A-9D and Table 33 show the percentage of naïve, terminal effector (TE), effector memory (EM), and central memory (CM) cells in total viable cells (FIG. 9A), CAR+ cells (FIG. 9B), CD4+ CAR+ cells (FIG. 9C), and CD8+ CAR+ cells (FIG. 9D). >90% of viable cells, CAR+ cells, and CD4+ CAR+ cells are composed of Naïve T cells, CM and EM in the 4 lots tested. In all the lots tested, there are greater 80% of Naïve T cells, CM and EM within CD8+ CAR+ cells.

Four separate lots were also tested for exhaustion markers, CD57, Lag3, PD1, and Tim3. Table 34 shows that within all subsets of cells, exhaustion markers, CD57, Lag3 and PD1 had low expression. Tim3 had an expression profile of 62-78% in viable CAR+, CAR+CD4+, and CAR+.

TABLE 33

| Subsets (% averages) | | | | |
|---|---|---|---|---|
| | Viable | CAR+ | CAR+ CD4+ | CAR+ CD8+ |
| Naïve | 41 | 41 | 54 | 25 |
| CM | 37 | 39 | 32 | 51 |
| EM | 14 | 12 | 10 | 11 |
| TE | 9 | 8 | 4 | 14 |

TABLE 34

| Exhaustion markers (% averages) | | | | |
|---|---|---|---|---|
| | Viable | CAR+ | CAR+ CD8+ | CAR+ CD4+ |
| CD57 | 2 | 2 | 2 | 3 |
| Lag3 | 5 | 6 | 11 | 1 |
| PD1 | 1 | 1 | 1 | 1 |
| Tim3 | 62 | 68 | 78 | 61 |

Cytokine-Independent Growth Assay

The ability of the TCRα/β-depleted anti-CD70 CAR T cell product with genetically disrupted TRAC, β2M, Regnase-1 and TGFBRII genes was evaluated using a cytokine-independent growth assay.

The CAR T cells were placed in Complete media: T-cell media composed of X-VIVO 15 media (Lonza, Basel, Switzerland), 5% human AB serum (Valley Biomedical, Winchester, VA), IL-2 (Miltenyi, Bergisch Gladbach, Germany) and IL-7 (Cellgenix, Frieburg, Germany) both used at a concentration of 100 U/mL, or Serum only media: X-VIVO 15 media containing 5% human AB serum but lacking IL-2 and IL-7. Cell expansion following cytokine withdrawal was monitored for 37 days. Cells were counted after staining with Trypan blue viability dye (final concentration of 0.2%) and a Countess II automated cell counter (Thermo Fisher Scientific, Waltham, MA).

The cell count with or without IL-2 and IL-7 is presented FIG. 17 (see also Table 35). No detectable cell growth or proliferation was observed in the absence of cytokines for the the anti-CD70 CAR T cell product with genetically disrupted TRAC, β2M, Regnase-1 and TGFBRII genes.

TABLE 35

| Cell count (log 10M) | | |
|---|---|---|
| Days | No cytokines | With cytokines |
| 0 | 5.0 | 5.0 |
| 3 | 7.1 | 11.5 |
| 6 | 4.9 | 41.4 |
| 9 | 1.2 | 129.2 |

TABLE 35-continued

| Days | Cell count (log 10M) No cytokines | With cytokines |
|---|---|---|
| 10 | 0.9 | 179.0 |
| 14 | 0.8 | 662.6 |
| 17 | 0.7 | 1203.8 |
| 20 | 0.5 | 1918.9 |
| 24 | 0.7 | 2531.6 |
| 27 | 0.5 | 2727.4 |
| 30 | 0.4 | 2800.0 |
| 34 | 0.4 | 3712.5 |
| 37 | 0.2 | 4237.5 |

Sequence Tables

The following tables provide details for the various nucleotide and amino acid sequences disclosed herein.

TABLE 3

| sgRNA Sequences and Target Gene Sequences. | | | |
|---|---|---|---|
| | | sgRNA Sequences | SEQ ID NO: |
| Regnase-1 sgRNA (R7) | Modified | A*C*G*ACGCGUGGGUGGCAAGCgUUUUagagCUagaaaUagCaaguuaaaauaaggcuaguccguuaucaacuugaaaaaguggcaccgagucggugcU*U*U*U | 2 |
| | Unmodified | ACGACGCGUGGGUGGCAAGCguuuuagagcuagaaauagcaaguuaaaauaaggcuaguccguuaucaacuugaaaaaguggcaccgagucggugcUUUU | 3 |
| Regnase-1 sgRNA spacer | Modified | a*c*g*acgcgugggugggcaagc | 4 |
| | Unmodified | ACGACGCGUGGGUGGCAAGC | 5 |
| TGFBRII sgRNA (TGFBRII2-5) | Modified | C*C*C*CUACCAUGACUUUAUUGUGGgUUUUagagCUagaaaUagcaaguuaaaauaaggcuaguccguuaucaacuugaaaaaguggcaccgagucggugcU*U*U*U | 6 |
| | Unmodified | CCCCUACCAUGACUUUAUUCUGGguuuuagagcuagaaauagcaaguuaaaauaaggcuaguccguuaucaacuugaaaaaguggcaccgagucggugcUUUU | 7 |
| TGFBRII sgRNA spacer | Modified | C*C*C*CUACCAUGACUUUAUUCUGG | 8 |
| | Unmodified | CCCCUACCAUGACUUUAUUCUGG | 9 |
| TRAC sgRNA (TA-1) | Modified | A*G*A*GCAACAGUGCUGUGGGCgUUUUagagCUagaaaUagCaaguuaaaauaaggcuaguccguuaucaacuugaaaaaguggcaccgagucggugcU*U*U*U | 10 |
| | Unmodified | AGAGCAACAGUGCUGUGGCCguuuuagagcuagaaauagcaaguuaaaauaaggcuaguccguuaucaacuugaaaaaguggcaccgagucggugcUUUU | 11 |
| TRAC sgRNA spacer | Modified | A*G*A*GCAACAGUGCUGUGGCC | 12 |
| | Unmodified | AGAGCAACAGUGCUGUGGCC | 13 |
| β2M sgRNA (B2M-1) | Modified | G*C*U*ACUCUCUCUUUCUGGGCgUUUUagagCUagaaaUagCaaguuaaaauaaggcuaguccguuaucaacuugaaaaaguggcaccgagucggugcU*U*U*U | 14 |
| | Unmodified | GCUACUCUCUCUUUCUGGCCguuuuagagcuagaaauagcaaguuaaaauaaggcuaguccguuaucaacuugaaaaaguggcaccgagucggugcUUUU | 15 |
| β2M sgRNA spacer | Modified | g*c*u*acucucucuuucuggcc | 16 |
| | Unmodified | GCUACUCUCUCUUUCUGGCC | 17 |
| CD70 sgRNA (CD70-7) | Modified | G*C*U*UUGGUCCCAUUGGUCGCgUUUUagagCUagaaaUagcaaguuaaaauaaggcuaguccguuaucaacuugaaaaaguggcaccgagucggugcU*U*U*U | 18 |
| | Unmodified | GCUUUGGUCCCAUUGGUCGCguuuuagagcuagaaauagcaaguuaaaauaaggcuaguccguuaucaacuugaaaaaguggcaccgagucggugcUUUU | 19 |
| CD70 sgRNA spacer | Modified | g*c*u*uuggucccauuggucgc | 20 |
| | Unmodified | GCUUUGGUCCCAUUGGUCGC | 21 |
| Target Sequences (PAM) | | | |
| Regnase-1 with (PAM) | ACGACGCGTGGGTGGCAAGC(GGG) | | 22 |
| Regnase-1 | ACGACGCGTGGGTGGCAAGC | | 23 |

TABLE 3-continued

| sgRNA Sequences and Target Gene Sequences. | | |
|---|---|---|
| TGFBRII with (PAM) | CCCCTACCATGACTTTATTCTGG(TGG) | 24 |
| TGFBRII | CCCCTACCATGACTTTATTCTGG | 25 |
| TRAC sgRNA with (PAM) | AGAGCAACAGTGCTGTGGCC (TGG) | 26 |
| TRAC | AGAGCAACAGTGCTGTGGCC | 27 |
| p2M with (PAM) | GCTACTCTCTCTTTCTGGCC (TGG) | 28 |
| P2M | GCTACTCTCTCTTTCTGGCC | 29 |
| CD70 with (PM, | GCTTTGGTCCCATTGGTCGC (GGG) | 30 |
| CD70 | GCTTTGGTCCCATTGGTCGC | 31 |
| **Exemplary sgRNA Formulas** | | |
| sgRNA sequence | Nnnnnnnnnnnnnnnnnnnnguuuuagagcuagaaauagcaaguuaaaauaaggc uaguccguuaucaacuugaaaaaguggcaccgagucggugcuuuu | 32 |
| sgRNA sequence | Nnnnnnnnnnnnnnnnnnnnguuuuagagcuagaaauagcaaguuaaaauaaggc uaguccguuaucaacuugaaaaaguggcaccgagucggugc | 33 |
| sgRNA sequence | n(17-30)guuuuagagcuagaaauagcaaguuaaaauaaggcuaguccguuau caacuugaaaaaguggcaccgagucggugcu(1-8) | 34 |

* indicates a nucleotide with a 2'-O-methyl phosphorothioate modification,
"n" refers to the spacer sequence at the 5' end.

TABLE 4

Edited TRAC Gene Sequence.

| Description | Sequence (Deletions indicated by dashes (-); insertions indicated by bold) | SEQ ID NO: |
|---|---|---|
| TRAC gene edit | AA---------------------GAGCAACAAATCTGACT | 35 |
| TRAC gene edit | AAGAGCAACAGTGCTGT-GCCTGGAGCAACAAATCTGACT | 36 |
| TRAC gene edit | AAGAGCAACAGTG ----- CTGGAGCAACAAATCTGACT | 37 |
| TRAC gene edit | AAGAGCAACAGT------GCCTGGAGCAACAAATCTGACT | 38 |
| TRAC gene edit | AAGAGCAACAGTG---------------------CTGACT | 39 |
| TRAC gene edit | AAGAGCAACAGTGCTGT**G**GGCCTGGAGCAACAAATCTGACT | 40 |
| TRAC gene edit | AAGAGCAACAGTGC--TGGCCTGGAGCAACAAATCTGACT | 41 |
| TRAC gene edit | AAGAGCAACAGTGCTGTG**T**GCCTGGAGCAACAAATCTGACT | 42 |

TABLE 5

Edited β2M Gene Sequence.

| Description | Sequence (Deletions indicated by dashes (-); insertions indicated by bold) | SEQ ID NO: |
|---|---|---|
| β2M gene-edit | CGTGGCCTTAGCTGTGCTCGCGCTACTCTCTCTTTCT- GCCTGGAGGCTATCCAGCGTGAGTCTCTCCTACCCTCCCGCT | 43 |
| β2M gene-edit | CGTGGCCTTAGCTGTGCTCGCGCTACTCTCTCTTTC -- GCCTGGAGGCTATCCAGCGTGAGTCTCTCCTACCCTCCCGCT | 44 |

TABLE 5-continued

| Description | Sequence (Deletions indicated by dashes (-); insertions indicated by bold) | SEQ ID NO: |
|---|---|---|
| Edited β2M Gene Sequence. | | |
| β2M gene-edit | CGTGGCCTTAGCTGTGCTCGCGCTACTCTCTCTTT----- CTGGAGGCTATCCAGCGTGAGTCTCTCCTACCCTCCCGCT | 45 |
| β2M gene-edit | CGTGGCCTTAGCTGTGCTCGCGCTACTCTCTCTTTCTG**GATA**GCCTGGAGGCT ATCCAGCGTGAGTCTCTCCTACCCTCCCGCT | 46 |
| β2M gene-edit | CGTGGCCTTAGCTGTGCTCGC------------------------- GCTATCCAGCGTGAGTCTCTCCTACCCTCCCGCT | 47 |
| β2M gene-edit | CGTGGCCTTAGCTGTGCTCGCGCTACTCTCTCTTTC**TG**TGGCCTGGAGGCTAT CCAGCGTGAGTCTCTCCTACCCTCCCGCT | 48 |

TABLE 6

| Description | Sequence (Deletions indicated by dashes (-); insertions indicated by bold) | SEQ ID NO: |
|---|---|---|
| Edited CD70 Gene Sequence. | | |
| CD70 gene-edit | CACACCACGAGGCAGATCACCAAGCCCGCG -- CAATGGGACCAAAGCAGCCCGCAGGACG | 49 |
| CD70 gene-edit | CACACCACGAGGCAGATCACCAAGCCCGCG**A**ACCAATGGGACCAAAGCAGCCC GCAGGACG | 50 |
| CD70 gene-edit | CACACCACGAGGCAGATC------------ ACCAATGGGACCAAAGCAGCCCGCAGGACG | 51 |
| CD70 gene-edit | CACACCACGAGGCAGATCACCAAGCCCGCG- CCAATGGGACCAAAGCAGCCCGCAGGACG | 52 |
| CD70 gene-edit | CACACCACGAGGCAGATCACCAAGCCCGC- ACCAATGGGACCAAAGCAGCCCGCAGGACG | 53 |
| CD70 gene-edit | CACACCACGAGGCAGATCACCA------------------------- AGCCCGCAGGACG | 54 |

TABLE 7

On-Target Gene Edited Sequences >1% Frequency in At Least One Gene Edited T Cell Donor for the REG1-Z10 gRNA. Reference on-target sequence[a]: GTGGGTGGCAAGC(GGG)TGGT (SEQ ID NO: 55)

| SEQ ID NO | Gene Edited Sequence[b] | Donor 1 (%) | Donor 2 (%) | Mean (%) | Std. Dev. (%) |
|---|---|---|---|---|---|
| 56 | GTGGGTGGCA**A**AGCGGGTGGT | 23.8 | 21.7 | 22.8 | 1.5 |
| | GT-----------GGGTGGT | 20.7 | 22.9 | 21.8 | 1.6 |
| | -----------GCGGGTGGT | 10.4 | 7.7 | 9.0 | 1.9 |
| 57 | GTGGGTGGC-AGCGGGTGGT | 7.0 | 6.5 | 6.8 | 0.4 |
| | ---------------GTGGT | 3.3 | 4.3 | 3.8 | 0.7 |
| | GTG--------------GGT | 2.8 | 4.0 | 3.4 | 0.8 |
| | ------------CGGGTGGT | 2.6 | 3.3 | 3.0 | 0.5 |
| | -------------------- | 2.0 | 3.5 | 2.8 | 1.1 |
| | GTGGGTGGC----------- | 2.4 | 1.8 | 2.1 | 0.4 |

TABLE 7-continued

On-Target Gene Edited Sequences >1% Frequency in At Least One Gene Edited T Cell Donor for the REG1-Z10 gRNA.
Reference on-target sequence[a]: GTGGGTGGCAAGC(GGG)TGGT (SEQ ID NO: 55)

| SEQ ID NO | Gene Edited Sequence[b] | Donor 1 (%) | Donor 2 (%) | Mean (%) | Std. Dev. (%) |
|---|---|---|---|---|---|
| 58 | GTGGGTGGCAT**A**GCGGGTGGT | 1.8 | 1.8 | 1.8 | 0.0 |
| | GTGGGTG------------- | 1.6 | 1.5 | 1.6 | 0.1 |
| | GTGG---------------- | 1.5 | 1.8 | 1.6 | 0.2 |
| 59 | GTGGGTGG--AGCGGGTGGT | 0.9 | 1.1 | 1.0 | 0.1 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 8

Sequences of Cas9 and CAR Construct Components

| Name Description | Sequence | SEQ ID NO: |
|---|---|---|
| Cas9 | MDKKYSIGLDIGTNSVGWAVITDEYKVPSKKFKVLGNTDRHSIKKNLIGALLFD SGETAEATRLKRTARRRYTRRKNRICYLQEIFSNEMAKVDDSFFHRLEESFLVE EDKKHERHPIFGNIVDEVAYHEKYPTIYHLRKKLVDSTDKADLRLIYLALAHMI KFRGHFLIEGDLNPDNSDVDKLFIQLVQTYNQLFEENPINASGVDAKAILSARL SKSRRLENLIAQLPGEKKNGLFGNLIALSLGLTPNFKSNFDLAEDAKLQLSKDT YDDDLDNLLAQIGDQYADLFLAAKNLSDAILLSDILRVNTEITKAPLSASMIKR YDEHHQDLTLLKALVRQQLPEKYKEIFFDQSKNGYAGYIDGGASQEEFYKFIKP ILEKMDGTEELLVKLNREDLLRKQRTFDNGSIPHQIHLGELHAILRRQEDFYPF LKDNREKIEKILTFRIPYYVGPLARGNSRFAWMTRKSEETITPWNFEEVVDKGA SAQSFIERMTNFDKNLPNEKVLPKHSLLYEYFTVYNELTKVKYVTEGMRKPAFL SGEQKKAIVDLLFKTNRKVTVKQLKEDYFKKIECFDSVEISGVEDRFNASLGTY HDLLKIIKDKDFLDNEENEDILEDIVLTLTLFEDREMIEERLKTYAHLFDDKVM KQLKRRRYTGWGRLSRKLINGIRDKQSGKTILDFLKSDGFANRNFMQLIHDDSL TFKEDIQKAQVSGQGDSLHEHIANLAGSPAIKKGILQTVKVVDELVKVMGRHKP ENIVIEMARENQTTQKGQKNSRERMKRIEEGIKELGSQILKEHPVENTQLQNEK LYLYYLQNGRDMYVDQELDINRLSDYDVDHIVPQSFLKDDSIDNKVLTRSDKNR GKSDNVPSEEVVKKMKNYWRQLLNAKLITQRKFDNLTKAERGGLSELDKAGFIK RQLVETRQITKHVAQILDSRMNTKYDENDKLIREVKVITLKSKLVSDFRKDFQF YKVREINNYHHAHDAYLNAVVGTALIKKYPKLESEFVYGDYKVYDVRKMIAKSE QEIGKATAKYFFYSNIMNFFKTEITLANGEIRKRPLIETNGETGEIVWDKGRDF ATVRKVLSMPQVNIVKKTEVQTGGFSKESILPKRNSDKLIARKKDWDPKKYGGF DSPTVAYSVLVVAKVEKGKSKKLKSVKELLGITIMERSSFEKNPIDFLEAKGYK EVKKDLIIKLPKYSLFELENGRKRMLASAGELQKGNELALPSKYVNFLYLASHY EKLKGSPEDNEQKQLFVEQHKHYLDEIIEQISEFSKRVILADANLDKVLSAYNK HRDKPIREQAENIIHLFTLTNLGAPAAFKYFDTTIDRKRYTSTKEVLDATLIHQ SITGLYETRIDLSQLGGD | 1 |
| CD8α transmembrane domain | IYIWAPLAGTCGVLLLSLVITLY | 60 |
| CD28 nucleotide sequence | TCAAAGCGGAGTAGGTTGTTGCATTCCGATTACATGAATATGACTCCTCGCCGG CCTGGGCCGACAAGAAAACATTACCAACCCTATGCCCCCCCACGAGACTTCGCT GCGTACAGGTCC | 61 |
| CD28 amino acid sequence | SKRSRLLHSDYMNMTPRRPGPTRKHYQPYAPPRDFAAYRS | 62 |
| CD3-zeta nucleotide sequence | CGAGTGAAGTTTTCCCGAAGCGCAGACGCTCCGGCATATCAGCAAGGACAGAAT CAGCTGTATAACGAACTGAATTTGGGACGCCGCGAGGAGTATGACGTGCTTGAT AAACGCCGGGGGAGAGACCCGGAAATGGGGGGTAAACCCCGAAGAAAGAATCCC CAAGAAGGACTCTACAATGAACTCCAGAAGGATAAGATGGCGGAGGCCTACTCA GAAATAGGTATGAAGGGCGAACGACGACGGGGAAAAGGTCACGATGGCCTCTAC CAAGGGTTGAGTACGGCAACCAAAGATACGTACGATGCACTGCATATGCAGGCC CTGCCTCCCAGA | 63 |
| CD3-zeta amino acid sequence | RVKFSRSADAPAYQQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR | 64 |
| CD19 VH | EVKLQESGPGLVAPSQSLSVTCTVSGVSLPDYGVSWIRQPPRKGLEWLGVIWGS ETTYYNSALKSRLTIIKDNSKSQVFLKMNSLQTDDTAIYYCAKHYYYGGSYAMD YWGQGTSVTVSS | 65 |

TABLE 8-continued

Sequences of Cas9 and CAR Construct Components

| Name Description | Sequence | SEQ ID NO: |
|---|---|---|
| CD19 VL | DIQMTQTTSSLSASLGDRVTISCRASQDISKYLNWYQQKPDGTVKLLIYHTSRL<br>HSGVPSRFSGSGSGTDYSLTISNLEQEDIATYFCQQGNTLPYTFGGGTKLEIT | 66 |
| CD 19 linker | GSTSGSGKPGSGEGSTKG | 67 |
| Anti-CD19 scFv coding sequence | GATATTCAGATGACTCAGACCACCAGTAGCTTGTCTGCCTCACTGGGAG<br>ACCGAGTAACAATCTCCTGCAGGGCAAGTCAAGACATTAGCAAATACCT<br>CAATTGGTACCAGCAGAAGCCCGACGGAACGGTAAAACTCCTCATCTAT<br>CATACGTCAAGGTTGCATTCCGGAGTACCGTCACGATTTTCAGGTTCTG<br>GGAGCGGAACTGACTATTCCTTGACTATTTCAAACCTCGAGCAGGAGGA<br>CATTGCGACATATTTTTGTCAACAAGGTAATACCCTCCCTTACACTTTC<br>GGAGGAGGAACCAAACTCGAAATTACCGGGTCCACCAGTGGCTCTGGGA<br>AGCCTGGCAGTGGAGAAGGTTCCACTAAAGGCGAGGTGAAGCTCCAGGA<br>GAGCGGCCCCGGTCTCGTTGCCCCCAGTCAAAGCCTCTCTGTAACGTGC<br>ACAGTGAGTGGTGTATCATTGCCTGATTATGGCGTCTCCTGGATAAGGC<br>AGCCCCCGCGAAAGGGTCTTGAATGGCTTGGGGTAATATGGGGCTCAGA<br>GACAACGTATTATAACTCCGCTCTCAAAAGTCGCTTGACGATAATAAAA<br>GATAACTCCAAGAGTCAAGTTTTCCTTAAAATGAACAGTTTGCAGACTG<br>ACGATACCGCTATATATTATTGTGCTAAACATTATTACTACGGCGGTAG<br>TTACGCGATGGATTATTGGGGGCAGGGGACTTCTGTCACAGTCAGTAGT | 68 |
| Anti-CD19 scFv amino acid sequence Linker underlined | DIQMTQTTSSLSASLGDRVTISCRASQDISKYLNWYQQKPDGTVKLLIY<br>HTSRLHSGVPSRFSGSGSGTDYSLTISNLEQEDIATYFCQQGNTLPYTF<br>GGGTKLEITGSTSGSGKPGSGEGSTKGEVKLQESGPGLVAPSQSLSVTC<br>TVSGVSLPDYGVSWIRQPPRKGLEWLGVIWGSETTYYNSALKSRLTIIK<br>DNSKSQVFLKMNSLQTDDTAIYYCAKHYYYGGSYAMDYWGQGTSVTVSS | 69 |
| Anti-CD19 CAR FMC63-28Z (FMC63-CD8[tm] CD28[co-stimulatory domain]-CD3z) Nucleic Acid | ATGCTTCTTTTGGTTACGTCTCTGTTGCTTTGCGAACTTCCTCATCCAGCGTTC<br>TTGCTGATCCCCGATATTCAGATGACTCAGACCACCAGTAGCTTGTCTGCCTCA<br>CTGGGAGACCGAGTAACAATCTCCTGCAGGGCAAGTCAAGACATTAGCAAATAC<br>CTCAATTGGTACCAGCAGAAGCCCGACGGAACGGTAAAACTCCTCATCTATCAT<br>ACGTCAAGGTTGCATTCCGGAGTACCGTCACGATTTTCAGGTTCTGGGAGCGGA<br>ACTGACTATTCCTTGACTATTTCAAACCTCGAGCAGGAGGACATTGCGACATAT<br>TTTTGTCAACAAGGTAATACCCTCCCTTACACTTTCGGAGGAGGAACCAAACTC<br>GAAATTACCGGGTCCACCAGTGGCTCTGGGAAGCCTGGCAGTGGAGAAGGTTCC<br>ACTAAAGGCGAGGTGAAGCTCCAGGAGAGCGGCCCCGGTCTCGTTGCCCCCAGT<br>CAAAGCCTCTCTGTAACGTGCACAGTGAGTGGTGTATCATTGCCTGATTATGGC<br>GTCTCCTGGATAAGGCAGCCCCCGCGAAAGGGTCTTGAATGGCTTGGGGTAATA<br>TGGGGCTCAGAGACAACGTATTATAACTCCGCTCTCAAAAGTCGCTTGACGATA<br>ATAAAAGATAACTCCAAGAGTCAAGTTTTCCTTAAAATGAACAGTTTGCAGACT<br>GACGATACCGCTATATATTATTGTGCTAAACATTATTACTACGGCGGTAGTTAC<br>GCGATGGATTATTGGGGGCAGGGGACTTCTGTCACAGTCAGTAGTGCTGCTGCC<br>TTTGTCCCGGTATTTCTCCCAGCCAAACCGACCACGACTCCCGCCCCGCGCCCT<br>CCGACACCCGCTCCCACCATCGCCTCTCAACCTCTTAGTCTTCGCCCCGAGGCA<br>TGCCGACCCGCCGCCGGGGGTGCTGTTCATACGAGGGGCTTGGACTTCGCTTGT<br>GATATTTACATTTGGGCTCCGTTGGCGGGTACGTGCGGCGTCCTTTTGTTGTCA<br>CTCGTTATTACTTTGTATTGTAATCACAGGAATCGCTCAAAGCGGAGTAGGTTG<br>TTGCATTCCGATTACATGAATATGACTCCTCGCCGGCCTGGGCCGACAAGAAAA<br>CATTACCAACCCTATGCCCCCCCACGAGACTTCGCTGCGTACAGGTCCCGAGTG<br>AAGTTTTCCCGAAGCGCAGACGCTCCGGCATATCAGCAAGGACAGAATCAGCTG<br>TATAACGAACTGAATTTGGGACGCCGCGAGGAGTATGACGTGCTTGATAAACGC<br>CGGGGGAGAGACCCGGAAATGGGGGGTAAACCCCGAAGAAAGAATCCCCAAGAA<br>GGACTCTACAATGAACTCCAGAAGGATAAGATGGCGGAGGCCTACTCAGAAATA<br>GGTATGAAGGGCGAACGACGACGGGGAAAAGGTCACGATGGCCTCTACCAAGGG<br>TTGAGTACGGCAACCAAAGATACGTACGATGCACTGCATATGCAGGCCCTGCCT<br>CCCAGA | 70 |
| Anti-CD19 CAR FMC63-28Z (FMC63-CD8[tm] CD28[co-stimulatory domain]-CD3z) Amino Acid | *MLLLVTSLLLCELPHPAFLLIP*DIQMTQTTSSLSASLGDRVTISCRASQDISKY<br>LNWYQQKPDGTVKLLIYHTSRLHSGVPSRFSGSGSGTDYSLTISNLEQEDIATY<br>FCQQGNTLPYTFGGGTKLEITGSTSGSGKPGSGEGSTKGEVKLQESGPGLVAPS<br>QSLSVTCTVSGVSLPDYGVSWIRQPPRKGLEWLGVIWGSETTYYNSALKSRLTI<br>IKDNSKSQVFLKMNSLQTDDTAIYYCAKHYYYGGSYAMDYWGQGTSVTVSSAAA<br>FVPVFLPAKPTTTPAPRPPTPAPTIASQPLSLRPEACRPAAGGAVHTRGLDFAC<br>DIYIWAPLAGTCGVLLLSLVITLYCNHRNRSKRSRLLHSDYMNMTPRRPGPTRK<br>HYQPYAPPRDFAAYRSRVKFSRSADAPAYQQGQNQLYNELNLGRREEYDVLDKR<br>RGRDPEMGGKPRRKNPQEGLYNELQKDKMAEAYSEIGMKGERRRGKGHDGLYQG<br>LSTATKDTYDALHMQALPPR | 71 |
| CD70 VH | QVQLVQSGAEVKKPGASVKVSCKASGYTFTNYGMNWVRQAPGQGLKWMGWINTY<br>TGEPTYADAFKGRVTMTRDTSISTAYMELSRLRSDDTAVYYCARDYGDYGMDYW<br>GQGTTVTVSS | 72 |

TABLE 8-continued

| Sequences of Cas9 and CAR Construct Components | | |
|---|---|---|
| Name Description | Sequence | SEQ ID NO: |
| CD70 VL | DIVMTQSPDSLAVSLGERATINCRASKSVSTSGYSFMHWYQQKPGQPPKLLIYL ASNLESGVPDRFSGSGSGTDFTLTISSLQAEDVAVYYCQHSREVPWTFGQGTKV EIK | 73 |
| Linker | GGGGSGGGGSGGGGSG | 74 |
| CD70B scFv nucleotide sequence | CAGGTCCAGTTGGTGCAAAGCGGGGCGGAGGTGAAAAAACCCGGCGCTTCCGTG AAGGTGTCCTGTAAGGCGTCCGGTTATACGTTCACGAACTACGGGATGAATTGG GTTCGCCAAGCGCCGGGGCAGGGACTGAAATGGATGGGGTGGATAAATACCTAC ACCGGCGAACCTACATACGCCGACGCTTTTAAAGGGCGAGTCACTATGACGCGC GATACCAGCATATCCACCGCATACATGGAGCTGTCCCGACTCCGGTCAGACGAC ACGGCTGTCTACTATTGTGCTCGGGACTATGGCGATTATGGCATGGACTACTGG GGTCAGGGTACGACTGTAACAGTTAGTAGTGGTGGAGGCGGCAGTGGCGGGGGG GGAAGCGGAGGAGGGGGTTCTGGTGACATAGTTATGACCCAATCCCCAGATAGT TTGGCGGTTTCTCTGGGCGAGAGGGCAACGATTAATTGTCGCGCATCAAAGAGC GTTTCAACGAGCGGATATTCTTTTATGCATTGGTACCAGCAAAAACCCGGACAA CCGCCGAAGCTGCTGATCTACTTGGCTTCAAATCTTGAGTCTGGGGTGCCGGAC CGATTTTCTGGTAGTGGAAGCGGAACTGACTTTACGCTCACGATCAGTTCACTG CAGGCTGAGGATGTAGCGGTCTATTATTGCCAGCACAGTAGAGAAGTCCCCTGG ACCTTCGGTCAAGGCACGAAAGTAGAAATTAAA | 75 |
| CD70B scFv amino acid sequence (linker underlined) | QVQLVQSGAEVKKPGASVKVSCKASGYTFTNYGMNWVRQAPGQGLKWMGWINTY TGEPTYADAFKGRVTMTRDTSISTAYMELSRLRSDDTAVYYCARDYGDYGMDYW GQGTTVTVSSGGGGSGGGGSGGGGSGDIVMTQSPDSLAVSLGERATINCRASKS VSTSGYSFMHWYQQKPGQPPKLLIYLASNLESGVPDRFSGSGSGTDFTLTISSL QAEDVAVYYCQHSREVPWTFGQGTKVEIK | 76 |
| CD70 CAR nucleotide sequence (CD70B scFv with 41BB) | ATGGCGCTTCCGGTGACAGCACTGCTCCTCCCCTTGGCGCTGTTGCTCCACGCA GCAAGGCCGCAGGTCCAGTTGGTGCAAAGCGGGGCGGAGGTGAAAAAACCCGGC GCTTCCGTGAAGGTGTCCTGTAAGGCGTCCGGTTATACGTTCACGAACTACGGG ATGAATTGGGTTCGCCAAGCGCCGGGGCAGGGACTGAAATGGATGGGGTGGATA AATACCTACACCGGCGAACCTACATACGCCGACGCTTTTAAAGGGCGAGTCACT ATGACGCGCGATACCAGCATATCCACCGCATACATGGAGCTGTCCCGACTCCGG TCAGACGACACGGCTGTCTACTATTGTGCTCGGGACTATGGCGATTATGGCATG GACTACTGGGGTCAGGGTACGACTGTAACAGTTAGTAGTGGTGGAGGCGGCAGT GGCGGGGGGGGAAGCGGAGGAGGGGGTTCTGGTGACATAGTTATGACCCAATCC CCAGATAGTTTGGCGGTTTCTCTGGGCGAGAGGGCAACGATTAATTGTCGCGCA TCAAAGAGCGTTTCAACGAGCGGATATTCTTTTATGCATTGGTACCAGCAAAAA CCCGGACAACCGCCGAAGCTGCTGATCTACTTGGCTTCAAATCTTGAGTCTGGG GTGCCGGACCGATTTTCTGGTAGTGGAAGCGGAACTGACTTTACGCTCACGATC AGTTCACTGCAGGCTGAGGATGTAGCGGTCTATTATTGCCAGCACAGTAGAGAA GTCCCCTGGACCTTCGGTCAAGGCACGAAAGTAGAAATTAAAAGTGCTGCTGCC TTTGTCCCGGTATTTCTCCCAGCCAAACCGACCACGACTCCCGCCCCGCGCCCT CCGACACCCGCTCCCACCATCGCCTCTCAACCTCTTAGTCTTCGCCCCGAGGCA TGCCGACCCGCCGCCGGGGGTGCTGTTCATACGAGGGGCTTGGACTTCGCTTGT GATATTTACATTTGGGCTCCGTTGGCGGGTACGTGCGGCGTCCTTTTGTTGTCA CTCGTTATTACTTTGTATTGTAATCACAGGAATCGCAAACGGGGCAGAAAGAAA CTCCTGTATATATTCAAACAACCATTTATGAGACCAGTACAAACTACTCAAGAG GAAGATGGCTGTAGCTGCCGATTTCCAGAAGAAGAAGAAGGAGGATGTGAACTG CGAGTGAAGTTTTCCCGAAGCGCAGACGCTCCGGCATATCAGCAAGGACAGAAT CAGCTGTATAACGAACTGAATTTGGGACGCCGCGAGGAGTATGACGTGCTTGAT AAACGCCGGGGGAGAGACCCGGAAATGGGGGGTAAACCCCGAAGAAAGAATCCC CAAGAAGGACTCTACAATGAACTCCAGAAGGATAAGATGGCGGAGGCCTACTCA GAAATAGGTATGAAGGGCGAACGACGACGGGGAAAAGGTCACGATGGCCTCTAC CAAGGGTTGAGTACGGCAACCAAAGATACGTACGATGCACTGCATATGCAGGCC CTGCCTCCCAGATAA | 77 |
| CD70 CAR amino acid sequence (CD70B scFv with 41BB) | *MALPVTALLLPLALLLHAARP*QVQPVQSGAEVKKPGASVKVSCKASGYTFTNYG MNWVRQAPGQGLKWMGWINTYTGEPTYADAFKGRVTMTRDTSISTAYMELSRLR SDDTAVYYCARDYGDYGMDYWGQGTTVTVSSGGGGSGGGGSGGGGSGDIVMTQS PDSLAVSLGERATINCRASKSVSTSGYSFMHWYQQKPGQPPKLLIYLASNLESG VPDRFSGSGSGTDFTLTISSLQAEDVAVYYCQHSREVPWTFGQGTKVEIKSAAA FVPVFLPAKPTTTPAPRPPTPAPTIASQPLSLRPEACRPAAGGAVHTRGLDFAC DIYIWAPLAGTCGVLLLSLVITLYCNHRNRKRGRKKLLYIFKQPFMRPVQTTQE EDGCSCRFPEEEEGGCELRVKFSRSADAPAYQQGQNQLYNELNLGRREEYDVLD KRRGRDPEMGGKPRRKNPQEGLYNELQKDKMAEAYSEIGMKGERRRGKGHDGLY QGLSTATKDTYDALHMQALPPR | 78 |

TABLE 8-continued

Sequences of Cas9 and CAR Construct Components

| Name Description | Sequence | SEQ ID NO: |
|---|---|---|
| GM-CSF signal peptide | ATGCTTCTTTTGGTTACGTCTCTGTTGCTTTGCGAACTTCCTCATCCAGCGTTC TTGCTGATCCCC | 79 |
| GM-CSF signal peptide | MLLLVTSLLLCELPHPAFLLIP | 80 |
| CD8a extracellular + CD8a transmembrane + 5' Linker (underlined) | GCTGCTGCCTTTGTCCCGGTATTTCTCCCAGCCAAACCGACCACGACTCCCGCC CCGCGCCCTCCGACACCCGCTCCCACCATCGCCTCTCAACCTCTTAGTCTTCGC CCCGAGGCATGCCGACCCGCCGCCGGGGGTGCTGTTCATACGAGGGGCTTGGAC TTCGCTTGTGATATTTACATTTGGGCTCCGTTGGCGGGTACGTGCGGCGTCCTT TTGTTGTCACTCGTTATTACTTTGTATTGTAATCACAGGAATCGC | 81 |
| CD8a extracellular + CD8a transmembrane (without linker) | TTTGTCCCGGTATTTCTCCCAGCCAAACCGACCACGACTCCCGCCCCGCGCCCT CCGACACCCGCTCCCACCATCGCCTCTCAACCTCTTAGTCTTCGCCCCGAGGCA TGCCGACCCGCCGCCGGGGGTGCTGTTCATACGAGGGGCTTGGACTTCGCTTGT GATATTTACATTTGGGCTCCGTTGGCGGGTACGTGCGGCGTCCTTTTGTTGTCA CTCGTTATTACTTTGTATTGTAATCACAGGAATCGC | 82 |
| CD8a extracellular + CD8a transmembrane | FVPVFLPAKPTTTPAPRPPTPAPTIASQPLSLRPEACRPAAGGAVHTRGLDFAC DIYIWAPLAGTCGVLLLSLVITLYCNHRNR | 83 |

TABLE 9

AAV Donor Template Sequences

| Name Description | Sequence | SEQ ID NO: |
|---|---|---|
| Left ITR (5' ITR) | TTGGCCACTCCCTCTCTGCGCGCTCGCTCGCTCACTGAGGCCGGGCGAC CAAAGGTCGCCCGACGCCCGGGCTTTGCCCGGGCGGCCTCAGTGAGCGA GCGAGCGCGCAGAGAGGGAGTGGCCAACTCCATCACTAGGGGTTCCT | 84 |
| Left ITR (5' ITR) (alternate) | CCTGCAGGCAGCTGCGCGCTCGCTCGCTCACTGAGGCCGCCCGGGCGTCGGGCG ACCTTTGGTCGCCCGGCCTCAGTGAGCGAGCGAGCGCGCAGAGAGGGAGTGGCC AACTCCATCACTAGGGGTTCCT | 85 |
| Right ITR (3' ITR | AGGAACCCCTAGTGATGGAGTTGGCCACTCCCTCTCTGCGCGCTCGCTC GCTCACTGAGGCCGCCCGGGCAAAGCCCGGGCGTCGGGCGACCTTTGGT CGCCCGGCCTCAGTGAGCGAGCGAGCGCGCAGAGAGGGAGTGGCCAA | 86 |
| Right ITR (3' ITR (alternate) | AGGAACCCCTAGTGATGGAGTTGGCCACTCCCTCTCTGCGCGCTCGCTCGCTCA CTGAGGCCGGGCGACCAAAGGTCGCCCGACGCCCGGGCTTTGCCCGGGCGGCCT CAGTGAGCGAGCGAGCGCGCAGCTGCCTGCAGG | 87 |
| TRAC-LHA (800 bp) | GAGATGTAAGGAGCTGCTGTGACTTGCTCAAGGCCTTATATCGAGTAAACGGTA GTGCTGGGGCTTAGACGCAGGTGTTCTGATTTATAGTTCAAAACCTCTATCAAT GAGAGAGCAATCTCCTGGTAATGTGATAGATTTCCCAACTTAATGCCAACATAC CATAAACCTCCCATTCTGCTAATGCCCAGCCTAAGTTGGGGAGACCACTCCAGA TTCCAAGATGTACAGTTTGCTTTGCTGGGCCTTTTTCCCATGCCTGCCTTTACT CTGCCAGAGTTATATTGCTGGGGTTTTGAAGAAGATCCTATTAAATAAAAGAAT AAGCAGTATTATTAAGTAGCCCTGCATTTCAGGTTTCCTTGAGTGGCAGGCCAG GCCTGGCCGTGAACGTTCACTGAAATCATGGCCTCTTGGCCAAGATTGATAGCT TGTGCCTGTCCCTGAGTCCCAGTCCATCACGAGCAGCTGGTTTCTAAGATGCTA TTTCCCGTATAAAGCATGAGACCGTGACTTGCCAGCCCCACAGAGCCCCGCCCT TGTCCATCACTGGCATCTGGACTCCAGCCTGGGTTGGGGCAAAGAGGGAAATGA GATCATGTCCTAACCCTGATCCTCTTGTCCCACAGATATCCAGAACCCTGACCC TGCCGTGTACCAGCTGAGAGACTCTAAATCCAGTGACAAGTCTGTCTGCCTATT CACCGATTTTGATTCTCAAACAAATGTGTCACAAAGTAAGGATTCTGATGTGTA TATCACAGACAAAACTGTGCTAGACATGAGGTCTATGGACTTCA | 88 |
| TRAC-RHA (800 bp) | TGGAGCAACAAATCTGACTTTGCATGTGCAAACGCCTTCAACAACAGCATTATT CCAGAAGACACCTTCTTCCCCAGCCCAGGTAAGGGCAGCTTTGGTGCCTTCGCA GGCTGTTTCCTTGCTTCAGGAATGGCCAGGTTCTGCCCAGAGCTCTGGTCAATG ATGTCTAAAACTCCTCTGATTGGTGGTCTCGGCCTTATCCATTGCCACCAAAAC CCTCTTTTTACTAAGAAACAGTGAGCCTTGTTCTGGCAGTCCAGAGAATGACAC GGGAAAAAAGCAGATGAAGAGAAGGTGGCAGGAGAGGGCACGTGGCCCAGCCTC AGTCTCTCCAACTGAGTTCCTGCCTGCCTGCCTTTGCTCAGACTGTTTGCCCCT TACTGCTCTTCTAGGCCTCATTCTAAGCCCCTTCTCCAAGTTGCCTCTCCTTAT TTCTCCCTGTCTGCCAAAAAATCTTTCCCAGCTCACTAAGTCAGTCTCACGCAG TCACTCATTAACCCACCAATCACTGATTGTGCCGGCACATGAATGCACCAGGTG TTGAAGTGGAGGAATTAAAAAGTCAGATGAGGGGTGTGCCCAGAGGAAGCACCA | 89 |

TABLE 9-continued

AAV Donor Template Sequences

| Name Description | Sequence | SEQ ID NO: |
| --- | --- | --- |
| | TTCTAGTTGGGGGAGCCCATCTGTCAGCTGGGAAAAGTCCAAATAACTTCAGAT<br>TGGAATGTGTTTTAACTCAGGGTTGAGAAAACAGCTACCTTCAGGACAAAAGTC<br>AGGGAAGGGCTCTCTGAAGAAATGCTACTTGAAGATACCAGCCCTACCAAGGGC<br>AGGGAGAGGACCCTATAGAGGCCTGGGACAGGAGCTCAATGAGAAAGG | |
| EF1α | GGCTCCGGTGCCCGTCAGTGGGCAGAGCGCACATCGCCCACAGTCCCCGAGAAG<br>TTGGGGGGAGGGGTCGGCAATTGAACCGGTGCCTAGAGAAGGTGGCGCGGGGTA<br>AACTGGGAAAGTGATGTCGTGTACTGGCTCCGCCTTTTTCCCGAGGGTGGGGGA<br>GAACCGTATATAAGTGCAGTAGTCGCCGTGAACGTTCTTTTTCGCAACGGGTTT<br>GCCGCCAGAACACAGGTAAGTGCCGTGTGTGGTTCCCGCGGGCCTGGCCTCTTT<br>ACGGGTTATGGCCCTTGCGTGCCTTGAATTACTTCCACTGGCTGCAGTACGTGA<br>TTCTTGATCCCGAGCTTCGGGTTGGAAGTGGGTGGGAGAGTTCGAGGCCTTGCG<br>CTTAAGGAGCCCCTTCGCCTCGTGCTTGAGTTGAGGCCTGGCCTGGGCGCTGGG<br>GCCGCCGCGTGCGAATCTGGTGGCACCTTCGCGCCTGTCTCGCTGCTTTCGATA<br>AGTCTCTAGCCATTTAAAATTTTTGATGACCTGCTGCGACGCTTTTTTTCTGGC<br>AAGATAGTCTTGTAAATGCGGGCCAAGATCTGCACACTGGTATTTCGGTTTTTG<br>GGGCCGCGGGCGGCGACGGGGCCCGTGCGTCCCAGCGCACATGTTCGGCGAGGC<br>GGGGCCTGCGAGCGCGGCCACCGAGAATCGGACGGGGGTAGTCTCAAGCTGGCC<br>GGCCTGCTCTGGTGCCTGGCCTCGCGCCGCCGTGTATCGCCCCGCCCTGGGCGG<br>CAAGGCTGGCCCGGTCGGCACCAGTTGCGTGAGCGGAAAGATGGCCGCTTCCCG<br>GCCCTGCTGCAGGGAGCTCAAAATGGAGGACGCGGCGCTCGGGAGAGCGGGCGG<br>GTGAGTCACCCACACAAAGGAAAAGGGCCTTTCCGTCCTCAGCCGTCGCTTCAT<br>GTGACTCCACGGAGTACCGGGCGCCGTCCAGGCACCTCGATTAGTTCTCGAGCT<br>TTTGGAGTACGTCGTCTTTAGGTTGGGGGGAGGGGTTTTATGCGATGGAGTTTC<br>CCCACACTGAGTGGGTGGAGACTGAAGTTAGGCCAGCTTGGCACTTGATGTAAT<br>TCTCCTTGGAATTTGCCCTTTTTGAGTTTGGATCTTGGTTCATTCTCAAGCCTC<br>AGACAGTGGTTCAAAGTTTTTTTCTTCCATTTCAGGTGTCGTGA | 90 |
| CD19 LHA to RHA | GAGATGTAAGGAGCTGCTGTGACTTGCTCAAGGCCTTATATCGAGTAAA<br>CGGTAGTGCTGGGGCTTAGACGCAGGTGTTCTGATTTATAGTTCAAAAC<br>CTCTATCAATGAGAGAGCAATCTCCTGGTAATGTGATAGATTTCCCAAC<br>TTAATGCCAACATACCATAAACCTCCCATTCTGCTAATGCCCAGCCTAA<br>GTTGGGGAGACCACTCCAGATTCCAAGATGTACAGTTTGCTTTGCTGGG<br>CCTTTTTCCCATGCCTGCCTTTACTCTGCCAGAGTTATATTGCTGGGGT<br>TTTGAAGAAGATCCTATTAAATAAAAGAATAAGCAGTATTATTAAGTAG<br>CCCTGCATTTCAGGTTTCCTTGAGTGGCAGGCCAGGCCTGGCCGTGAAC<br>GTTCACTGAAATCATGGCCTCTTGGCCAAGATTGATAGCTTGTGCCTGT<br>CCCTGAGTCCCAGTCCATCACGAGCAGCTGGTTTCTAAGATGCTATTTC<br>CCGTATAAAGCATGAGACCGTGACTTGCCAGCCCCACAGAGCCCCGCCC<br>TTGTCCATCACTGGCATCTGGACTCCAGCCTGGGTTGGGGCAAAGAGGG<br>AAATGAGATCATGTCCTAACCCTGATCCTCTTGTCCCACAGATATCCAG<br>AACCCTGACCCTGCCGTGTACCAGCTGAGAGACTCTAAATCCAGTGACA<br>AGTCTGTCTGCCTATTCACCGATTTTGATTCTCAAACAAATGTGTCACA<br>AAGTAAGGATTCTGATGTGTATATCACAGACAAAACTGTGCTAGACATG<br>AGGTCTATGGACTTCAGGCTCCGGTGCCCGTCAGTGGGCAGAGCGCACA<br>TCGCCCACAGTCCCCGAGAAGTTGGGGGGAGGGGTCGGCAATTGAACCG<br>GTGCCTAGAGAAGGTGGCGCGGGGTAAACTGGGAAAGTGATGTCGTGTA<br>CTGGCTCCGCCTTTTTCCCGAGGGTGGGGGAGAACCGTATATAAGTGCA<br>GTAGTCGCCGTGAACGTTCTTTTTCGCAACGGGTTTGCCGCCAGAACAC<br>AGGTAAGTGCCGTGTGTGGTTCCCGCGGGCCTGGCCTCTTTACGGGTTA<br>TGGCCCTTGCGTGCCTTGAATTACTTCCACTGGCTGCAGTACGTGATTC<br>TTGATCCCGAGCTTCGGGTTGGAAGTGGGTGGGAGAGTTCGAGGCCTTG<br>CGCTTAAGGAGCCCCTTCGCCTCGTGCTTGAGTTGAGGCCTGGCCTGGG<br>CGCTGGGGCCGCCGCGTGCGAATCTGGTGGCACCTTCGCGCCTGTCTCG<br>CTGCTTTCGATAAGTCTCTAGCCATTTAAAATTTTTGATGACCTGCTGC<br>GACGCTTTTTTTCTGGCAAGATAGTCTTGTAAATGCGGGCCAAGATCTG<br>CACACTGGTATTTCGGTTTTTGGGGCCGCGGGCGGCGACGGGGCCCGTG<br>CGTCCCAGCGCACATGTTCGGCGAGGCGGGGCCTGCGAGCGCGGCCACC<br>GAGAATCGGACGGGGGTAGTCTCAAGCTGGCCGGCCTGCTCTGGTGCCT<br>GGCCTCGCGCCGCCGTGTATCGCCCCGCCCTGGGCGGCAAGGCTGGCCC<br>GGTCGGCACCAGTTGCGTGAGCGGAAAGATGGCCGCTTCCCGGCCCTGC<br>TGCAGGGAGCTCAAAATGGAGGACGCGGCGCTCGGGAGAGCGGGCGGGT<br>GAGTCACCCACACAAAGGAAAAGGGCCTTTCCGTCCTCAGCCGTCGCTT<br>CATGTGACTCCACGGAGTACCGGGCGCCGTCCAGGCACCTCGATTAGTT<br>CTCGAGCTTTTGGAGTACGTCGTCTTTAGGTTGGGGGGAGGGGTTTTAT<br>GCGATGGAGTTTCCCCACACTGAGTGGGTGGAGACTGAAGTTAGGCCAG<br>CTTGGCACTTGATGTAATTCTCCTTGGAATTTGCCCTTTTTGAGTTTGG<br>ATCTTGGTTCATTCTCAAGCCTCAGACAGTGGTTCAAAGTTTTTTTCTT<br>CCATTTCAGGTGTCGTGACCACCATGCTTCTTTTGGTTACGTCTCTGTT<br>GCTTTGCGAACTTCCTCATCCAGCGTTCTTGCTGATCCCCGATATTCAG<br>ATGACTCAGACCACCAGTAGCTTGTCTGCCTCACTGGGAGACCGAGTAA<br>CAATCTCCTGCAGGGCAAGTCAAGACATTAGCAAATACCTCAATTGGTA<br>CCAGCAGAAGCCCGACGGAACGGTAAAACTCCTCATCTATCATACGTCA<br>AGGTTGCATTCCGGAGTACCGTCACGATTTTCAGGTTCTGGGAGCGGAA<br>CTGACTATTCCTTGACTATTTCAAACCTCGAGCAGGAGGACATTGCGAC | 91 |

TABLE 9-continued

AAV Donor Template Sequences

| Name Description | Sequence | SEQ ID NO: |
| --- | --- | --- |
| | ATATTTTTGTCAACAAGGTAATACCCTCCCTTACACTTTCGGAGGAGGA<br>ACCAAACTCGAAATTACCGGGTCCACCAGTGGCTCTGGGAAGCCTGGCA<br>GTGGAGAAGGTTCCACTAAAGGCGAGGTGAAGCTCCAGGAGAGCGGCCC<br>CGGTCTCGTTGCCCCCAGTCAAAGCCTCTCTGTAACGTGCACAGTGAGT<br>GGTGTATCATTGCCTGATTATGGCGTCTCCTGGATAAGGCAGCCCCCGC<br>GAAAGGGTCTTGAATGGCTTGGGGTAATATGGGGCTCAGAGACAACGTA<br>TTATAACTCCGCTCTCAAAAGTCGCTTGACGATAATAAAAGATAACTCC<br>AAGAGTCAAGTTTTCCTTAAAATGAACAGTTTGCAGACTGACGATACCG<br>CTATATATTATTGTGCTAAACATTATTACTACGGCGGTAGTTACGCGAT<br>GGATTATTGGGGGCAGGGGACTTCTGTCACAGTCAGTAGTGCTGCTGCC<br>TTTGTCCCGGTATTTCTCCCAGCCAAACCGACCACGACTCCCGCCCCGC<br>GCCCTCCGACACCCGCTCCCACCATCGCCTCTCAACCTCTTAGTCTTCG<br>CCCCGAGGCATGCCGACCCGCCGCCGGGGGTGCTGTTCATACGAGGGGC<br>TTGGACTTCGCTTGTGATATTTACATTTGGGCTCCGTTGGCGGGTACGT<br>GCGGCGTCCTTTTGTTGTCACTCGTTATTACTTTGTATTGTAATCACAG<br>GAATCGCTCAAAGCGGAGTAGGTTGTTGCATTCCGATTACATGAATATG<br>ACTCCTCGCCGGCCTGGGCCGACAAGAAAACATTACCAACCCTATGCCC<br>CCCCACGAGACTTCGCTGCGTACAGGTCCCGAGTGAAGTTTTCCCGAAG<br>CGCAGACGCTCCGGCATATCAGCAAGGACAGAATCAGCTGTATAACGAA<br>CTGAATTTGGGACGCCGCGAGGAGTATGACGTGCTTGATAAACGCCGGG<br>GGAGAGACCCGGAAATGGGGGGTAAACCCCGAAGAAAGAATCCCCAAGA<br>AGGACTCTACAATGAACTCCAGAAGGATAAGATGGCGGAGGCCTACTCA<br>GAAATAGGTATGAAGGGCGAACGACGACGGGGAAAAGGTCACGATGGCC<br>TCTACCAAGGGTTGAGTACGGCAACCAAAGATACGTACGATGCACTGCA<br>TATGCAGGCCCTGCCTCCCAGATAATAATAAAATCGCTATCCATCGAAG<br>ATGGATGTGTGTTGGTTTTTTGTGTGTGGAGCAACAAATCTGACTTTGC<br>ATGTGCAAACGCCTTCAACAACAGCATTATTCCAGAAGACACCTTCTTC<br>CCCAGCCCAGGTAAGGGCAGCTTTGGTGCCTTCGCAGGCTGTTTCCTTG<br>CTTCAGGAATGGCCAGGTTCTGCCCAGAGCTCTGGTCAATGATGTCTAA<br>AACTCCTCTGATTGGTGGTCTCGGCCTTATCCATTGCCACCAAAACCCT<br>CTTTTTACTAAGAAACAGTGAGCCTTGTTCTGGCAGTCCAGAGAATGAC<br>ACGGGAAAAAAGCAGATGAAGAGAAGGTGGCAGGAGAGGGCACGTGGCC<br>CAGCCTCAGTCTCTCCAACTGAGTTCCTGCCTGCCTGCCTTTGCTCAGA<br>CTGTTTGCCCCTTACTGCTCTTCTAGGCCTCATTCTAAGCCCCTTCTCC<br>AAGTTGCCTCTCCTTATTTCTCCCTGTCTGCCAAAAAATCTTTCCCAGC<br>TCACTAAGTCAGTCTCACGCAGTCACTCATTAACCCACCAATCACTGAT<br>TGTGCCGGCACATGAATGCACCAGGTGTTGAAGTGGAGGAATTAAAAAG<br>TCAGATGAGGGGTGTGCCCAGAGGAAGCACCATTCTAGTTGGGGGAGCC<br>CATCTGTCAGCTGGGAAAAGTCCAAATAACTTCAGATTGGAATGTGTTT<br>TAACTCAGGGTTGAGAAAACAGCTACCTTCAGGACAAAAGTCAGGGAAG<br>GGCTCTCTGAAGAAATGCTACTTGAAGATACCAGCCCTACCAAGGGCAG<br>GGAGAGGACCCTATAGAGGCCTGGGACAGGAGCTCAATGAGAAAGG | |
| CD70<br>LHA to RHA<br>(CD70B scFV with<br>41BB) | GAGATGTAAGGAGCTGCTGTGACTTGCTCAAGGCCTTATATCGAGTAAA<br>CGGTAGTGCTGGGGCTTAGACGCAGGTGTTCTGATTTATAGTTCAAAAC<br>CTCTATCAATGAGAGAGCAATCTCCTGGTAATGTGATAGATTTCCCAAC<br>TTAATGCCAACATACCATAAACCTCCCATTCTGCTAATGCCCAGCCTAA<br>GTTGGGGAGACCACTCCAGATTCCAAGATGTACAGTTTGCTTTGCTGGG<br>CCTTTTTCCCATGCCTGCCTTTACTCTGCCAGAGTTATATTGCTGGGGT<br>TTTGAAGAAGATCCTATTAAATAAAAGAATAAGCAGTATTATTAAGTAG<br>CCCTGCATTTCAGGTTTCCTTGAGTGGCAGGCCAGGCCTGGCCGTGAAC<br>GTTCACTGAAATCATGGCCTCTTGGCCAAGATTGATAGCTTGTGCCTGT<br>CCCTGAGTCCCAGTCCATCACGAGCAGCTGGTTTCTAAGATGCTATTTC<br>CCGTATAAAGCATGAGACCGTGACTTGCCAGCCCCACAGAGCCCCGCCC<br>TTGTCCATCACTGGCATCTGGACTCCAGCCTGGGTTGGGGCAAAGAGGG<br>AAATGAGATCATGTCCTAACCCTGATCCTCTTGTCCCACAGATATCCAG<br>AACCCTGACCCTGCCGTGTACCAGCTGAGAGACTCTAAATCCAGTGACA<br>AGTCTGTCTGCCTATTCACCGATTTTGATTCTCAAACAAATGTGTCACA<br>AAGTAAGGATTCTGATGTGTATATCACAGACAAAACTGTGCTAGACATG<br>AGGTCTATGGACTTCAGGCTCCGGTGCCCGTCAGTGGGCAGAGCGCACA<br>TCGCCCACAGTCCCCGAGAAGTTGGGGGGAGGGGTCGGCAATTGAACCG<br>GTGCCTAGAGAAGGTGGCGCGGGGTAAACTGGGAAAGTGATGTCGTGTA<br>CTGGCTCCGCCTTTTTCCCGAGGGTGGGGGAGAACCGTATATAAGTGCA<br>GTAGTCGCCGTGAACGTTCTTTTTCGCAACGGGTTTGCCGCCAGAACAC<br>AGGTAAGTGCCGTGTGTGGTTCCCGCGGGCCTGGCCTCTTTACGGGTTA<br>TGGCCCTTGCGTGCCTTGAATTACTTCCACTGGCTGCAGTACGTGATTC<br>TTGATCCCGAGCTTCGGGTTGGAAGTGGGTGGGAGAGTTCGAGGCCTTG<br>CGCTTAAGGAGCCCCTTCGCCTCGTGCTTGAGTTGAGGCCTGGCCTGGG<br>CGCTGGGGCCGCCGCGTGCGAATCTGGTGGCACCTTCGCGCCTGTCTCG<br>CTGCTTTCGATAAGTCTCTAGCCATTTAAAATTTTTGATGACCTGCTGC<br>GACGCTTTTTTTCTGGCAAGATAGTCTTGTAAATGCGGGCCAAGATCTG<br>CACACTGGTATTTCGGTTTTTGGGGCCGCGGGCGGCGACGGGGCCCGTG<br>CGTCCCAGCGCACATGTTCGGCGAGGCGGGGCCTGCGAGCGCGGCCACC<br>GAGAATCGGACGGGGGTAGTCTCAAGCTGGCCGGCCTGCTCTGGTGCCT<br>GGCCTCGCGCCGCCGTGTATCGCCCCGCCCTGGGCGGCAAGGCTGGCCC | 92 |

TABLE 9-continued

AAV Donor Template Sequences

| Name Description | Sequence | SEQ ID NO: |
| --- | --- | --- |
| | GGTCGGCACCAGTTGCGTGAGCGGAAAGATGGCCGCTTCCCGGCCCTGC<br>TGCAGGGAGCTCAAAATGGAGGACGCGGCGCTCGGGAGAGCGGGCGGGT<br>GAGTCACCCACACAAAGGAAAAGGGCCTTTCCGTCCTCAGCCGTCGCTT<br>CATGTGACTCCACGGAGTACCGGGCGCCGTCCAGGCACCTCGATTAGTT<br>CTCGAGCTTTTGGAGTACGTCGTCTTTAGGTTGGGGGGAGGGGTTTTAT<br>GCGATGGAGTTTCCCCACACTGAGTGGGTGGAGACTGAAGTTAGGCCAG<br>CTTGGCACTTGATGTAATTCTCCTTGGAATTTGCCCTTTTTGAGTTTGG<br>ATCTTGGTTCATTCTCAAGCCTCAGACAGTGGTTCAAAGTTTTTTTCTT<br>CCATTTCAGGTGTCGTGACCACCATGGCGCTTCCGGTGACAGCACTGCT<br>CCTCCCCTTGGCGCTGTTGCTCCACGCAGCAAGGCCGCAGGTCCAGTTG<br>GTGCAAAGCGGGGCGGAGGTGAAAAAACCCGGCGCTTCCGTGAAGGTGT<br>CCTGTAAGGCGTCCGGTTATACGTTCACGAACTACGGGATGAATTGGGT<br>TCGCCAAGCGCCGGGGCAGGGACTGAAATGGATGGGGTGGATAAATACC<br>TACACCGGCGAACCTACATACGCCGACGCTTTTAAAGGGCGAGTCACTA<br>TGACGCGCGATACCAGCATATCCACCGCATACATGGAGCTGTCCCGACT<br>CCGGTCAGACGACACGGCTGTCTACTATTGTGCTCGGGACTATGGCGAT<br>TATGGCATGGACTACTGGGGTCAGGGTACGACTGTAACAGTTAGTAGTG<br>GTGGAGGCGGCAGTGGCGGGGGGGGAAGCGGAGGAGGGGGTTCTGGTGA<br>CATAGTTATGACCCAATCCCCAGATAGTTTGGCGGTTTCTCTGGGCGAG<br>AGGGCAACGATTAATTGTCGCGCATCAAAGAGCGTTTCAACGAGCGGAT<br>ATTCTTTTATGCATTGGTACCAGCAAAAACCCGGACAACCGCCGAAGCT<br>GCTGATCTACTTGGCTTCAAATCTTGAGTCTGGGGTGCCGGACCGATTT<br>TCTGGTAGTGGAAGCGGAACTGACTTTACGCTCACGATCAGTTCACTGC<br>AGGCTGAGGATGTAGCGGTCTATTATTGCCAGCACAGTAGAGAAGTCCC<br>CTGGACCTTCGGTCAAGGCACGAAAGTAGAAATTAAAAGTGCTGCTGCC<br>TTTGTCCCGGTATTTCTCCCAGCCAAACCGACCACGACTCCCGCCCCGC<br>GCCCTCCGACACCCGCTCCCACCATCGCCTCTCAACCTCTTAGTCTTCG<br>CCCCGAGGCATGCCGACCCGCCGCCGGGGGTGCTGTTCATACGAGGGGC<br>TTGGACTTCGCTTGTGATATTTACATTTGGGCTCCGTTGGCGGGTACGT<br>GCGGCGTCCTTTTGTTGTCACTCGTTATTACTTTGTATTGTAATCACAG<br>GAATCGCAAACGGGGCAGAAAGAAACTCCTGTATATATTCAAACAACCA<br>TTTATGAGACCAGTACAAACTACTCAAGAGGAAGATGGCTGTAGCTGCC<br>GATTTCCAGAAGAAGAAGAAGGAGGATGTGAACTGCGAGTGAAGTTTTC<br>CCGAAGCGCAGACGCTCCGGCATATCAGCAAGGACAGAATCAGCTGTAT<br>AACGAACTGAATTTGGGACGCCGCGAGGAGTATGACGTGCTTGATAAAC<br>GCCGGGGGAGAGACCCGGAAATGGGGGGTAAACCCCGAAGAAAGAATCC<br>CCAAGAAGGACTCTACAATGAACTCCAGAAGGATAAGATGGCGGAGGCC<br>TACTCAGAAATAGGTATGAAGGGCGAACGACGACGGGGAAAAGGTCACG<br>ATGGCCTCTACCAAGGGTTGAGTACGGCAACCAAAGATACGTACGATGC<br>ACTGCATATGCAGGCCCTGCCTCCCAGATAATAATAAAATCGCTATCCA<br>TCGAAGATGGATGTGTGTTGGTTTTTTGTGTGTGGAGCAACAAATCTGA<br>CTTTGCATGTGCAAACGCCTTCAACAACAGCATTATTCCAGAAGACACC<br>TTCTTCCCCAGCCCAGGTAAGGGCAGCTTTGGTGCCTTCGCAGGCTGTT<br>TCCTTGCTTCAGGAATGGCCAGGTTCTGCCCAGAGCTCTGGTCAATGAT<br>GTCTAAAACTCCTCTGATTGGTGGTCTCGGCCTTATCCATTGCCACCAA<br>AACCCTCTTTTTACTAAGAAACAGTGAGCCTTGTTCTGGCAGTCCAGAG<br>AATGACACGGGAAAAAAGCAGATGAAGAGAAGGTGGCAGGAGAGGGCAC<br>GTGGCCCAGCCTCAGTCTCTCCAACTGAGTTCCTGCCTGCCTGCCTTTG<br>CTCAGACTGTTTGCCCCTTACTGCTCTTCTAGGCCTCATTCTAAGCCCC<br>TTCTCCAAGTTGCCTCTCCTTATTTCTCCCTGTCTGCCAAAAAATCTTT<br>CCCAGCTCACTAAGTCAGTCTCACGCAGTCACTCATTAACCCACCAATC<br>ACTGATTGTGCCGGCACATGAATGCACCAGGTGTTGAAGTGGAGGAATT<br>AAAAAGTCAGATGAGGGGTGTGCCCAGAGGAAGCACCATTCTAGTTGGG<br>GGAGCCCATCTGTCAGCTGGGAAAAGTCCAAATAACTTCAGATTGGAAT<br>GTGTTTTAACTCAGGGTTGAGAAAACAGCTACCTTCAGGACAAAAGTCA<br>GGGAAGGGCTCTCTGAAGAAATGCTACTTGAAGATACCAGCCCTACCAA<br>GGGCAGGGAGAGGACCCTATAGAGGCCTGGGACAGGAGCTCAATGAGAA<br>AGG | |

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value. In some embodiments, the hinge domain is a hinge domain of a naturally occurring protein.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for manufacturing genetically engineered T cells, the method comprising:

(i) providing a population of T cells, (ii) delivering to the T cells:

(a) one or more Cas9 enzymes;

(b) a first guide RNA (gRNA) targeting a Regnase-1 (Reg1) gene;

(c) a second gRNA targeting a Transforming Growth Factor Beta Receptor II (TGFBRII) gene;

(d) a third gRNA targeting a T cell receptor alpha chain constant region (TRAC) gene;

(e) optionally a fourth gRNA targeting a beta-2 microglobulin (β2M) gene; and (f) a donor template comprising a nucleic acid sequence encoding a chimeric antigen receptor flanked by a left homology arm and a right homology arm, wherein the left homology arm and the right homology arm are homologous to a locus in the TRAC gene;

thereby producing genetically engineered T cells comprising a disrupted TRAC gene, a disrupted Reg1 gene, a disrupted TGFBRII gene, optionally a disrupted β2M gene, and the nucleic acid sequence encoding the CAR, which is inserted into the TRAC gene.

2. A method for manufacturing genetically engineered T cells, the method comprising:

(i) providing a population of T cells;

(ii) activating the population of T cells in step (i) to produce a population of activated T cells;

(iii) performing a first electroporation to the activated T cells to introduce a first Cas9 enzyme, a first guide RNA (gRNA) targeting a Regnase 1 (Reg1) gene, and a second gRNA targeting a Transforming Growth Factor Beta Receptor II (TGFBRII) gene to produce a first population of genetically engineered T cells;

(iv) culturing the first population of genetically engineered T cells in a medium for T cell recovery, (v) performing a second electroporation to the recovered cells from step (iv) to introduce a second Cas9 enzyme, a third Cas9 enzyme, a third gRNA targeting a T cell receptor alpha chain constant region (TRAC) gene, and a fourth gRNA targeting a beta-2 microglobulin (β2M) gene to produce a second population of genetically engineered T cells;

(vi) incubating the second population of genetically engineered T cells with recombinant AAV particles, which comprise a donor template, wherein the donor template comprises a nucleic acid sequence encoding a chimeric antigen receptor that binds human CD19 (anti-CD19 CAR) flanked by a left homology arm and a right homology arm, wherein the left homology arm and the right homology arm are homologous to a locus in the TRAC gene;

(vii) expanding the second genetically engineered T cells to produce an expanded T cell population;

(viii) removing $TCR\alpha\beta^+$ T cells from the expanded T cell population; and (ix) harvesting the genetically engineered T cells produced in step (viii), wherein the genetically engineered T cells harvested in step (viii) comprise a disrupted TRAC gene, a disrupted β2M gene, a disrupted Reg1 gene, a disrupted TGFBRII gene, and the nucleic acid sequence encoding the anti-CD19 CAR, which is inserted into the disrupted TRAC gene.

3. The method of claim 2, wherein the activating step (ii) is performed by incubating a T cell population in the presence of a T cell activating agent in a cell culture vessel to produce the population of activated T cells.

4. The method of claim 3, wherein the T cell activating agent comprises a CD3 agonist and a CD28 agonist, optionally wherein the CD3 agonist and the CD28 agonist are attached to a nanomatrix particle.

5. The method of claim 3, wherein the activating step (ii) is performed for about 24-72 hours, optionally for about 48 hours.

6. The method of claim 2, wherein the T cell population in step (i) is derived from cryopreserved T cells enriched from human blood cells.

7. The method of claim 6, wherein the human blood cells are obtained from one or more human donors.

8. The method of claim 6, wherein the T cell population in step (i) is prepared by a process comprising: (i-a) obtaining blood cells from one or more human donors, (i-b) enriching $CD4^+$ T cells, $CD8^+$ T cells, or both from the blood cells, and optionally (i-c) freezing the enriched T cells from step (i-b).

9. The method of claim 2, wherein in step (iii), the Cas9 enzyme and the first gRNA that targets the Reg1 gene and second gRNA that targets the TGFBRII gene form an RNP complex.

10. The method of claim 8, wherein the Cas9 enzyme and the first gRNA that targets the Reg1 gene are at a weight ratio of 4:1 to 1:4, optionally 2:1 to 1:2; and/or wherein the Cas9 enzyme and the second gRNA that targets the TGFBRII gene are at a weight ratio of 4:1 to 1:4, optionally 2:1 to 1:2.

11. The method of claim 2, wherein in step (iii), (a) the activated T cells have a concentration of about $1\times10^8$ cells/ml to about $5\times10^8$ cells/ml; optionally about $3\times10^8$ cells/ml;

(b) the Cas9 enzyme has a concentration of about 40 μg/ml to about 180 μg/ml, optionally about 150 μg/ml;

and/or wherein the first gRNA that targets Reg1 has a concentration of about 40 μg/ml to about 160 μg/ml, optionally about 120 μg/ml;

(c) the Cas9 enzyme has a concentration of about 40 μg/ml to about 150 μg/ml, optionally about 120 μg/ml; and/or wherein the second gRNA that targets the TGFBRII gene has a concentration of about 80 μg/ml to about 160 μg/ml, optionally about 120 μg/ml; and/or (d) the Cas9 enzyme has a total concentration of about 250 μg/ml to about 300 μg/ml, optionally about 270 μg/ml; the first gRNA that targets Reg1 has a concentration of about 120 μg/ml, and the second gRNA that targets the TGFBRII gene has a concentration of about 120 μg/ml.

12. The method of claim 2, (a) wherein step (iv) is performed for about 48 hours; and/or (b) wherein in step (iv), the medium contains no T cell activating agent; and/or (c) wherein in step (v), each of the third gRNA that targets the TRAC gene and the fourth gRNA that targets the β2M gene forms an RNP complex with the Cas9 enzyme.

13. The method of claim 12, wherein step (iv) comprises (c); and wherein in step (v), a mixture of the RNP complexes is introduced to the recovered T cells by the second electroporation.

14. The method of claim 2, wherein in step (v), (a) the recovered T cells have a concentration of about $1\times10^8$ cells/ml to about $5\times10^8$ cells/ml; optionally about $3\times10^8$ cells/ml;

(b) the Cas9 enzyme has a total concentration of about 300 μg/ml, the third gRNA that targets the TRAC gene has a concentration of about 80 μg/ml, and/or the fourth gRNA that target β2M has a concentration of about 200 μg/ml; and/or (c) is performed for at least one hour.

15. The method of claim 2, wherein the AAV particles in step (vi) are AAV6 particles.

16. The method of claim 2, wherein the AAV particles have a multiplicity of infection (MOI) value of about 20,000 to about 50,000 vg/cell.

17. The method of claim 2, wherein step (vii) is performed by seeding the genetically engineered T cells produced in step (vi) at a density of about $0.3\times10^6$ viable cells/cm$^2$ to about $0.5\times10^6$ viable cells/cm$^2$ in one or more cell culture vessels and culturing the T cells for about 3 to about 9 days, optionally about 6 to about 9 days.

18. The method of claim 17, wherein the T cells are supplemented with interleukin-2, optionally at a concentration of about 100 IU/ml, and interleukin 7, optionally at a concentration of a concentration of 100 IU/ml, every 3 to 4 days.

19. The method of claim 17, wherein the one or more cell culture vessels are static cell culture vessels.

20. The method of claim 2, wherein step (viii) is performed by contacting the expanded T cells to beads on which anti-TCRαβ antibodies are immobilized and collecting unbound cells.

21. The method of claim 2, further comprising, recovering the T cells after removal of the TCRαβ$^+$ T cells.

22. The method of claim 2, wherein the one or more Cas9 enzymes are *Streptococcus pyogenes* Cas9 nuclease (spCas9).

23. The method of claim 2, wherein:

(a) the first gRNA that targets the Reg1 gene comprises a spacer sequence of SEQ ID NO: 5; optionally wherein the third gRNA comprises the nucleotide sequence of SEQ ID NO: 3;

(b) the second gRNA that targets the TGFBRII gene comprises a spacer sequence of SEQ ID NO: 9; optionally wherein the fourth gRNA comprises the nucleotide sequence of SEQ ID NO: 7;

(c) the third gRNA that targets the TRAC gene comprises a spacer sequence of SEQ ID NO: 13; optionally wherein the third gRNA comprises the nucleotide sequence of SEQ ID NO: 11; and/or (d) the fourth gRNA that targets the 62M gene comprises a spacer sequence of SEQ ID NO: 17; optionally wherein the fourth gRNA comprises the nucleotide sequence of SEQ ID NO: 15.

24. The method of claim 2, wherein the first gRNA that targets the Reg1 gene, the second gRNA that targets the TGFBRII gene, the third gRNA that targets the TRAC gene, and/or the fourth gRNA that targets the β2M gene comprises one or more 2'-O-methyl phosphorothioate modification.

25. The method of claim 2, wherein the anti-CD19 CAR comprises an extracellular domain targeting a cancer antigen, a transmembrane domain, a co-stimulatory domain, and a CD3ζ cytoplasmic signaling domain.

26. The method of claim 25, wherein the extracellular domain comprises a single-chain variable fragment (scFv) that binds human CD19, the transmembrane domain is derived from CD8a, and/or the co-stimulatory domain is derived from CD28.

27. The method of claim 26, wherein the scFv that binds CD19 comprises the amino acid sequence of SEQ ID NO: 69.

28. The method of claim 27, wherein the anti-CD19 CAR comprises the amino acid sequence of SEQ ID NO: 71, or the mature form thereof, which lacks the N-terminal signal peptide.

29. The method of claim 28, wherein the donor template comprises the nucleotide sequence of SEQ ID NO: 91.

30. The method of claim 29, wherein the disrupted TRAC gene comprises the nucleotide sequence of SEQ ID NO: 91.

31. A method for manufacturing genetically engineered T cells, the method comprising:

(i) providing a population of T cells;

(ii) activating the population of T cells in step (i) to produce a population of activated T cells;

(iii) performing a first electroporation to the activated T cells to introduce at least a first Cas9 enzyme, a first guide RNA (gRNA) targeting a Regnase 1 (Reg1) gene, a second gRNA targeting a Transforming Growth Factor Beta Receptor II (TGFBRII) gene, and a fourth gRNA targeting a β2M gene to produce a first population of genetically engineered T cells;

(iv) culturing the first population of genetically engineered T cells in a medium for T cell recovery, (v) performing a second electroporation to the recovered cells from step (iv) to introduce at least a second Cas9 enzyme, a third gRNA targeting a T cell receptor alpha chain constant region (TRAC) gene, and a fifth gRNA targeting a CD70 gene to produce a second population of genetically engineered T cells;

(vi) incubating the second population of genetically engineered T cells with recombinant AAV particles, which comprise a donor template, wherein the donor template comprises a nucleic acid sequence encoding a chimeric antigen receptor that binds human CD70 (anti-CD70

CAR) flanked by a left homology arm and a right homology arm, wherein the left homology arm and the right homology arm are homologous to a locus in the TRAC gene;

(vii) expanding the second genetically engineered T cells to produce an expanded T cell population;

(viii) removing TCR$\alpha\beta^+$ T cells from the expanded T cell population; and (ix) harvesting the genetically engineered T cells produced in step (viii), wherein the genetically engineered T cells harvested in step (viii) comprise a disrupted TRAC gene, a disrupted β2M gene, a disrupted Reg1 gene, a disrupted TGFBRII gene, a disrupted CD70 gene, and the nucleic acid sequence encoding the anti-CD70 CAR, which is inserted into the disrupted TRAC gene.

32. A population of genetically engineered T cells, which is produced by a method of claim 2.

33. A method for inhibiting undesired cells in a subject, the method comprising administering to a subject in need thereof an effective amount of the population of genetically engineered T cells set forth in claim 32, wherein the genetically engineered T cells express a CAR specific to CD19.

34. The method of claim 33, wherein the undesired cells are CD19+ cancer cells.

* * * * *